(12) United States Patent
Natchus et al.

(10) Patent No.: US 10,632,120 B2
(45) Date of Patent: *Apr. 28, 2020

(54) TRICYCLIC AMINO CONTAINING COMPOUNDS FOR TREATMENT OR PREVENTION OF SYMPTOMS ASSOCIATED WITH ENDOCRINE DYSFUNCTION

(71) Applicant: Emory University, Atlanta, GA (US)

(72) Inventors: Michael G. Natchus, Alpharetta, GA (US); Richard Arrendale, Acworth, GA (US); Dennis Liotta, Atlanta, GA (US); Ketan Desai, Easton, PA (US); Hyunsuk Shim, Atlanta, GA (US)

(73) Assignee: Emory University, Atlanta, GA (US)

( * ) Notice: Subject to any disclaimer, the term of this patent is extended or adjusted under 35 U.S.C. 154(b) by 4 days.

This patent is subject to a terminal disclaimer.

(21) Appl. No.: 16/550,414

(22) Filed: Aug. 26, 2019

(65) Prior Publication Data

US 2019/0381042 A1 Dec. 19, 2019

Related U.S. Application Data

(63) Continuation of application No. 15/618,814, filed on Jun. 9, 2017, which is a continuation of application No. 14/934,715, filed on Nov. 6, 2015, now abandoned, which is a continuation of application No. 14/356,302, filed as application No. PCT/US2012/063796 on Nov. 7, 2012, now Pat. No. 9,205,085.

(Continued)

(51) Int. Cl.

| | | |
|---|---|---|
| *A61K 31/506* | (2006.01) |
| *A61K 38/20* | (2006.01) |
| *A61K 31/444* | (2006.01) |
| *A61K 31/167* | (2006.01) |
| *A61K 31/138* | (2006.01) |
| *A61K 31/137* | (2006.01) |
| *C07D 239/42* | (2006.01) |
| *C07D 213/72* | (2006.01) |
| *C07C 255/58* | (2006.01) |
| *C07C 233/64* | (2006.01) |
| *C07C 211/53* | (2006.01) |
| *C07D 401/12* | (2006.01) |
| *C07D 213/74* | (2006.01) |
| *A61K 31/505* | (2006.01) |
| *C07D 403/12* | (2006.01) |
| *A61K 31/58* | (2006.01) |
| *A61K 31/575* | (2006.01) |
| *A61K 31/57* | (2006.01) |
| *A61K 31/4166* | (2006.01) |
| *A61K 45/06* | (2006.01) |
| *C07C 211/52* | (2006.01) |
| *C07C 237/40* | (2006.01) |
| *C07C 233/75* | (2006.01) |
| *C07C 233/65* | (2006.01) |
| *C07C 233/58* | (2006.01) |
| *C07C 233/11* | (2006.01) |
| *C07C 211/27* | (2006.01) |
| *C07C 279/18* | (2006.01) |
| *C07C 279/04* | (2006.01) |
| *C07C 229/60* | (2006.01) |

(52) U.S. Cl.
CPC .......... *A61K 31/506* (2013.01); *A61K 31/137* (2013.01); *A61K 31/138* (2013.01); *A61K 31/167* (2013.01); *A61K 31/4166* (2013.01); *A61K 31/444* (2013.01); *A61K 31/505* (2013.01); *A61K 31/57* (2013.01); *A61K 31/575* (2013.01); *A61K 31/58* (2013.01); *A61K 38/2073* (2013.01); *A61K 45/06* (2013.01); *C07C 211/53* (2013.01); *C07C 233/64* (2013.01); *C07C 255/58* (2013.01); *C07D 213/72* (2013.01); *C07D 213/74* (2013.01); *C07D 239/42* (2013.01); *C07D 401/12* (2013.01); *C07D 403/12* (2013.01); *C07C 211/27* (2013.01); *C07C 211/52* (2013.01); *C07C 229/60* (2013.01); *C07C 233/11* (2013.01); *C07C 233/58* (2013.01); *C07C 233/65* (2013.01); *C07C 233/75* (2013.01); *C07C 237/40* (2013.01); *C07C 279/04* (2013.01); *C07C 279/18* (2013.01)

(58) Field of Classification Search
None
See application file for complete search history.

(56) References Cited

U.S. PATENT DOCUMENTS

| 8,008,312 | B2 | 8/2011 | Shim |
| 2006/0264451 | A1* | 11/2006 | Shim et al. ................... 514/275 |

FOREIGN PATENT DOCUMENTS

| JP | 59-022964 | 2/1984 |
| WO | WO 2006/074428 | 7/2006 |

(Continued)

OTHER PUBLICATIONS

Zhan Weigiang et al., "Discovery of small molecule CXCR4 antagonists," Journal of Medicinal Chemistry, American Chemical Society, vol. 50, No. 23, Nov. 1, 2007, 5655-5664.

(Continued)

*Primary Examiner* — Dennis Heyer
(74) *Attorney, Agent, or Firm* — King & Spalding

(57) ABSTRACT

The disclosure provides methods of use of certain compounds that are useful for treating certain symptoms of endocrine disturbances, and in particular those associated with hot flashes.

8 Claims, No Drawings

Related U.S. Application Data

(60) Provisional application No. 61/556,347, filed on Nov. 7, 2011.

(56) References Cited

FOREIGN PATENT DOCUMENTS

| | | |
|---|---|---|
| WO | WO 2008/008854 | 1/2008 |
| WO | WO 2008/073459 | 6/2008 |

OTHER PUBLICATIONS

Extended European Search Report for European Patent Application No. 12846967.3, dated Mar. 23, 2015.
J.G. Cannon Chapter Nineteen in Burger's Medicinal Chemistry and Drug Discovery, Fifth Edition, vol. I: Principles and Practice, Wiley-Interscience 1995, pp. 783-802, 784.

* cited by examiner

TRICYCLIC AMINO CONTAINING COMPOUNDS FOR TREATMENT OR PREVENTION OF SYMPTOMS ASSOCIATED WITH ENDOCRINE DYSFUNCTION

CROSS REFERENCE TO RELATED APPLICATIONS

This application is continuation of U.S. patent application Ser. No. 15/618,814, filed Jun. 9, 2017, which is a continuation of U.S. patent application Ser. No. 14/934,715, filed Nov. 6, 2015, which is a continuation of U.S. patent application Ser. No. 14/356,302, filed May 5, 2014, which is a national phase application under 35 U.S.C. § 371 of International Application No. PCT/US2012/063796, filed on Nov. 7, 2012, which claims priority to U.S. Provisional Application No. 61/556,347 filed Nov. 7, 2011, the entire contents of each application being incorporated herein by reference.

FIELD

The disclosure provides pharmaceutical compositions and methods of use of certain tricyclic amino containing compounds for the prevention or treatment of symptoms associated with endocrine disturbances typically hot flashes.

BACKGROUND

Eighty-five percent of the women in the United States experience hot flashes of some kind as they approach menopause and for the first year or two after their periods stop. Between 20 and 50% of women continue to have them for many more years. A hot flash is characterized by a sudden, intense, hot feeling on the face and upper body. Often the hot flash can be preceded or accompanied by a rapid heartbeat and sweating, nausea, dizziness, anxiety, headache, weakness, or a feeling of suffocation. Some women experience a general, overall uneasy feeling just before the hot flash. A hot flash is generally followed by a flush, leaving the sufferer reddened and perspiring. High intensity hot flashes can result in the sufferer becoming soaked in perspiration. Lower intensity flashes cause merely produce a moist upper lip. A chill often precedes the flash, but can also occur at the conclusion of the flash. When hot flashes occur during the night, they sufferer can't sleep, resulting in poor concentration, memory problems, irritability and exhaustion during the day.

Hot flashes are often due to the hormonal changes of menopause, but can also be affected by lifestyle and medications. The exact cause of hot flashes is not currently known. Some theories suggest that hot flashes are due to a drop in the body's level of female hormones called estrogens. A diminished level of estrogen has a direct effect on the hypothalamus, the part of the brain responsible for controlling appetite, sleep cycles, sex hormones, and body temperature. The body responds to reduced levels of estrogen by increasing release of neurotransmitters from the hypothalamus and these increases in epinephrine, norepinephrine, prostaglandin and serotonin cause the heart to pump faster, the blood vessels in skin to dilate and sweat glands release sweat. Some people's skin temperature can rise six degrees Centigrade during a hot flash. Areas of dilation of blood vessels in the skin are particularly noticeable in those areas near the skin of the head, face, neck and chest. This skin dilation cause more blood to circulate in order to radiate off the heat. The sweat glands then release sweat to cool the body off even more. Once the blood vessels return to normal size, the sufferer feels cool again.

Around 85% of women suffer hot flashes during the years immediately before and after menopause, which occurs on average around the age of 51. Hot flashes can begin as early as 2 to 3 years prior to the last menstrual period, however. The hot flashes can last up to six months or go as long as after 15 years after the last menstrual period. On average, the hot flashes continue for two years. The frequency of episodes varies widely, from a few episodes a year to up to 20 episodes a day. Men can also have hot flashes if their levels of the male sex hormone testosterone drop suddenly and dramatically.

Both men and women can suffer from hot flashes as a side effect of cancer therapy. Certain drugs such as Tamoxifen (Nolvadex), which is used to treat breast cancer, as well as Lupron (Leuprolide) and Zoladex (Goserelin), which are employed in the therapy of prostate cancer, can lead to heat sensations. Bilateral orchiectomy for prostate cancer or testicular cancer also affects the hormone system so that patients can subsequently suffer from hot flashes. Especially in the case of cancer patients, hormone replacement therapy is often not advised, because there is a concern that cancer regrowth can be stimulated.

Symptoms that mimic hot flashes can occur in both men and women who have a tumor of the hypothalamus or pituitary gland, as well as with those who have suffered from certain serious infections, such as tuberculosis or HIV, those with alcoholism or those who suffer from thyroid disorders. Symptoms that are similar to hot flashes also can be a side effect of the food additive monosodium glutamate (MSG), or of certain medications, particularly nitroglycerin, nifedipine, niacin, vancomycin and calcitonin.

Most commonly, Hormone Replacement Therapy (HRT) is believed to be one of the most effective treatments available to reduce the onset of hot flashes. These hormones can be taken orally, intravenously, transdermally and/or topically, applied in a cream. However HRT has been associated with increased risk of heart disease as well as certain kinds of cancers.

In addition to hrt and the other medications noted above, several nonprescription dietary supplements or herbal remedies have been promoted as natural ways to prevent or treat hot flashes. A range of "natural" therapies on a herbal basis including black cohosh, phytoestrogens, flax seed, red clover, vitamin E (D. L. Barton et al., J. Clin. Oncol. 1998, 16: 495-500), ginseng and evening primrose oil have been advocated as possible medications (University of Wisconsin Medical School, online courses, "Alternatives for Menopausal Symptoms: A Review of the Evidence"; www.cme.wisc.edu/online/menopause). However, not all of these therapies are effective (K. I. Pritchard, The Oncologist, 2001, 6(4), 353-362).

Alternative medications to help decrease the intensity of hot flashes include clonidine, lofexidine, methyldopa and sertraline. Other medications, which have been suggested, are selective serotonin reuptake inhibitors (SSRIs) such as fluoxetine hydrochloride (Prozac; C. Loprinzi; www.medicine-news.com/articles/pharma/misc/hotflash-es.html) and paroxetine hydrochloride (Paxil; V. Stearns et al., Ann. Oncol., 2000, 11:17-22) as well as venlafaxine hydrochloride (Effexor; C. L. Loprinzi et al., J. Clin. Oncol., 1998, 16: 2377-2381), which is a serotonin and norepinephrine reuptake inhibitor.

Low doses of megestrol acetate have also been shown to reduce the frequency of hot flashes in both men and women (Loprinzi et al., N. Engl. J. Med. 1994, 331:347-351).

Chronic adrenal insufficiency and weight gain can be side effects. Transdermal clonidine has also been employed to reduce the frequency and severity of hot flashes (R. M. Goldberg et al., J. Clin. Onc. 1994, 12:155-158); R. M. Goldberg et al., J. Clin. Oncol. 1994, 12:155-158; L. R. Laufer, Obstet. Gynecol. 1982, 60:583-586). However, side effects such as drowsiness, fatigue, and symptoms of low blood pressure in some patients were observed.

A variety of treatments addressing hot flashes have been proposed. For example, US Publication No. 2004/0092519 to Pharmacia & Upjohn describes methods of treating or preventing hot flashes by administering effective dose of a compound selected from reboxetine, S,S-reboxetine, pharmaceutically acceptable salts thereof, derivatives thereof, or prodrugs thereof. U.S. Pat. No. 6,165,504 to Barr Labs describes methods for treating hot flashes and improving the quality of life of castrated prostatic cancer patients by administration of cyproterone acetate. US Publication No. 2004/0152733 describes the use of duloxetine for treatment of hot flashes. US Publication No. 2004/0092519 describes the use of reboxetine for treatment of symptoms of hormonal variation such as hot flashes. U.S. Pat. No. 6,395,757 describes administration of glycopyrrolate analogs for treating hot flashes. US Publication No. 2007/0281997 describes treatment of hot flashes in subject with prostate disorder such as prostate cancer being managed with androgen deprivation therapy using muscarinic receptor antagonists. US Publication No. 2007/0015786 describes treatment of hot flashes, impulse control disorders and personality change due to a general medical condition using selective norepinephrine reuptake inhibitors e.g. atomoxetine and racemic reboxetine. US Publication No. 2002/0016283 describes a method of treating symptoms of hormonal variation, including hot flashes, using tachykinin receptor antagonist. U.S. Pat. No. 6,310,098 describes a method of treating symptoms of hormonal variation including hot flashes by administration of a compound which is a ligand of the alpha-2-delta subunit of a voltage-gated calcium channel.

However, new treatments for prevention or reduction of symptoms associated with such endocrine disturbances are needed.

SUMMARY

It was surprisingly found that certain tricyclic amino containing compounds are effective in reducing symptoms associated with endocrine disturbances, and in particular with those associated with altered or reduced estrogen and progesterone levels. Methods for the treatment or prevention of endocrine disturbances are thus provided, in particular the reduction of symptoms of endocrine disturbances such as hot flashes associated with menopause or chemotherapy by treating a host in need thereof. Generally, methods of treating or preventing symptoms associated with endocrine disturbances in a host are provided that include administering a compound as described herein to the host.

In certain embodiments, the disclosure relates to methods of treating or preventing hot flashes comprising administering to a subject diagnosed with, exhibiting symtoms, or at risk of changing hormone levels a pharmaceutical composition comprising a compound disclosed herein. In further embodiments, the subject is menopausal or perimenopausal woman or the subject is menstruating or expecting to menstruate with a week or the subject is a woman diagnosed with vulvodynia. In certain embodiments, the subject is a man diagnosed with prostate cancer.

In certain embodiments, the pharmaceutical composition is administered in combination with another active agent such as an agonist or antagonist of an estrogen receptor or tamoxifen or an antiandrogen or spironolactone, cyproterone, flutamide, nilutamide, bicalutamide, finasteride, or dutasteride.

In certain embodiments, the compound is MSX-122, i.e., N-(4-((pyrimidin-2-ylamino) methyl) benzyl)-pyrimidin-2-amine or pharmaceutically acceptable salt thereof. In certain embodiments, the disclosure relates to the use of a compound disclosed herein in the production of a medicament for the treatment or prevention of hot flashes.

In particular embodiments, the host is suffering from a reduction in estrogen levels due to menopause. In other embodiments, the host is suffering from endocrine disturbances due to administration of a drug, and in particular due to administration of a chemotherapeutic agent. In further embodiments, the host is suffering from an endocrine disorder such as an autoimmune endocrine disease. In specific embodiments, the host is suffering from Graves disease.

In one embodiment, the disclosure relates to methods for the treatment or prevention of symptoms associated with endocrine disturbances, and in particular for the treatment or prevention of hot flashes is provided that includes administering a compound of Formula I, or a pharmaceutically acceptable salt, ester or prodrug thereof to a host in need thereof:

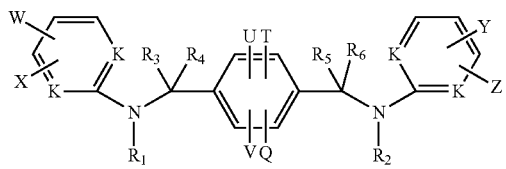

Formula I wherein
each K is independently N or CH;
Q, T, U, V, W, X, Y and Z are independently selected from H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, where R and R' are independently selected from straight chain, branched or cyclic alkyl or aralkyl groups, as well as aryl and heteroaryl groups; and $R_1$, $R_2$, $R_3$, $R_4$, $R_5$ and $R_6$ are independently selected from H, straight chain, branched or cyclic alkyl, aralkyl, aryl heteroaryl, acyl (R(O=C)— and imidoyl (R(NH=C)— or R(NR'=)C—) groups.

Additional compounds of Formula II-VII are provided herein for the treatment or prevention of symptoms associated with endocrine disturbances, and in particular for the treatment or prevention of hot flashes.

In one particular embodiment, a method for the treatment or prevention of symptoms associated with endocrine disturbances, and in particular for the treatment or prevention of hot flashes is provided including administering a compound of Formula XVI, or a pharmaceutically acceptable salt, ester or prodrug thereof to a host in need thereof:

Formula XVI

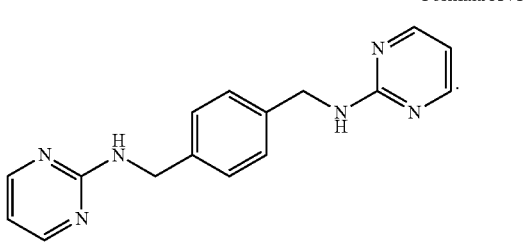

Typically, the compounds or compositions are administered to a host at risk of an endocrine disturbance. In certain embodiments, the host is a premenopausal or menopausal female. In other embodiments, the host is suffering from an endocrine disease. In yet other embodiments, the host has received a drug treatment, and in particular a chemotherapy treatment within 10 days or within 9 days, or within 8 days or within 7 days, or within 6 days, or within 5 days or within 4 days, or within 3 days, or within 2 days or within one day or less of receiving the compound or composition described herein.

In some embodiments, pharmaceutical compositions or methods include at least one compound of Formulas (I)-(XVII) in combination or alternation with at least a second active compound. The second active compound can be a chemotherapeutic, particularly an agent active against a primary tumor. In other embodiments, the second agent is a hormone replacement or hormone supplement. In further embodiments, the second agent is an estrogen receptor agonist.

In certain embodiments, treatment methods disclosed herein contemplate administering a pharmaceutical composition comprising a compound disclosed herein to the subject after, before, or during a surgery selected from a hysterectomy, oophorectomy, partial oophorectomy, unilateral salpingo-oophorectomy, bilateral salpingo-oophorectomy or combination thereof.

DETAILED DESCRIPTION OF THE DISCLOSURE

Pharmaceutical compositions and methods for the treatment or prevention of endocrine disturbances are provided, and in particular with those associated with altered or reduced estrogen and progesterone levels such as those resulting in the symptoms of hot flashes. The inventors have found that certain compounds described herein can prevent or reduce these symptoms.

The compounds described herein were previously identified as chemokine receptor modulators. Chemokines are a superfamily of small cytokines that induce, through their interaction with G-protein-coupled receptors, cytoskeletal rearrangements and directional migration of several cell types. These secreted proteins act in a coordinated fashion with cell-surface proteins to direct the homing of various subsets of cells to specific anatomical sites (Morales, et al. (1999) Proc Natl Acad Sci USA 96: 14470-14475; Homey, B., et al. (2000) J Immunol 164: 3465-3470; Peled, et al. (1999) Science 283: 845-848; Forster, et al. (1999) Cell 99: 23-33).

Chemokines are considered to be principal mediators in the initiation and maintenance of inflammation. They have also been found to play an important role in the regulation of endothelial cell function, including proliferation, migration and differentiation during angiogenesis and re-endothelialization after injury (Gupta et al. (1998) J Biol Chem, 7:4282-4287).

The chemokine receptor, CXCR4, is known in viral research as a major coreceptor for the entry of T cell line-tropic HIV (Feng, et al. (1996) Science 272: 872-877; Davis, et al. (1997) J Exp Med 186: 1793-1798; Zaitseva, et al. (1997) Nat Med 3: 1369-1375; Sanchez, et al. (1997) J Biol Chem 272: 27529-27531). T Stromal cell derived factor 1 (SDF-1) is a chemokine that interacts specifically with CXCR4. When SDF-1 binds to CXCR4, CXCR4 activates Gal-protein-mediated signaling (pertussis toxin-sensitive), including downstream kinase pathways such as Ras/MAP Kinases and phosphatidylinositol 3-kinase (PI3K)/Akt in lymphocyte, megakaryocytes, and hematopoietic stem cells (Bleul, et al. (1996) Nature 382: 829-833; Deng, et al. (1997) Nature 388: 296-300; Kijowski, et al. (2001) Stem Cells 19: 453-466; Majka, et al. (2001) Folia. Histochem. Cytobiol. 39: 235-244; Sotsios, et al. (1999) J. Immunol. 163: 5954-5963; Vlahakis, et al. (2002) J. Immunol. 169: 5546-5554).

Compounds targeting CXCR4 have been developed primarily for treatment of HIV because CXCR4 is a major coreceptor for T-tropic HIV infection. Peptide antagonists of CXCR4 receptors have been disclosed. Tamamura et al reported the identification of a specific peptide-based CXCR4 inhibitor, T140. T140 is a 14-residue peptide that possesses anti-HIV activity and antagonism of T cell line-tropic HIV-1 entry among all antagonists of CXCR4 (Tamamura, et al. (1998) Biochem. Biophys. Res. Commun. 253: 877-882). Other peptide-based antagonists have also been disclosed. For example, European Patent Publication Nos. 1 286 684 and 1 061 944 to the University Of British Columbia cover methods of treatment of diseases, including metastasis, using modified peptide CXCR4 antagonists derived from the native SDF-1 ligand. PCT Publication No. WO 04/020462 to Takeda Chemical Industries, Ltd. provides peptide CXCR4 antagonists for treatment and prevention of breast cancer and chronic rheumatoid arthritis. U.S. Patent Application No. 2004/0132642 to the U.S. Dept. of Health & Human Services in part covers methods of inhibiting metastasis or growth of a tumor cell with a polypeptide CXCR4 inhibitor. Additionally, the metal-chelating cyclams and bicyclams represent one of the few reported non-peptide molecules to effectively block CXCR4 (Onuffer and Horuk (2002) Trends Pharmacol Sci 23: 459-467.36). One of these non-peptide molecules is AMD3100, which entered clinical trials as an anti-HIV drug that blocks CXCR4-mediated viral entry (Donzella, et al. (1998) Nat Med 4: 72-77; Hatse, et al. (2002) FEBS Lett 527: 255-262; Fujii, et al. (2003) Expert Opin Investig Drugs 12: 185-195; Schols, et al. (1997) Antiviral Res 35: 147-156).

Other nitrogen containing bicyclic molecules have been developed as CXCR4 antagonists. European Patent Publication No. 1 431 290 and PCT Publication No. WO 02/094261 to Kureha Chemical Industry Co., Ltd cover CXCR4 inhibitors that are potentially useful in treating various diseases including cancer metastatic disease. Additionally, certain compounds are described as CXCR4 inhibitors in U.S. Patent Publication No. 2004/0254221 to Yamamazi, et al., PCT Publication Nos. WO 00/5672, 04/091518, 04/093817 and 04/106493, all to AnorMED, which describe these compounds as inhibitors of CXCR4 and/or CCR5 receptors and suggest that these are active as antivirals, particularly against infections of target cells by a human immunodeficiency virus (HIV), cancers, with blood cell production and certain inflammatory conditions.

U.S. Patent Publication No. 2007/0054930 to Shim, et al. provides certain compounds that are CXCR4 inhibitors for the treatment of proliferative conditions mediated by CXCR4 receptors, particularly for metastasis.

Active Compound, and Physiologically Acceptable Salts and Prodrugs Thereof

In a first principal embodiment, a compound of Formula I, or a pharmaceutically acceptable salt, ester or prodrug thereof, is provided:

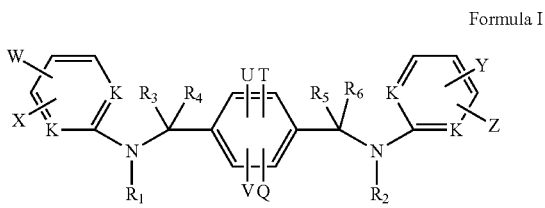

Formula I wherein
each K is independently N or CH;
Q, T, U, V, W, X, Y and Z are independently selected from H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, where R and R' are independently selected from straight chain, branched or cyclic alkyl or aralkyl groups, as well as aryl and heteroaryl groups; and $R_1$, $R_2$, $R_3$, $R_4$, $R_5$ and $R_6$ are independently selected from H, straight chain, branched or cyclic alkyl, aralkyl, aryl heteroaryl, acyl (R(O=C)— and imidoyl (R(NH=C)— or R(NR'=)C—) groups.

In one subembodiment of Formula I, Y and Z are each hydrogen. Alternatively, W and X are each hydrogen. In yet another subembodiment, W, X, Y and Z are all hydrogen.

Zou et al. (Zou, et al. (2003) *Acta Cryst*. E59: online 1312-o1313) described the synthesis of a potentially tetradentate ligand, 1,4-bis-(pyridine-2-aminomethyl)benzene. Zou described this compound as a potential ligand for metal ions.

In a subembodiment, a compound of Formula I-1 to I-10, or a pharmaceutically acceptable salt, ester or prodrug thereof, is provided:

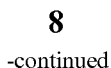

(I-1)

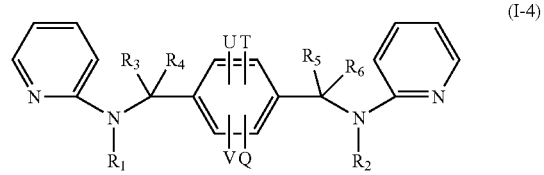

(I-2)

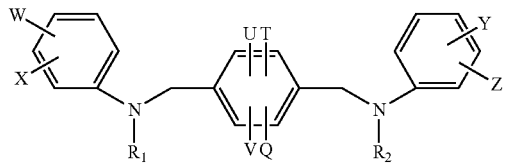

(I-3)

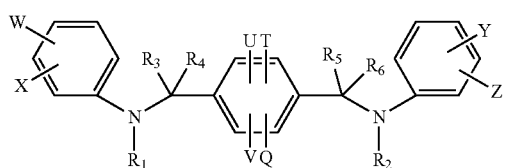

(I-4)

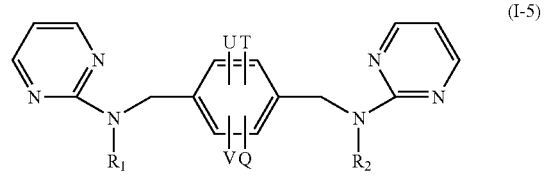

(I-5)

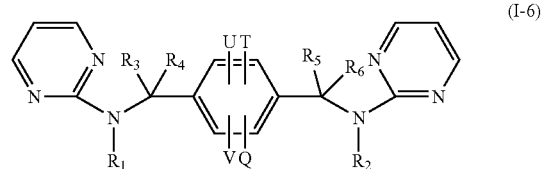

(I-6)

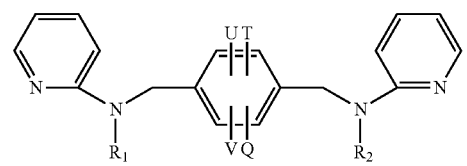

(I-7)

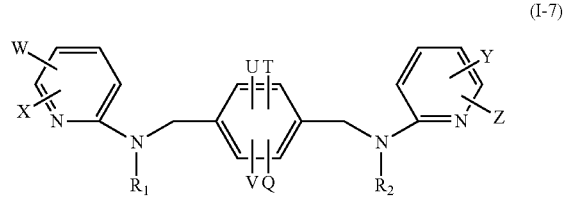

(I-8)

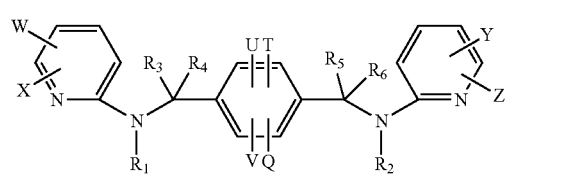

(I-9)

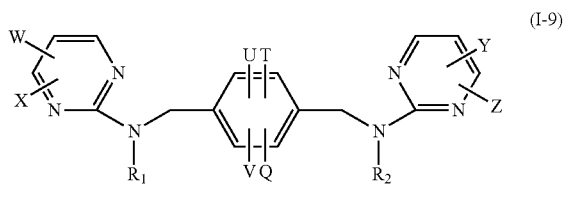

(I-10)

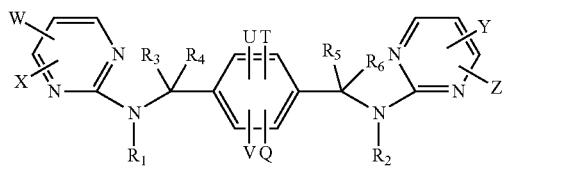

wherein
Q, T, U, V, W, X, Y and Z are as defined above; and
$R_1$, $R_2$, $R_3$, $R_4$, $R_5$ and $R_6$ are as defined above.

In another sub-embodiment, a compound of Formula I-11 to 1-20, or a pharmaceutically acceptable salt, ester or prodrug, is provided:

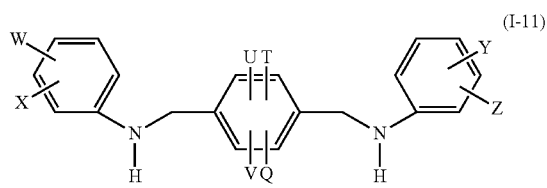
(I-11)

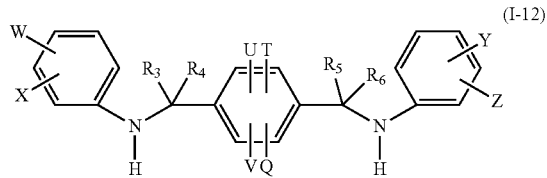
(I-12)

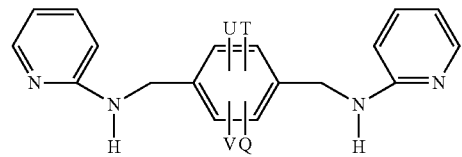
(I-13)

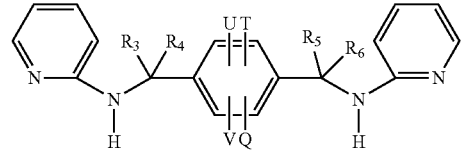
(I-14)

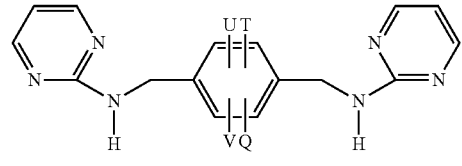
(I-15)

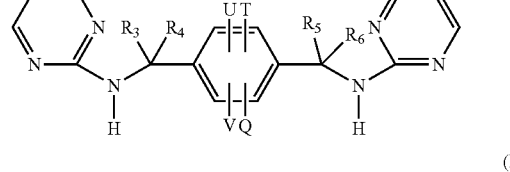
(I-16)

(I-17)

(I-18)

(I-19)

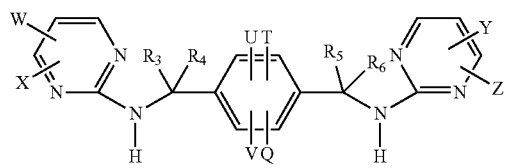
(I-20)

wherein
Q, T, U, V, W, X, Y and Z are as defined above; and
$R_1$, $R_2$, $R_3$, $R_4$, $R_5$ and $R_6$ are as defined above.

In a second principal embodiment, the disclosure provides a compound of Formula IIa or IIb, or a pharmaceutically acceptable salt, ester or prodrug thereof:

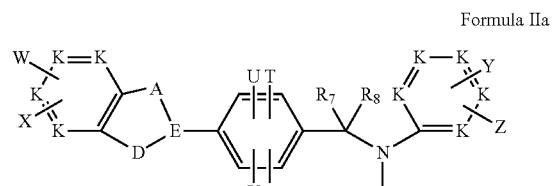
Formula IIa

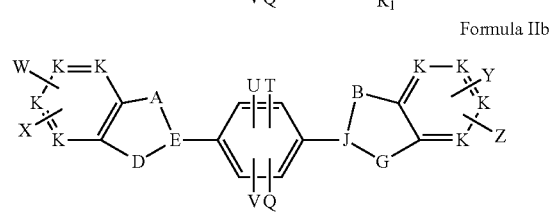
Formula IIb wherein
each K is independently N or CH;
Q, T, U, V, W, X, Y and Z are as defined above;
A and B are one and two atom tethers independently selected from —CR═, —CR3R4-, —CR3═, —N═, —O—, —NR$_3$—, —S—, —CR$_3$═CR$_4$—, —CR$_3$R$_4$—CR$_5$R$_6$—, —CR$_3$═N—, —CR$_3$R$_4$—NR$_5$—, —N═CR$_3$—, and —NR$_3$—CR$_4$R$_5$—;
-D-E- and -G-J- are independently either —NR$_3$—CR$_4$— or —N═C—; and
$R_1$, $R_2$, $R_3$, $R_4$, $R_5$, $R_6$, $R_7$ and $R_8$ are independently selected from H, straight chain, branched or cyclic alkyl, aralkyl, aryl heteroaryl acyl (R(O═C)— and imidoyl (R(NH═C)— or R(NR'═)C—) groups.

In one subembodiment of Formula II, Y and Z are each hydrogen. Alternatively, W and X are each hydrogen. In yet another subembodiment, W, X, Y and Z are all hydrogen.

In a subembodiment, the disclosure provides a compound of Formula II-1 to II-18, or a pharmaceutically acceptable salt, ester or prodrug thereof:

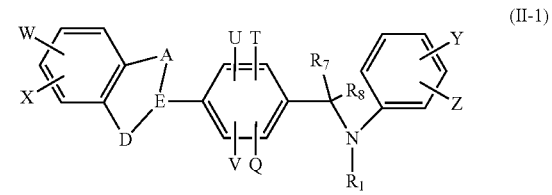
(II-1)

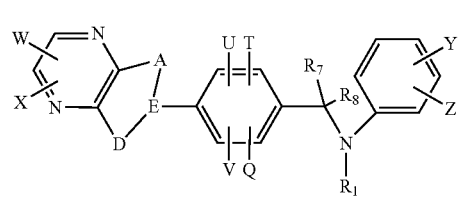
(II-2)
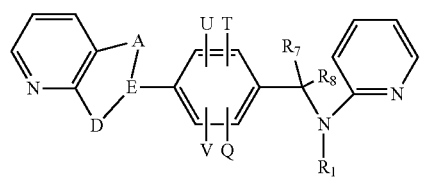
(II-3)
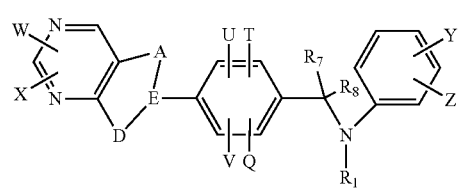
(II-4)
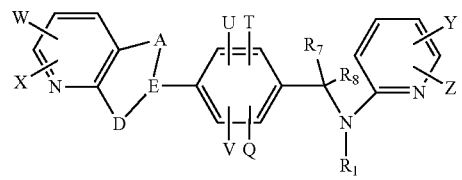
(II-5)
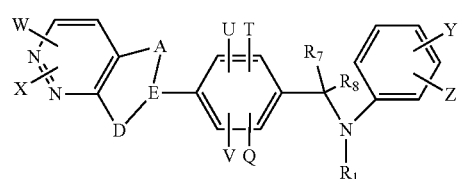
(II-6)
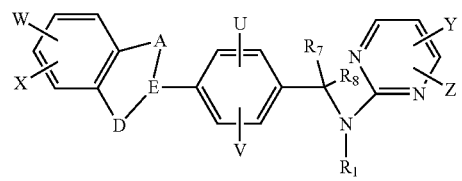
(II-7)
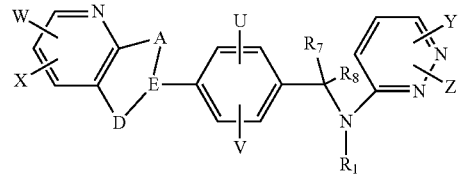
(II-8)
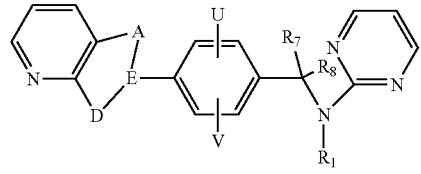
(II-9)
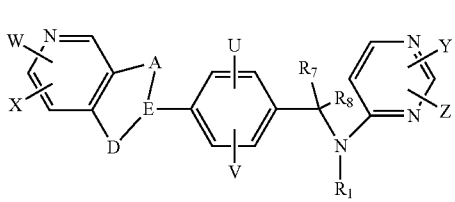
(II-10)
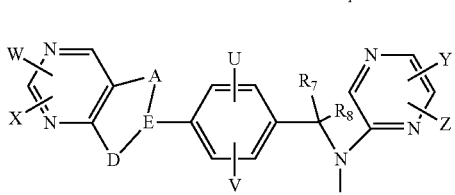
(II-11)
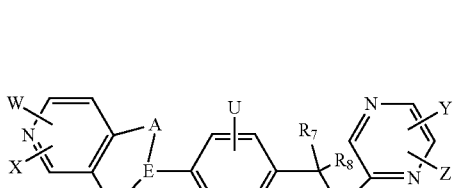
(II-12)
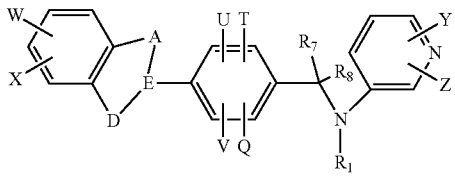
(II-13)
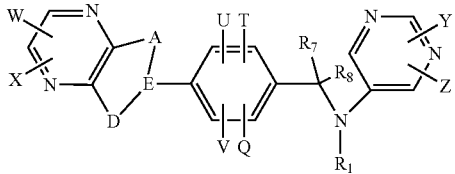
(II-14)
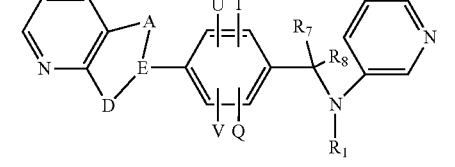
(II-15)
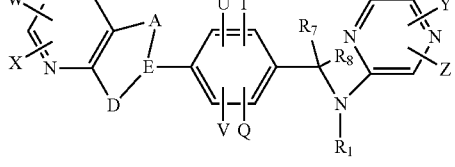
(II-16)
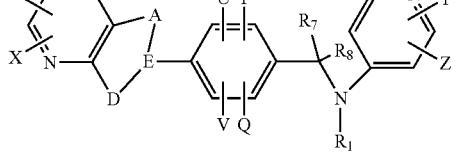
(II-17)

-continued

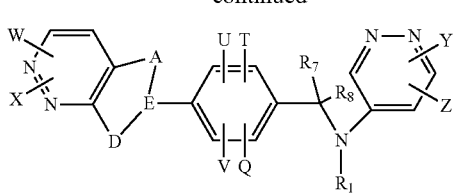
(II-18)

wherein
Q, T, U, V, W, X, Y and Z are as defined above;
A and -D-E- are as defined above; and
R₁, R₂, R₃, R₄, R₅, R₆, R₇ and R₈ are as defined above.

In another subembodiment, the disclosure provides a compound of Formula II-19 through 11-30, or a pharmaceutically acceptable salt, ester or prodrug thereof:

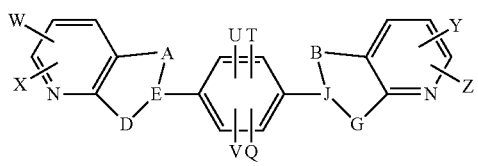
(II-19)

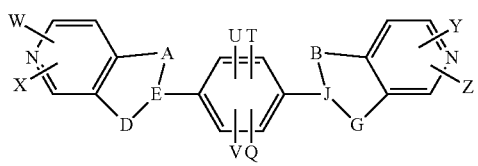
(II-20)

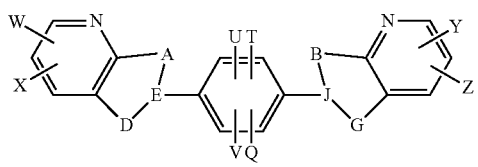
(II-21)

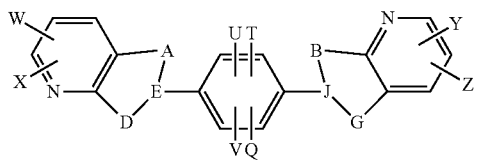
(II-22)

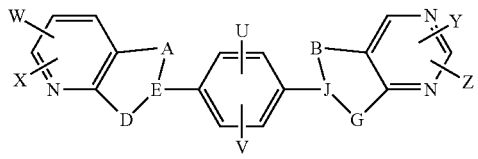
(II-23)

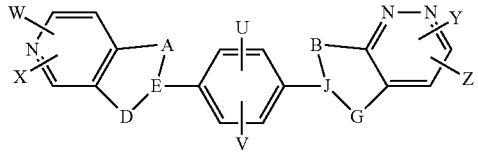
(II-24)

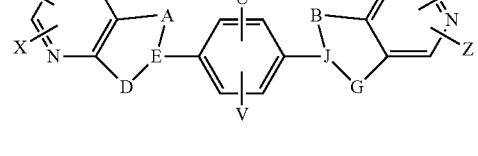
(II-51)

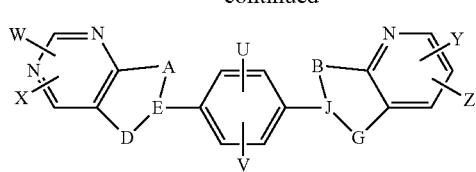
(II-26)

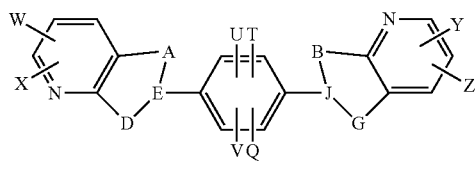
(II-27)

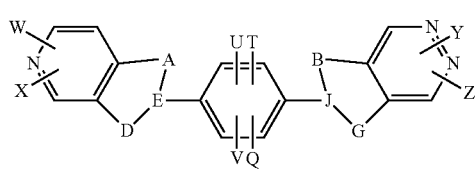
(II-28)

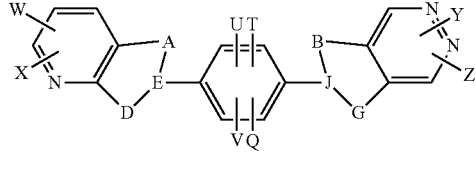
(II-29)

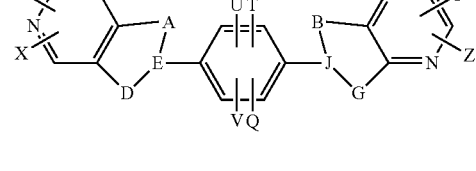
(II-30)

wherein
Q, T, U, V, W, X, Y and Z are as defined above;
A, B, -D-E- and -G-J- are as defined above; and
R₁, R₂, R₃, R₄, R₅, R₆, R₇ and R₈ are as defined above.

In a third principal embodiment, a compound of Formula III, or a pharmaceutically acceptable salt, ester or prodrug thereof:

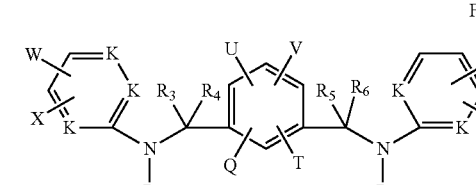
Formula III wherein
each K is independently N or CH;
Q, T, U, V, W, X, Y and Z are as defined above; and
R₁, R₂, R₃, R₄, R₅ and R₆ are as defined above.

In one subembodiment of Formula III, Y and Z are each hydrogen. Alternatively, W and X are each hydrogen. In yet another subembodiment, W, X, Y and Z are all hydrogen.

Reyes et al. (Reyes, et al. (2002) *Tetrahedron* 58:8573-8579) described the synthesis of certain polyamines from starting pyridinium N-aminides. No specific functions were attributed to these compounds.

In a subembodiment, a compound of Formula III-1 through III-10, or a pharmaceutically acceptable salt, ester or prodrug thereof, is provided:

(III-1)
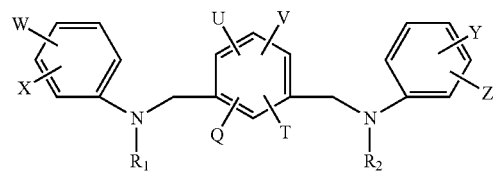

(III-2)
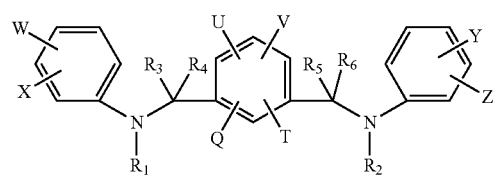

(III-3)
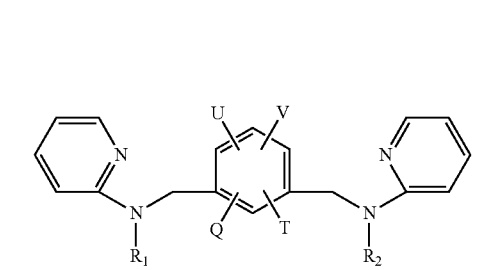

(III-4)
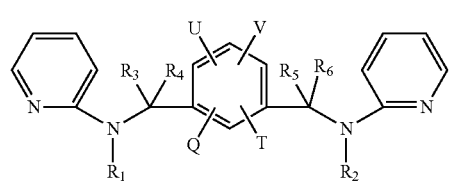

(III-5)
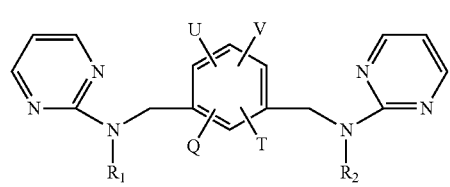

(III-6)
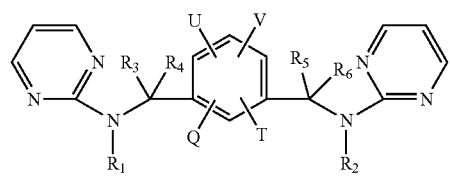

(III-7)
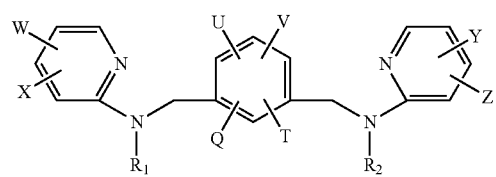

-continued (III-8)
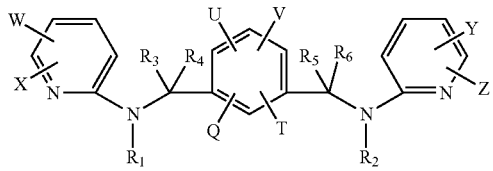

(III-9)
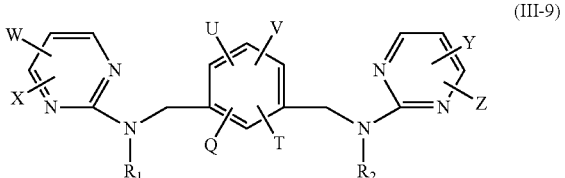

(III-10)
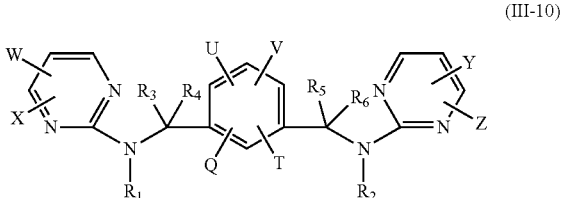

wherein

Q, T, U, V, W, X, Y and Z are as defined above; and $R_1$, $R_2$, $R_3$, $R_4$, $R_5$ and $R_6$ are as defined above.

In another subembodiment, a compound of Formula III-11 through III-20, or a pharmaceutically acceptable salt, ester or prodrug thereof, is provided:

(III-11)
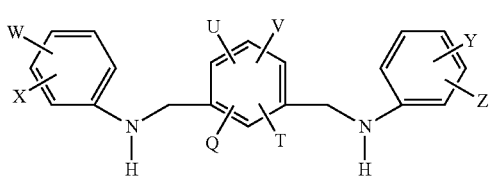

(III-12)
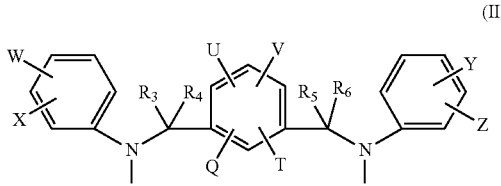

(III-13)
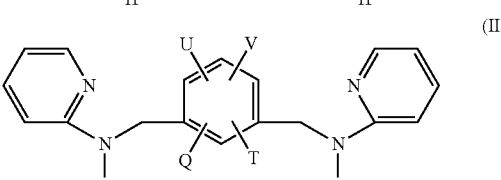

(III-14)
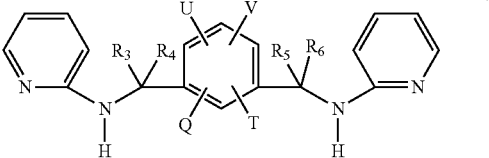

-continued (III-15)
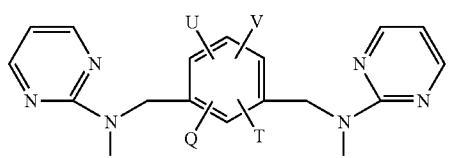

(III-16)
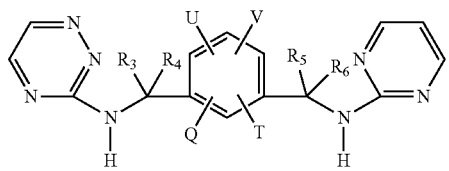

(III-17)
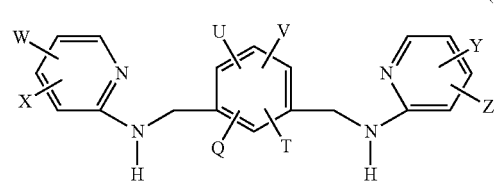

(III-18)
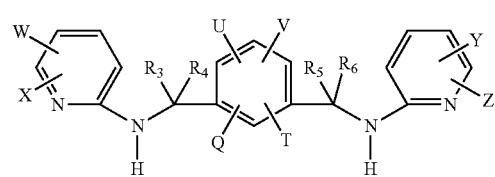

(III-19)
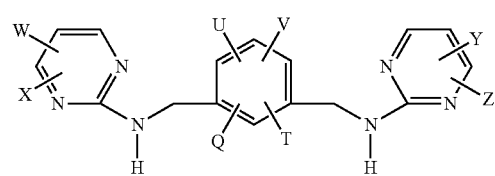

(III-20)
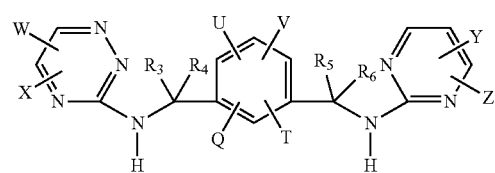

wherein

Q, T, U, V, W, X, Y and Z are as defined above; and $R_1$, $R_2$, $R_3$, $R_4$, $R_5$ and $R_6$ are as defined above.

In an fourth principal embodiment, the disclosure provides a compound of Formula IVa or IVb, or a pharmaceutically acceptable salt, ester or prodrug thereof:

Formula IVa
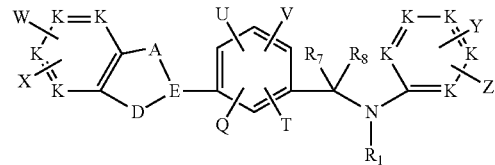

Formula IVb
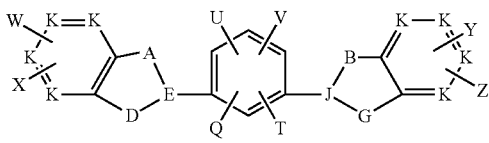

wherein each K is independently N or CH;

Q, T, U, V, W, X, Y and Z are as defined above;

$R_1$, $R_2$, $R_3$, $R_4$, $R_5$, $R_6$, $R_7$ and $R_8$ are as defined above; and A and B and -D-E- and -G-J- are as defined above.

In one subembodiment of Formula IVa or IVb, Y and Z are each hydrogen. Alternatively, W and X are each hydrogen. In yet another subembodiment, W, X, Y and Z are all hydrogen.

In one subembodiment, the disclosure provides a compound of Formula IV-1 to IV-12, or a pharmaceutically acceptable salt, ester or prodrug thereof:

(IV-1)
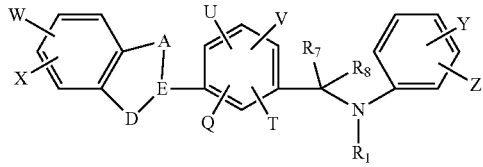

(IV-2)
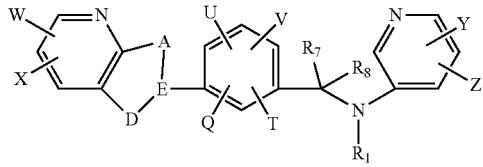

(IV-3)
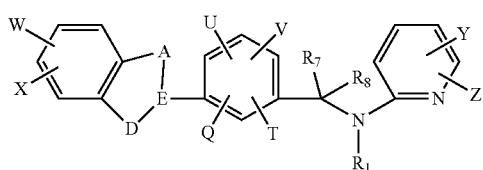

(IV-4)
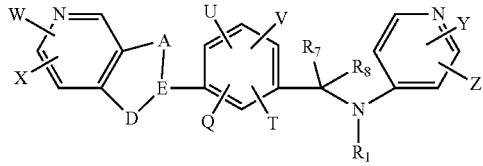

(IV-5)
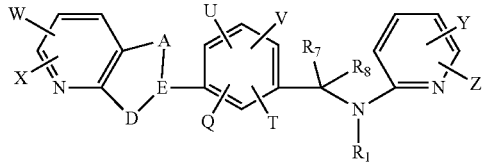

-continued

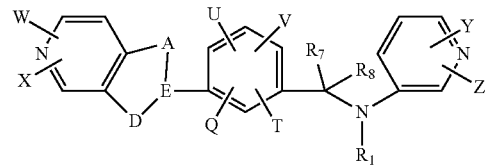
(IV-6)

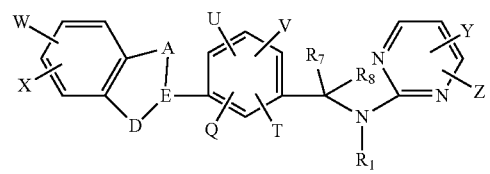
(IV-7)

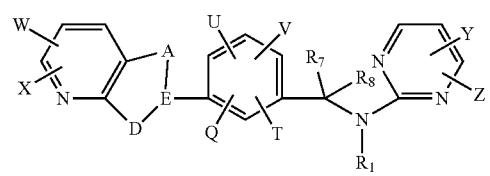
(IV-8)

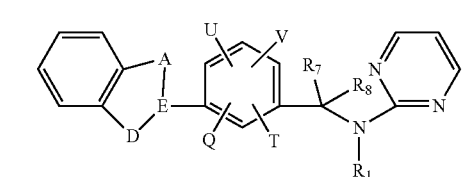
(IV-9)

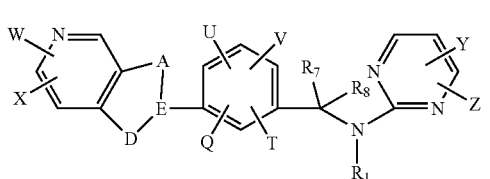
(IV-10)

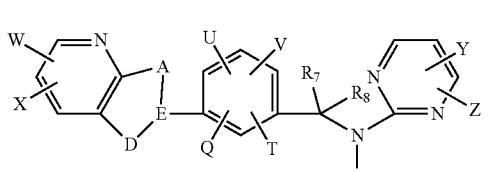
(IV-11)

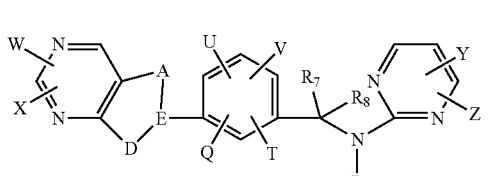
(IV-12)

wherein

Q, T, U, V, W, X, Y and Z are as defined above;

$R_1$, $R_2$, $R_3$, $R_4$, $R_5$, $R_6$, $R_7$ and $R_8$ are as defined above; and A and -D-E- are as defined above.

In another subembodiment, compounds of the Formula IV-13 to IV-20, or a pharmaceutically acceptable salt, ester or prodrug thereof, are provided:

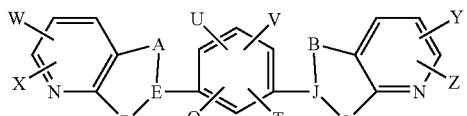
(IV-13)

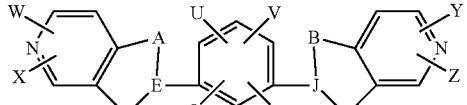
(IV-14)

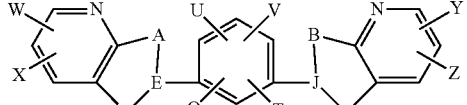
(IV-15)

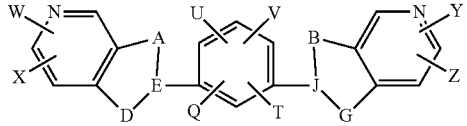
(IV-16)

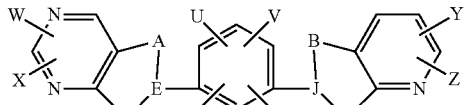
(IV-17)

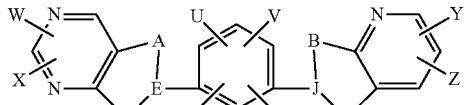
(IV-18)

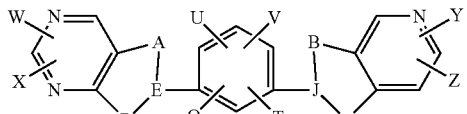
(IV-19)

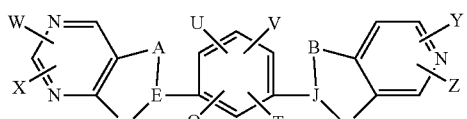
(IV-20)

wherein

Q, T, U, V, W, X, Y and Z are as defined above;

$R_2$, $R_3$, $R_4$, $R_5$, $R_6$, $R_7$ and $R_8$ are as defined above; and

A, B, -D-E- and -G-J- are as defined above.

In an fifth principal embodiment, a compound of Formula Va, Vb, or Vc or a pharmaceutically acceptable salt, ester or prodrug thereof, is provided:

Formula Va

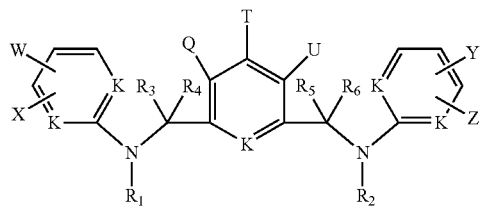

Formula Vb

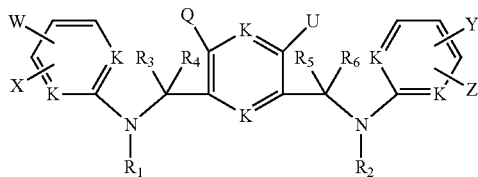

Formula Vc

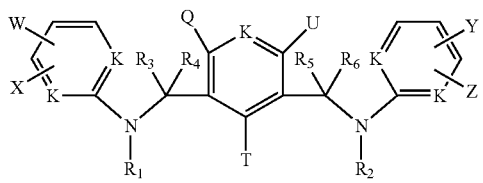

wherein
each K is independently N or CH;
Q, T, U, W, X, Y and Z are as defined above; and
$R_1$, $R_2$, $R_3$, $R_4$, $R_5$ and $R_6$ are as defined above.

In one subembodiment of Formula Va-c, Y and Z are each hydrogen. Alternatively, W and X are each hydrogen. In yet another subembodiment, W, X, Y and Z are all hydrogen.

In one subembodiment, a compound of Formula V-1 through V-3, or a pharmaceutically acceptable salt, ester or prodrug thereof, is provided:

(V-1)

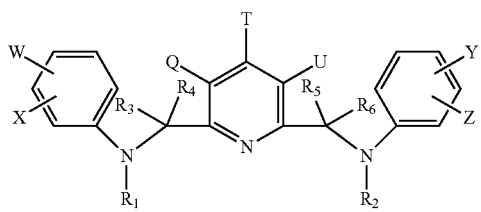

(V-2)

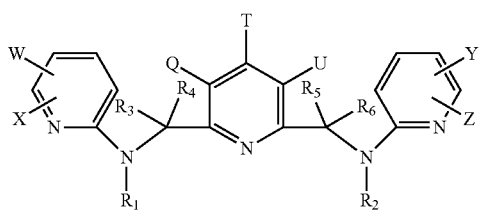

(V-3)

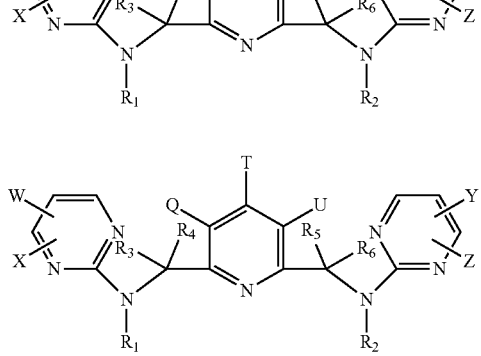

wherein
each K is independently N or CH;
Q, T, U, W, X, Y and Z are as defined above; and
$R_2$, $R_3$, $R_4$, $R_5$ and $R_6$ are as defined above.

In another subembodiment, a compound of Formula V-4 through V-9, or a pharmaceutically acceptable salt, ester or prodrug thereof, is provided:

(V-4)

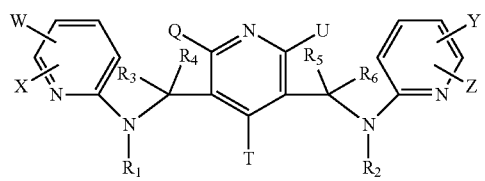

(V-5)

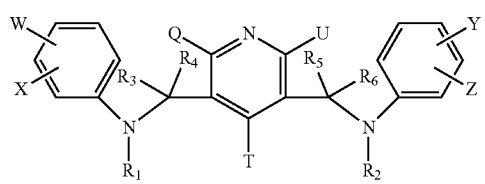

(V-6)

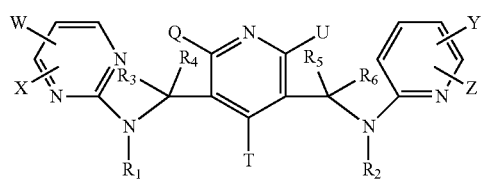

(V-7)

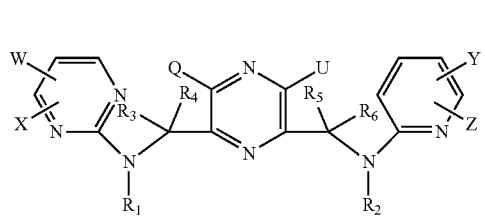

(V-8)

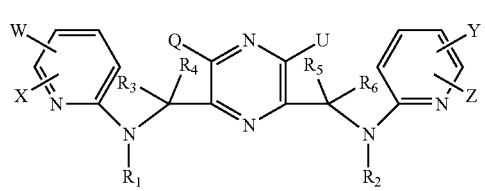

(V-9)

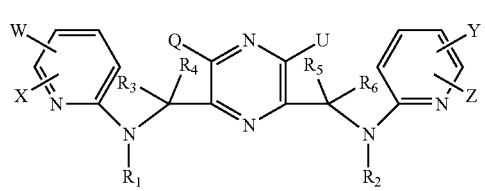

wherein
each K is independently N or CH;
Q, T, U, W, X, Y and Z are as defined above; and
$R_1$, $R_2$, $R_3$, $R_4$, $R_5$ and $R_6$ are as defined above.

In an sixth principal embodiment, the disclosure provides a compound of Formula VIa or VIb, or a pharmaceutically acceptable salt, ester or prodrug thereof:

Formula VIa

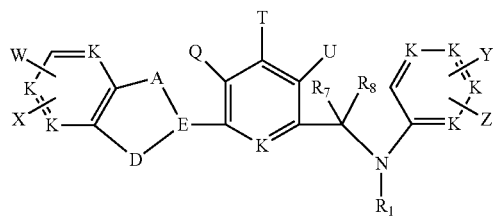

Formula VIb

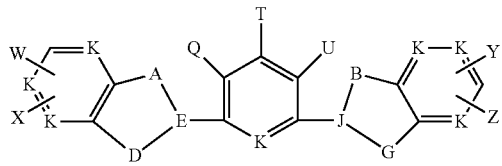

wherein each K is independently N or CH;

Q, T, U, W, X, Y and Z are as defined above;

$R_1, R_2, R_3, R_4, R_5, R_6, R_7$ and $R_8$ are as defined above; and

A and B and -D-E- and -G-J- are as defined above.

In one subembodiment of Formula VIa or b, Y and Z are each hydrogen. Alternatively, W and X are each hydrogen. In yet another subembodiment, W, X, Y and Z are all hydrogen.

In one subembodiment, a compound of Formula VI-1 to VI-6, or a pharmaceutically acceptable salt, ester or prodrug thereof, is provided:

(VI-1)

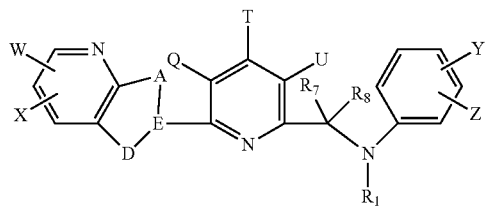

(VI-2)

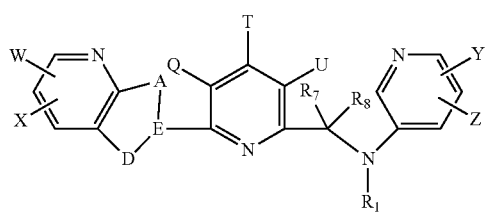

(VI-3)

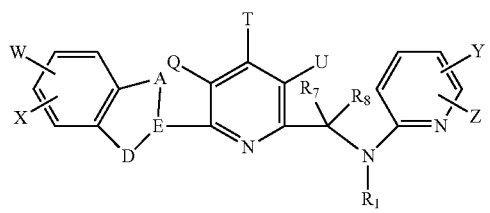

(VI-4)

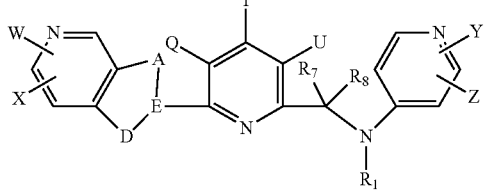

(VI-5)

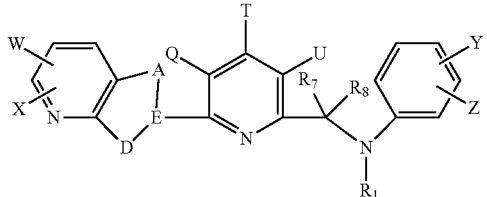

(VI-6)

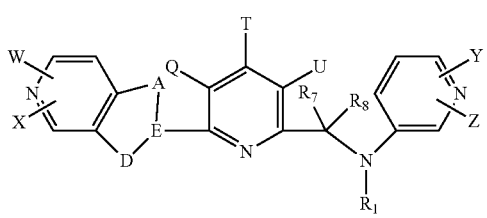

wherein

Q, T, U, W, X, Y and Z are as defined above;

$R_2, R_3, R_4, R_5, R_6, R_7$ and $R_8$ are as defined above; and

A and -D-E- are as defined above.

In another subembodiment, a compound of Formula VI-7 to VI-10, or a pharmaceutically acceptable salt, ester or prodrug thereof, is provided:

(VI-7)

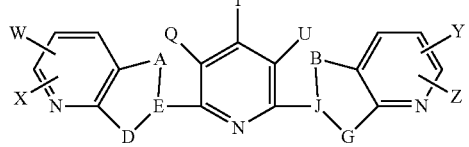

(VI-8)

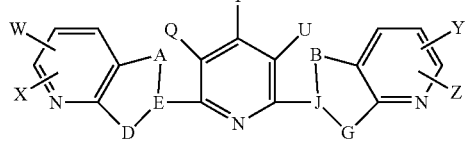

(VI-9)

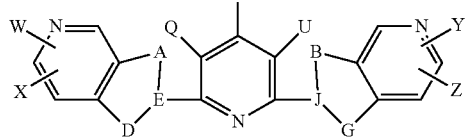

(VI-10)

wherein Q, T, U, W, X, Y and Z are as defined above;

$R_2$, $R_3$, $R_4$, $R_5$, $R_6$, $R_7$ and $R_8$ are as defined above; and

A and B and -D-E- and -G-J- are as defined above.

In an seventh principal embodiment, the disclosure provides a compound of Formula VII, or a pharmaceutically acceptable salt, ester or prodrug thereof:

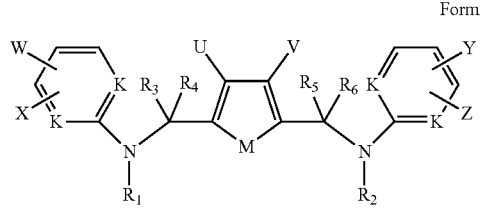

Formula VII wherein each K is independently N or CH;

U, V, W, X, Y and Z are as defined above;

$R_2$, $R_3$, $R_4$, $R_5$ and $R_6$ are as defined above; and

M is O, S or $NR_3$.

In one subembodiment of Formula VII, Y and Z are each hydrogen. Alternatively, W and X are each hydrogen. In yet another subembodiment, W, X, Y and Z are all hydrogen.

In one subembodiment, a compound of Formula VII-1 to VII-10, or a pharmaceutically acceptable salt, ester or prodrug thereof, is provided:

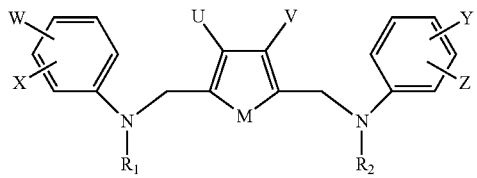
(VII-1)

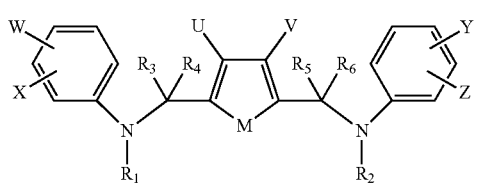
(VII-2)

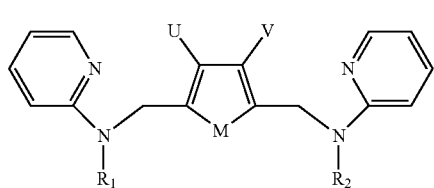
(VII-3)

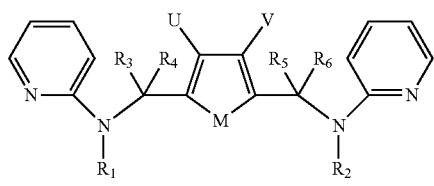
(VII-4)

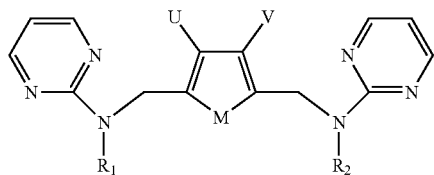
(VII-5)

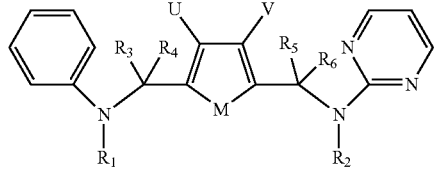
(VII-6)

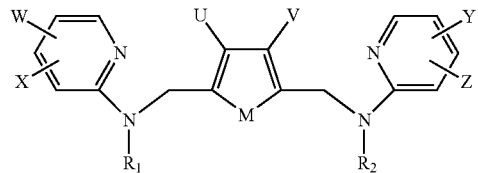
(VII-7)

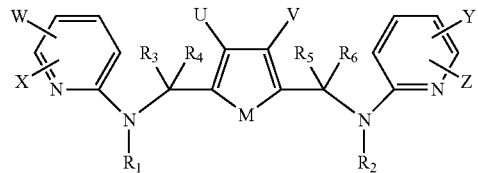
(VII-8)

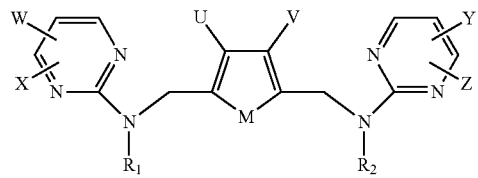
(VII-9)

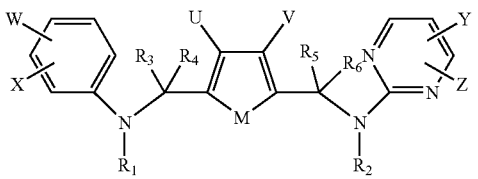
(VII-10)

wherein

U, V, W, X, Y and Z are as defined above;

$R_2$, $R_3$, $R_4$, $R_5$ and $R_6$ are as defined above; and

M is O, S or $NR_3$.

In another subembodiment, a compound of Formula VII-11 to VII-20, or a pharmaceutically acceptable salt, ester or prodrug thereof, is provided:

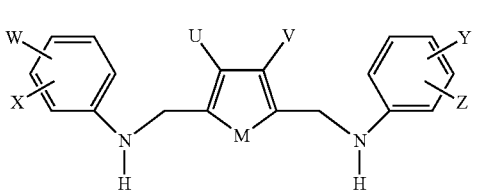
(VII-11)

-continued (VII-12) 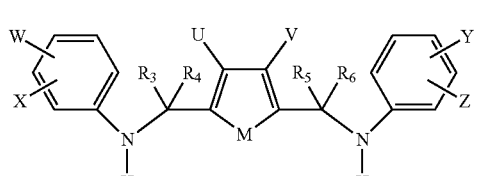

(VII-13) 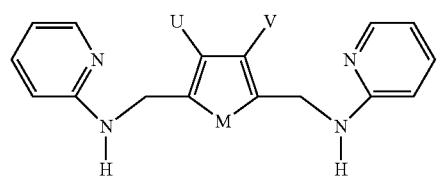

(VII-14) 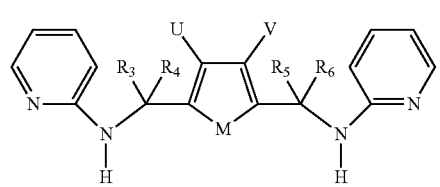

(VII-15) 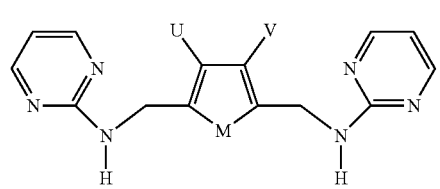

(VII-16) 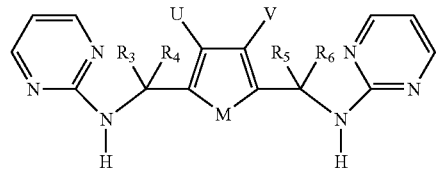

(VII-17) 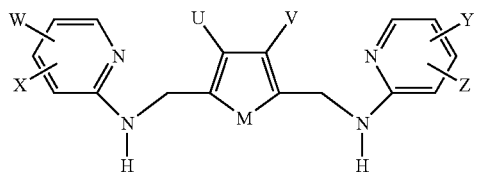

(VII-18) 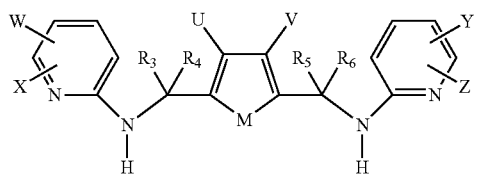

(VII-19) 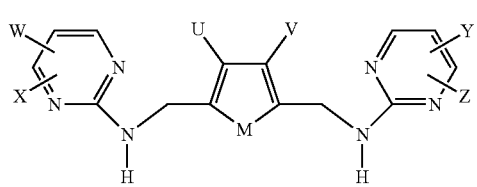

-continued (VII-20) 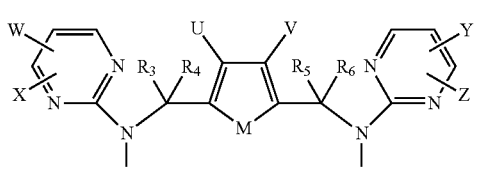

wherein
U, V, W, X, Y and Z are as defined above;
$R_2$, $R_3$, $R_4$, $R_5$ and $R_6$ are as defined above; and
M is O, S or $NR_3$.

In an eight principal embodiment, the disclosure provides a compound of Formula VIIIa or VIIIb, or a pharmaceutically acceptable salt, ester or prodrug thereof:

Formula VIIIa

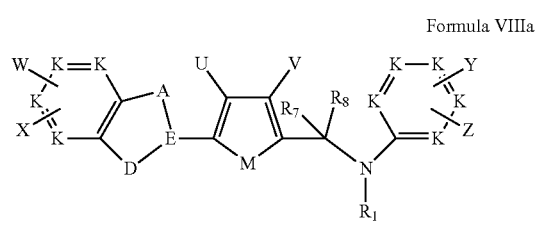

Formula VIIIb

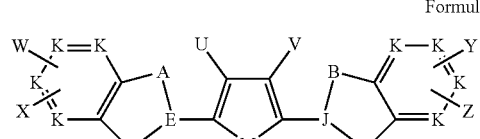

wherein
each K is independently N or CH;
U, V, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above; and
M is O, S or $NR_3$.

In one subembodiment of Formula VIIIa orb, Y and Z are each hydrogen. Alternatively, W and X are each hydrogen. In yet another subembodiment, W, X, Y and Z are all hydrogen.

In a subembodiment, a compound of Formula VIII-1 to VIII-12, or a pharmaceutically acceptable salt, ester or prodrug thereof, is provided:

(VIII-1) 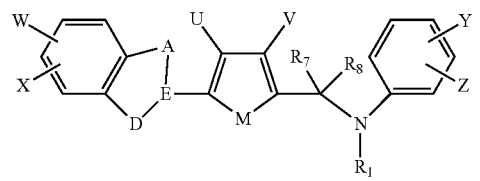

(VIII-2) 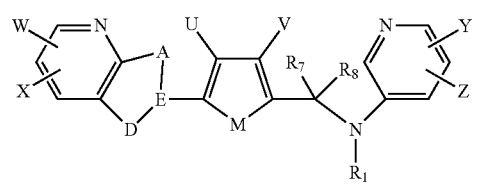

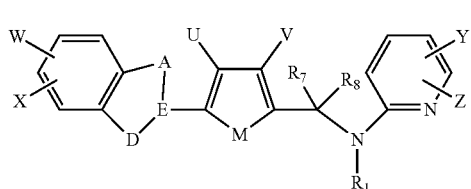 (VIII-3)
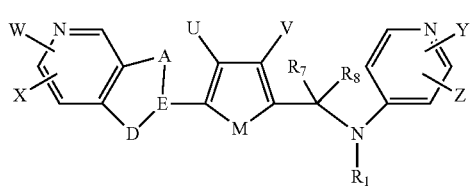 (VIII-4)
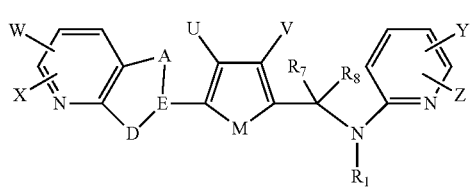 (VIII-5)
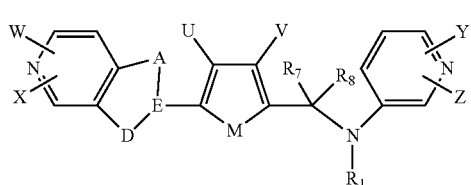 (VIII-6)
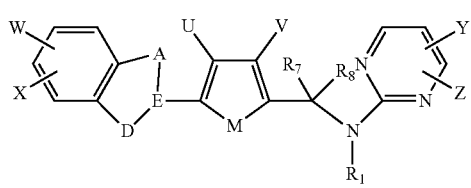 (VIII-7)
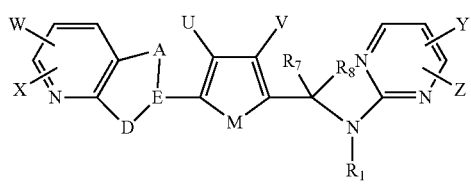 (VIII-8)
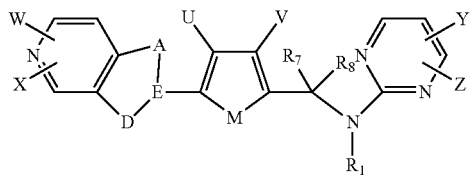 (VIII-9)
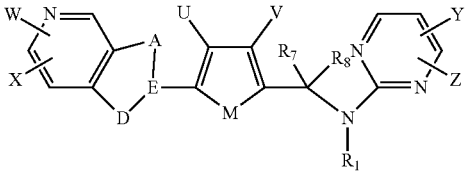 (VIII-10)
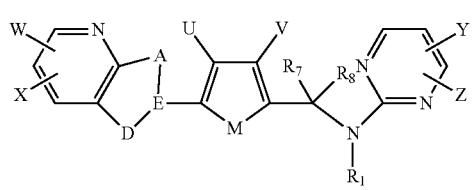 (VIII-11)
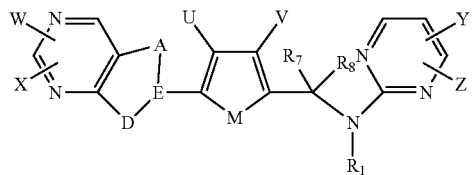 (VIII-12)
wherein
M, U, V, W, X, Y and Z are as defined above;
$R_1$, $R_2$, $R_3$, $R_4$, $R_5$, $R_6$, $R_7$ and $R_8$ are as defined above; and
A and -D-E- are as defined above.
In another subembodiment, a compound of Formula VIII-13 to VIII-20, or a pharmaceutically acceptable salt, ester or prodrug thereof, is provided:
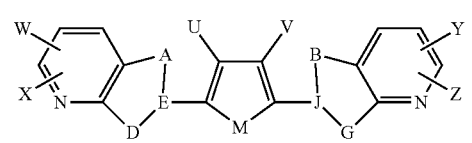 (VIII-13)
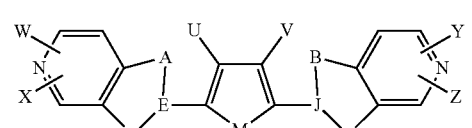 (VIII-14)
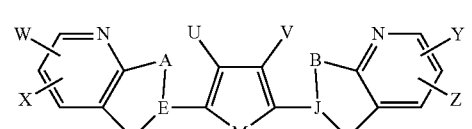 (VIII-15)
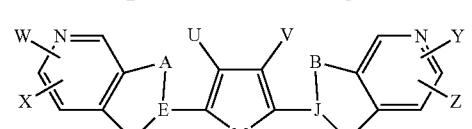 (VIII-16)
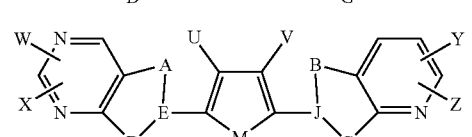 (VIII-17)
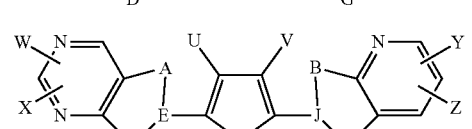 (VIII-18)
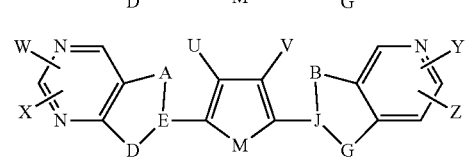 (VIII-19)

-continued (VIII-20)

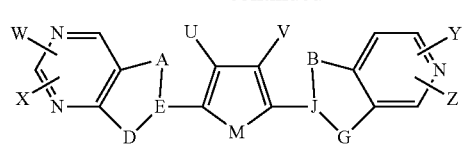

wherein
M, U, V, W, X, Y and Z are as defined above;
$R_2, R_3, R_4, R_5, R_6, R_7$ and $R_8$ are as defined above; and
A, B, -D-E- and -G-J- are as defined above.

In a ninth principal embodiment, the disclosure provides a compound of Formula IX, or a pharmaceutically acceptable salt, ester or prodrug thereof:

Formula IX

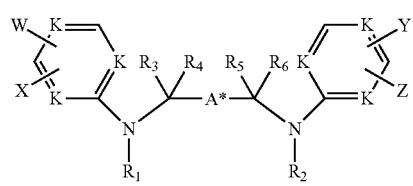

wherein
each K is independently N or CH;
W, X, Y and Z are as defined above;
$R_2, R_3, R_4, R_5$ and $R_6$ are as defined above;
A* is independently selected from the group consisting of formulas a-g:

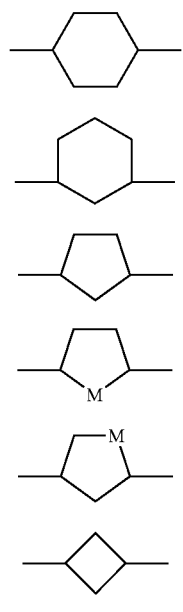

(a)

(b)

(c)

(d)

(e)

(f)

(g) ; and

M is O, S or $NR_3$.

In one subembodiment, a compound of Formula IX-1 to IX-12 is provided, or a pharmaceutically acceptable salt, ester or prodrug thereof:

(IX-1)
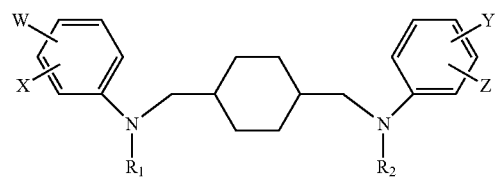

(IX-2)
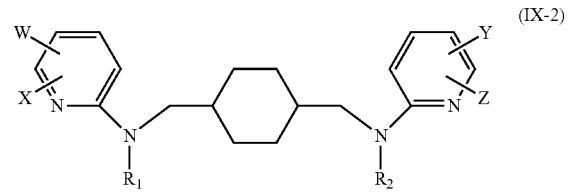

(IX-3)
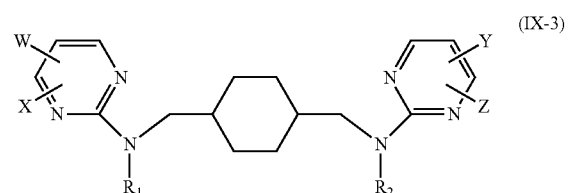

(IX-4)
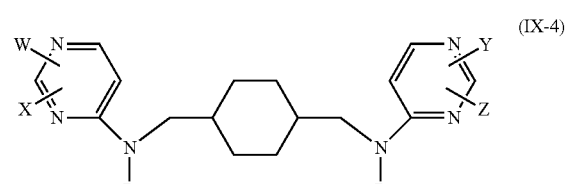

(IX-5)
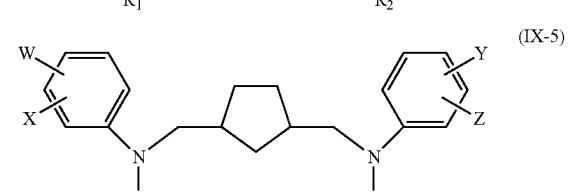

(IX-6)
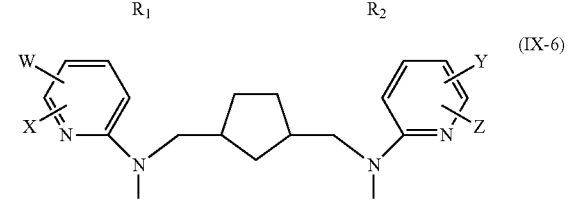

(IX-7)
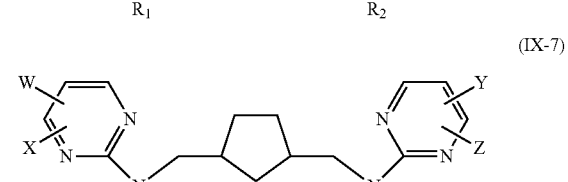

(IX-8)
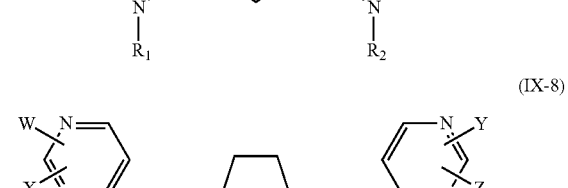

-continued
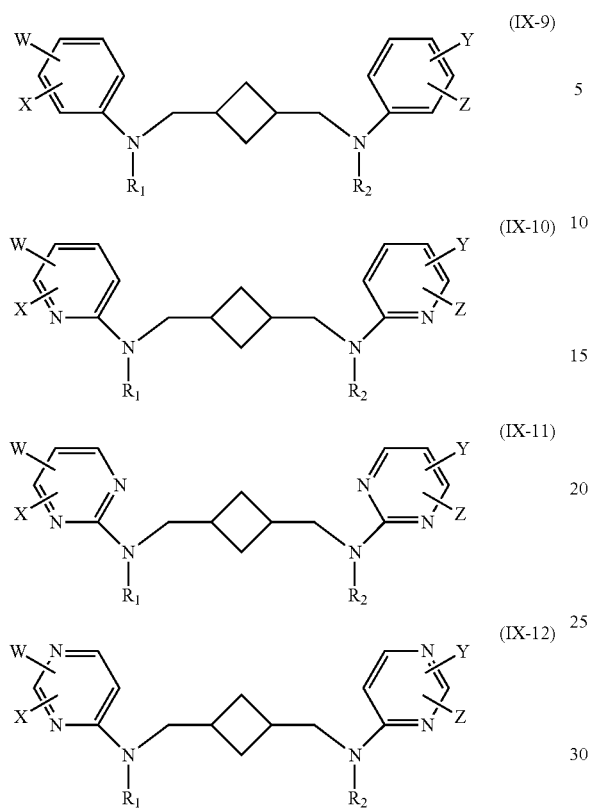
wherein
W, X, Y and Z are as defined above; and
$R_1$, $R_2$, $R_3$, $R_4$, $R_5$ and $R_6$ are as defined above.
In another subembodiment, a compound of Formula IX-13 to IX-24 is provided, or a pharmaceutically acceptable salt, ester or prodrug thereof:
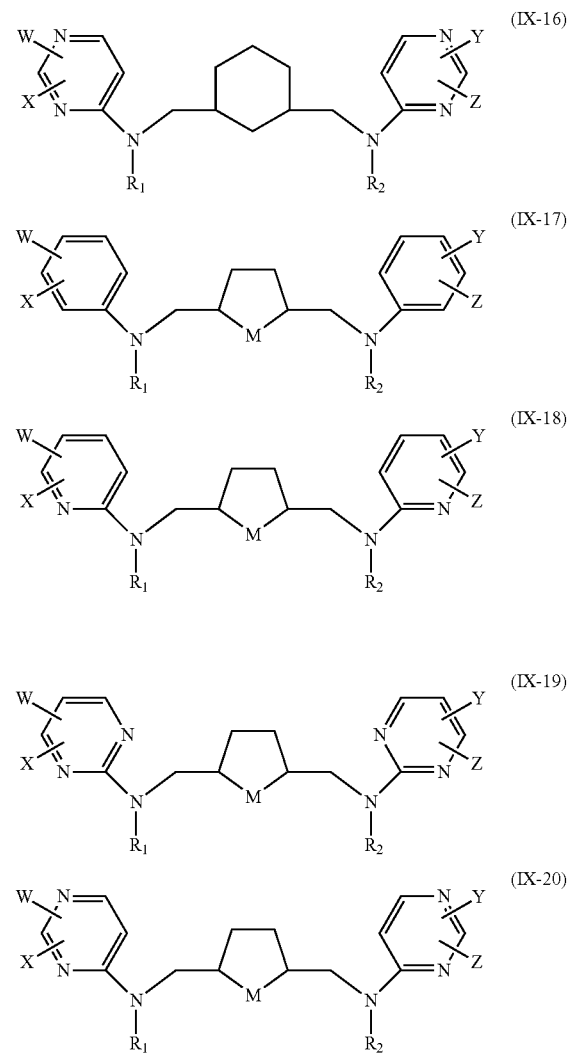
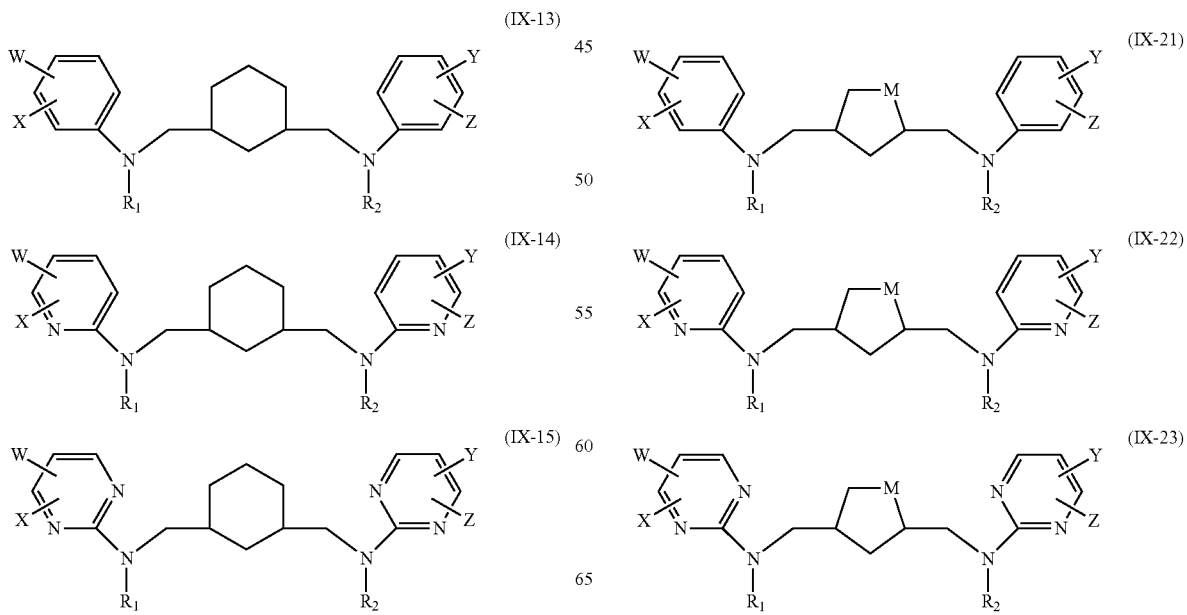

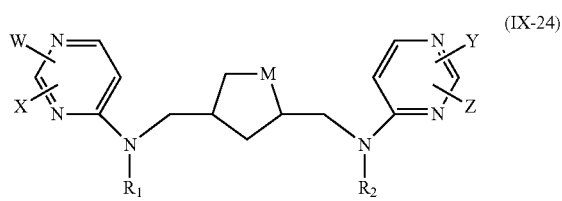

(IX-24)

wherein

M, W, X, Y and Z are as defined above; and $R_1$, $R_2$, $R_3$, $R_4$, $R_5$ and $R_6$ are as defined above.

In yet another subembodiment, a compound of Formula IX-25 to IX-36 is provided, or a pharmaceutically acceptable salt, ester or prodrug thereof:

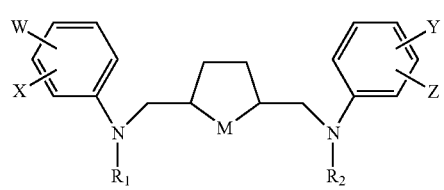

(IX-25)

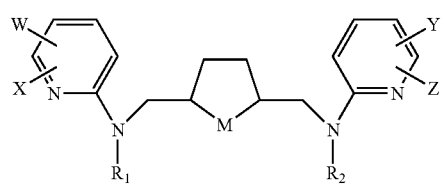

(IX-26)

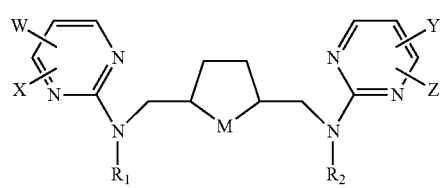

(IX-27)

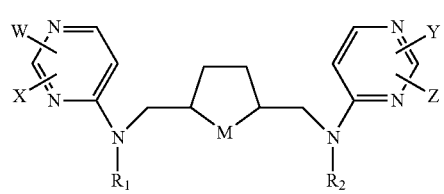

(IX-28)

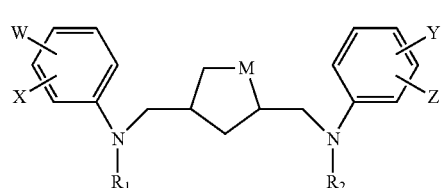

(IX-29)

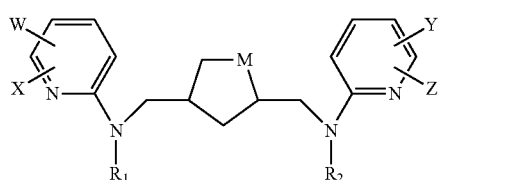

(IX-30)

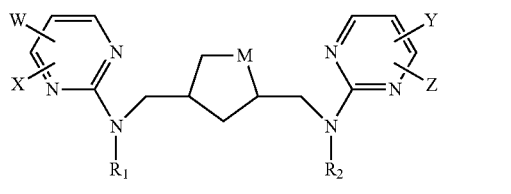

(IX-31)

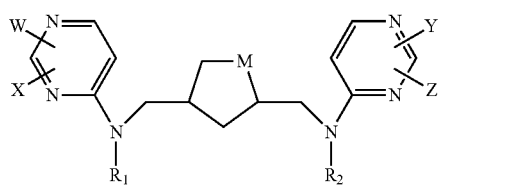

(IX-32)

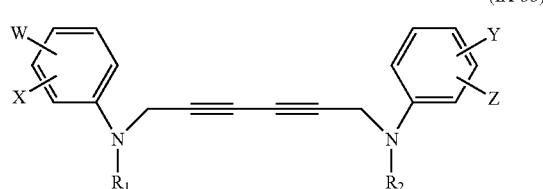

(IX-33)

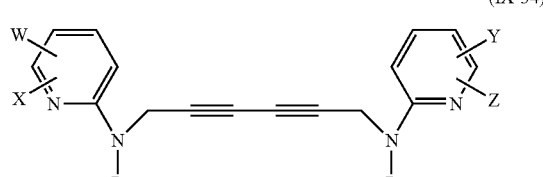

(IX-34)

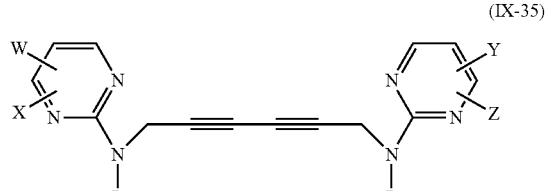

(IX-35)

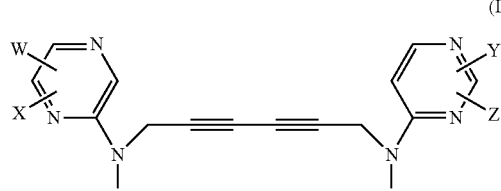

(IX-36)

wherein

M, W, X, Y and Z are as defined above; and $R_1$, $R_2$, $R_3$, $R_4$, $R_5$ and $R_6$ are as defined above.

In a tenth principal embodiment, the disclosure provides a compound of Formula X, or a pharmaceutically acceptable salt, ester or prodrug thereof:

Formula X

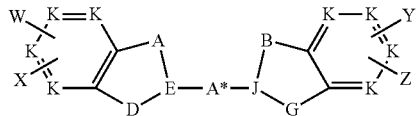

wherein
each K is independently N or CH;
W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above; and
A* is as defined above; and
M is as defined above.

In one subembodiment, a compound of Formula X-1 to X-14 is provided, or a pharmaceutically acceptable salt, ester or prodrug thereof:

(X-1)
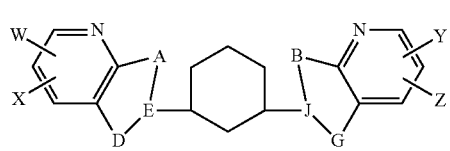

(X-2)
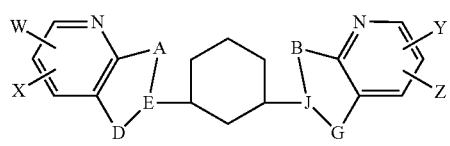

(X-3)
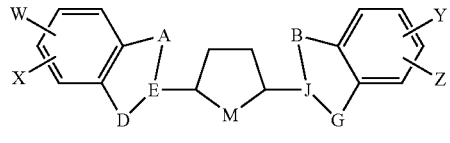

(X-4)
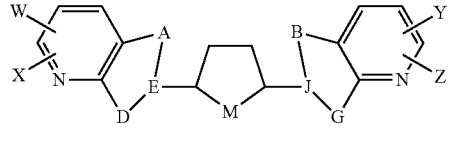

(X-5)
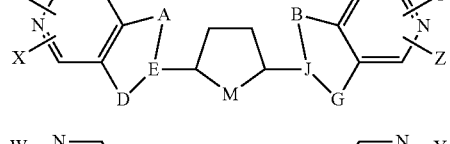

(X-6)
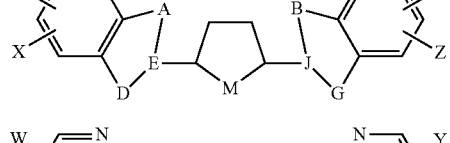

(X-7)
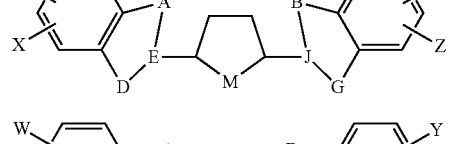

(X-8)
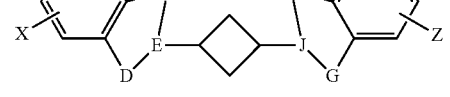

(X-9)
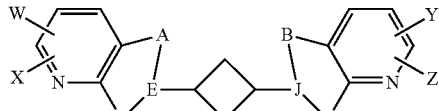

(X-10)
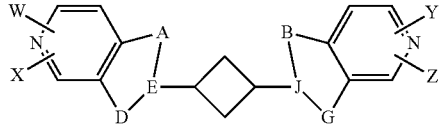

(X-11)
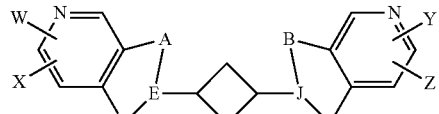

(X-12)
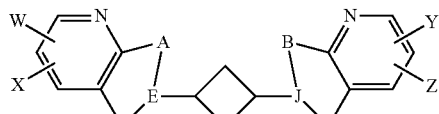

(-X13)
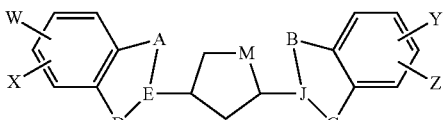

(X-14)
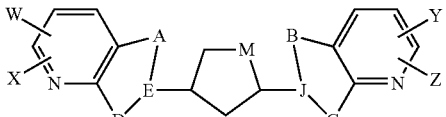

wherein
M, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.

In another subembodiment, a compound of Formula X-15 to X-28 is provided, or a pharmaceutically acceptable salt, ester or prodrug thereof:

(X-15)
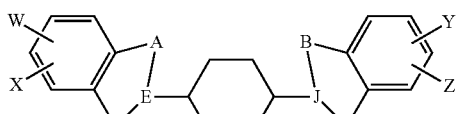

(X-16)
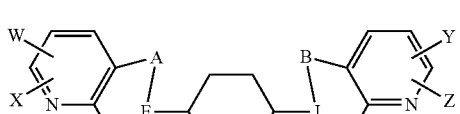

(X-17)
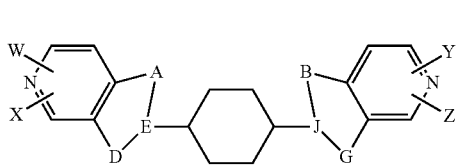

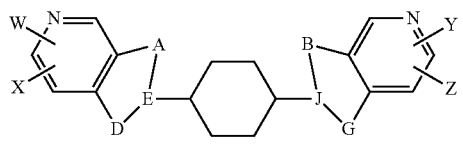
(X-18)
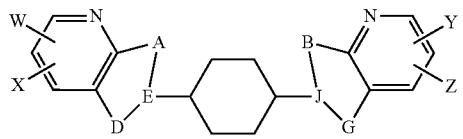
(X-19)
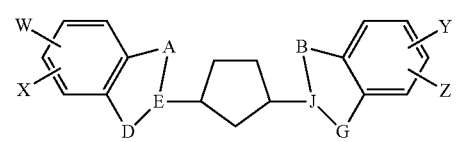
(X-20)
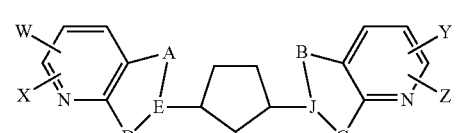
(X-21)
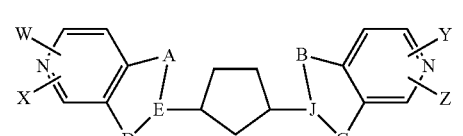
(X-22)
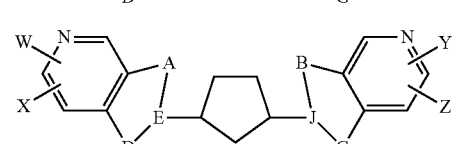
(X-23)
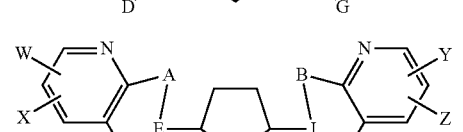
(X-24)
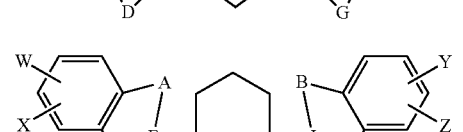
(X-25)
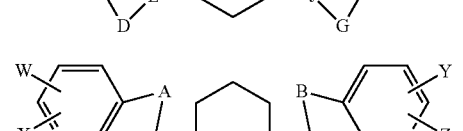
(X-26)
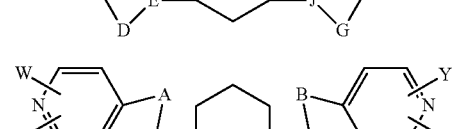
(X-27)
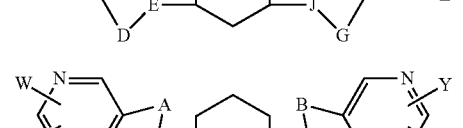
(X-28)
wherein
M, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.
In yet another subembodiment, a compound of Formula X-29 to X-38 is provided, or a pharmaceutically acceptable salt, ester or prodrug thereof:
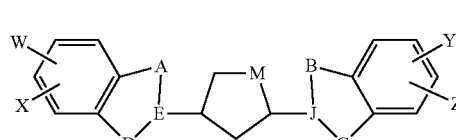
(X-29)
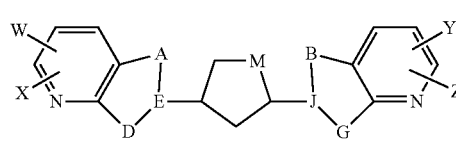
(X-30)
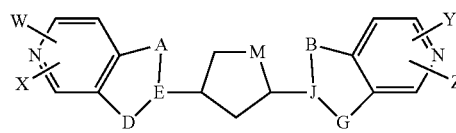
(X-31)
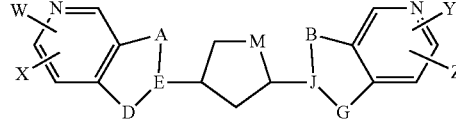
(X-32)
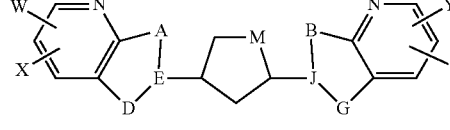
(X-33)
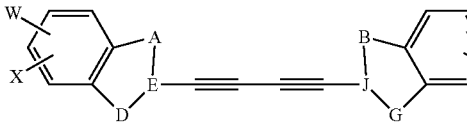
(X-34)
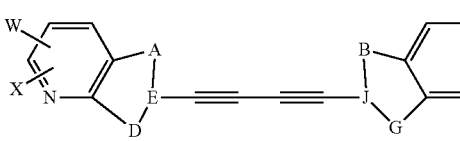
(X-35)
(X-36)
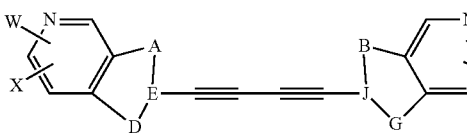
(X-37)

-continued

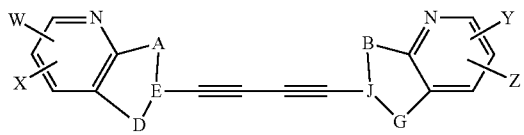
(X-38)

wherein

M, W, X, Y and Z are as defined above;

$R_2$, $R_3$, $R_4$, $R_5$, $R_6$, $R_7$ and $R_8$ are as defined above; and

A and B and -D-E- and -G-J- are as defined above.

In an eleventh principal embodiment, the disclosure provides a compound of Formula XI, or a pharmaceutically acceptable salt, ester or prodrug thereof:

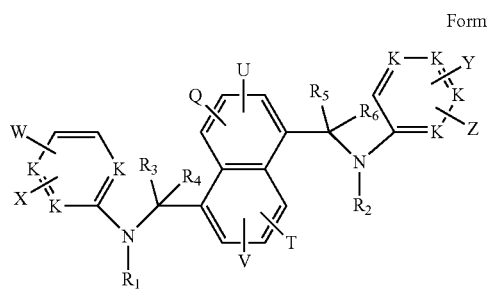
Formula XI wherein each K is independently N or CH;

Q, T, U, V, W, X, Y and Z are as defined above; and $R_1$, $R_2$, $R_3$, $R_4$, $R_5$ and $R_6$ are as defined above.

In one subembodiment of Formula XI, Y and Z are each hydrogen. Alternatively, W and X are each hydrogen. In yet another subembodiment, W, X, Y and Z are all hydrogen.

In one subembodiment, a compound of Formula XI-1 to XI-6 is provided, or a pharmaceutically acceptable salt, ester or prodrug thereof:

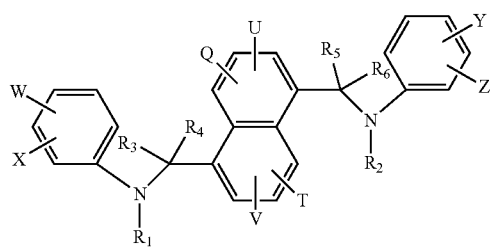
(XI-1)

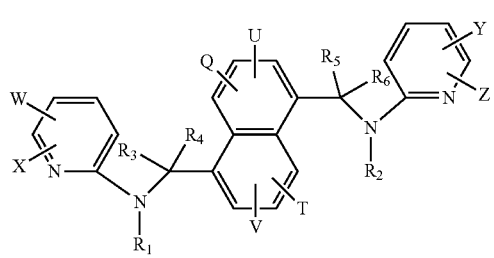
(XI-2)

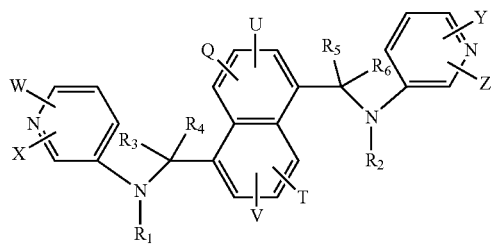
(XI-3)

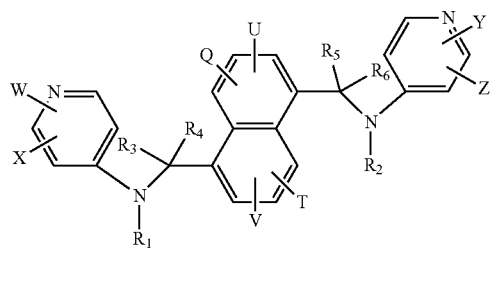
(XI-4)

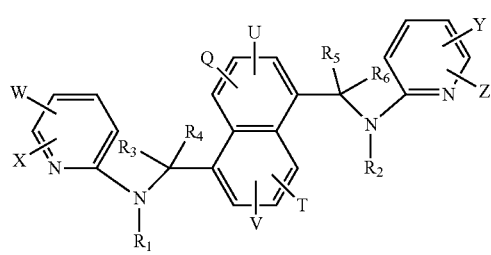
(XI-5)

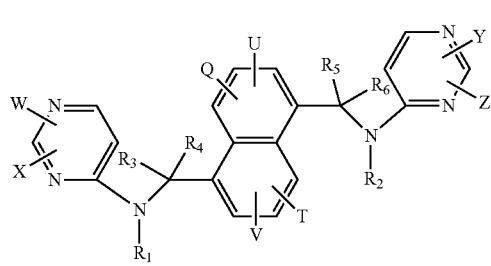
(XI-6)

wherein

Q, T, U, V, W, X, Y and Z are as defined above; and $R_2$, $R_3$, $R_4$, $R_5$ and $R_6$ are as defined above.

In a twelfth principal embodiment, the disclosure provides a compound of Formula XII, or a pharmaceutically acceptable salt, ester or prodrug thereof:

Formula XII

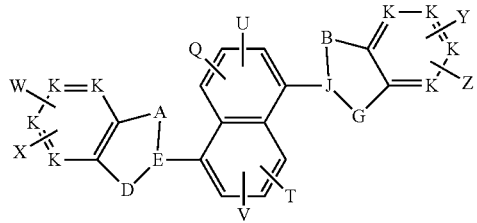

wherein
each K is independently N or CH;
Q, T, U, V, W, X, Y and Z are as defined above;
$R_1$, $R_2$, $R_3$, $R_4$, $R_5$, $R_6$, $R_7$ and $R_8$ are as defined above; and
A and B and -D-E- and -G-J- are as defined above.

In one subembodiment of Formula XII, Y and Z are each hydrogen. Alternatively, W and X are each hydrogen. In yet another subembodiment, W, X, Y and Z are all hydrogen.

In one subembodiment, a compound of Formula XII-1 to XII-5 is provided, or a pharmaceutically acceptable salt, ester or prodrug thereof:

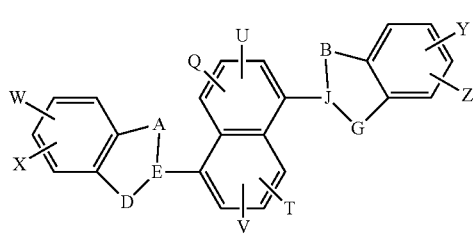
(XII-1)

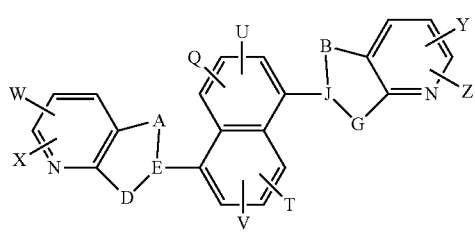
(XII-2)

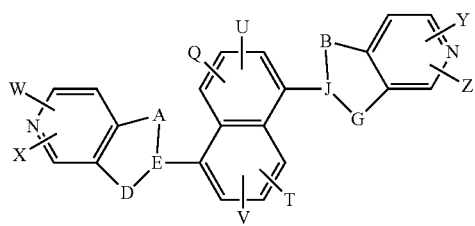
(XII-3)

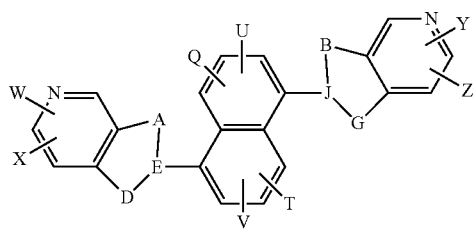
(XII-4)

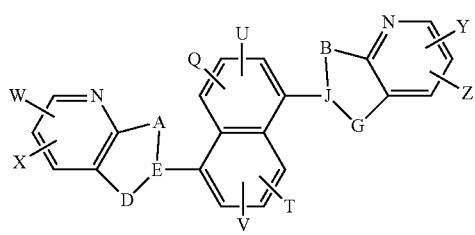
(XII-5)

wherein
Q, T, U, V, W, X, Y and Z are as defined above;
$R_2$, $R_3$, $R_4$, $R_5$, $R_6$, $R_7$ and $R_8$ are as defined above; and
A and B and -D-E- and -G-J- are as defined above.

In a thirteenth principal embodiment, a compound of Formula XIII, or a pharmaceutically acceptable salt, ester or prodrug thereof:

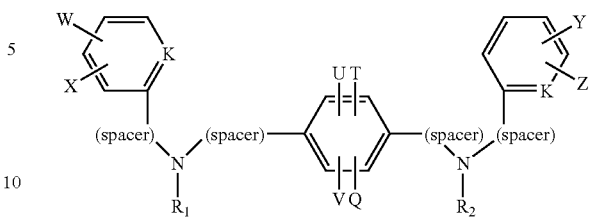
Formula XIII wherein
K, Q, T, U, V, W, X, Y and Z are as defined above;
$R_1$, $R_2$, $R_3$, $R_4$, $R_5$ and $R_6$ are as defined above; and "spacer" is independently a bond, straight chained or branched $C_1$-$C_5$ alkyl, $C_2$-$C_5$ alkenyl, $C_2$-$C_5$ alkynyl, $C_1$-$C_5$ alkoxy, $C_2$-$C_5$ alkenoxy, and $C_2$-$C_5$ alkynoxy wherein the alkyl group can be substituted by a heteroatom (such as N, O or S) for example —$CH_2$—$OCH_2$—, —$CH_2CH_2$—$OCH_2$—, —$CH_2CH_2$—$OCH_2CH_2$—, —$CH_2$—$OCH_2CH_2$—, —$CH_2CH_2$—$OCH_2CH_2CH_2$—, —$CH_2CH_2CH_2$—$OCH_2$—, —$CH_2CH_2CH_2$—$OCH_2CH_2$—, —$CH_2CH_2$—$OCH_2CH_2CH_2$—, —$(CH_2)_n$—$OH(CH_3)$—$(CH_2)_n$—, $CH_2$—$OH(CH_3)$—O—$CH_2$, —$(CH_2)_n$—, —$(CH_2)_n$—CO—, —$(CH_2)_n$—N—, —$(CH_2)_n$—O—, —$(CH_2)_n$—S—, —$(CH_2O)$—, —$(OCH_2)$—, —$(SCH_2)$—, —$(CH_2S$—), -(aryl-O)—, —(O-aryl)-, -(alkyl-O)—, —(O-alkyl)- wherein n is independently 0, 1, 2, 3, 4, 5, 6, 7, 8, 9, or 10.

In a fourteenth principal embodiment, a compound of Formula XIVa or XIVb, or a pharmaceutically acceptable salt, ester or prodrug thereof:

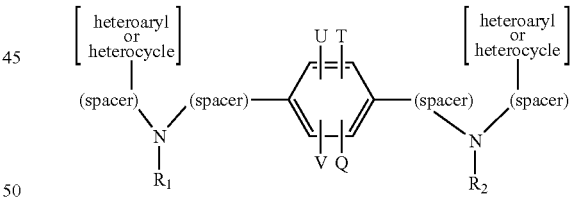
Formula XIVa

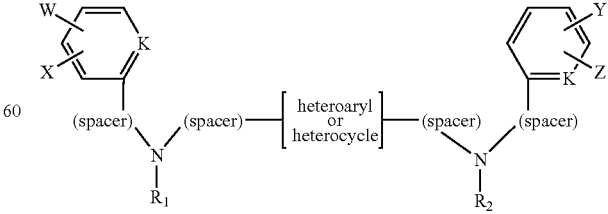
Formula XIVb wherein
K, Q, T, U, V, W, X, Y and Z are as defined above;
$R_1$, $R_2$, $R_3$, $R_4$, $R_5$ and $R_6$ are as defined above;
"spacer" is as defined above; and
"heterocycle" and "heteroaromatic" are as defined herein.

In one particular embodiment, a compound of Formula XV, or a pharmaceutically acceptable salt, ester or prodrug thereof:

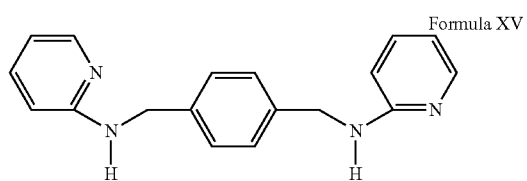 [SMILES: c1ccc(NCc2ccc(CNc3ccccn3)cc2)nc1]

Formula XV

In a particular subembodiment, the compound is a salt of a compound of Formula XV, particularly a chloride salt.

In another particular embodiment, a compound of Formula XVI, or a pharmaceutically acceptable salt, ester or prodrug thereof:

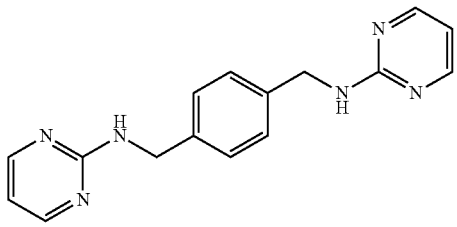

Formula XVI

In another particular embodiment, a compound of Formula XVII, or a pharmaceutically acceptable salt, ester or prodrug thereof:

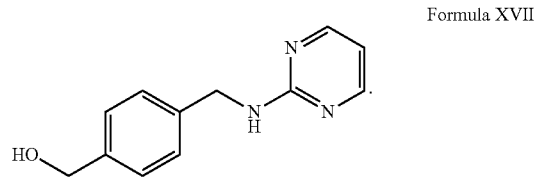 [SMILES: OCc1ccc(CNc2ncccn2)cc1]

Formula XVII

In certain specific embodiments, the compounds are selected from:

| Compound | | $IC_{50}$ (nM) vs SDF-1 |
|---|---|---|
| TN-14003 (Ref) | MSX-207 | <1 |
| AMD-3100 (Ref) | MSX-162 | 100 |
| | MSX-121 | <10 |
| | MSX-122 | <10 |
| | MSX-123 | <10 |

-continued

| Compound | | IC$_{50}$ (nM) vs SDF-1 |
|---|---|---|
| MSX-134 | (pyridin-2-yl-NH-CH$_2$-C$_6$H$_4$(m)-CH$_2$-NH-pyridin-2-yl) | <10 |
| MSX-135 | (Ph-NH-CH$_2$-C$_6$H$_4$(p)-CH$_2$-NH-Ph) | <10 |
| MSX-146 | (Ph-NH-CH$_2$-C$_6$H$_4$(m)-CH$_2$-NH-Ph) | <10 |
| MSX-176 | (Ph-NH-CH$_2$-C$_6$H$_4$(o)-CH$_2$-NH-Ph)·2HCl | >100 |
| MSX-177 | (4-NC-C$_6$H$_4$-NH-CH$_2$-C$_6$H$_4$(p)-CH$_2$-NH-C$_6$H$_4$-CN-4) | >1000 |
| MSX-178 | (4-O$_2$N-C$_6$H$_4$-NH-CH$_2$-C$_6$H$_4$(p)-CH$_2$-NH-C$_6$H$_4$-NO$_2$-4) | >1000 |
| MSX-179 | (4-HO-C$_6$H$_4$-NH-CH$_2$-C$_6$H$_4$(p)-CH$_2$-NH-C$_6$H$_4$-OH-4) | >1000 |

-continued

| Compound | | IC$_{50}$ (nM) vs SDF-1 |
|---|---|---|
| | MSX-180 | ND |
| | MSX-181 | ND |
| | MSX-182 | ND |
| | MSX-183 | <10 |
| | MSX-168 | <100 |
| | MSX-169 | <100 |
| | MSX-173 | >100 |

| Compound | | IC$_{50}$ (nM) vs SDF-1 |
|---|---|---|
| 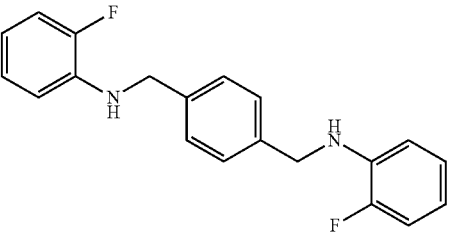 [SMILES: Fc1ccccc1NCc1ccc(CNc2ccccc2F)cc1] | MSX-183 | <10 |
| 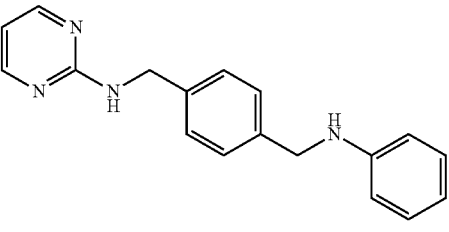 [SMILES: c1ccc(NCc2ccc(CNc3ncccn3)cc2)cc1] | MSX-195 | 10 |
| 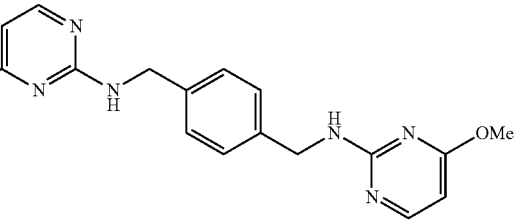 | MSX-200 | 10 |
| 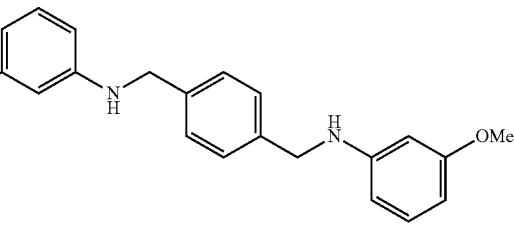 | MSX-205 | 1 |
| 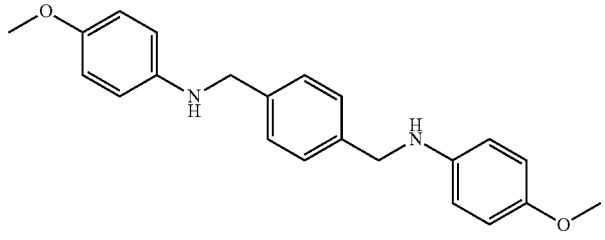 | MSX-125 | >10 |
| 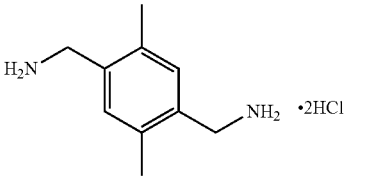 | MSX-126 | >1000 |

-continued

| Compound | | IC$_{50}$ (nM) vs SDF-1 |
|---|---|---|
| MSX-127 | [2,5-dihydroxy-1,4-bis(morpholinomethyl)benzene structure] | >1000 |
| MSX-184 | [N,N'-bis(3-fluorophenyl)-1,4-benzenedimethanamine structure] | >100 |
| MSX-185 | [N,N'-bis(5-fluoropyridin-2-yl)-1,4-benzenedimethanamine structure] | <100 |
| MSX-186 | [(4-{[(5-fluoropyridin-2-yl)amino]methyl}phenyl)methanol structure] | >1000 |
| MSX-189 | [bis-pyrimidine N-oxide structure] | >1000 |
| MSX-190 | [bis(4,6-dichloro-1,3,5-triazin-2-yl)amino structure] | 10 |
| MSX-191 | [bis(4,6-difluoro-1,3,5-triazin-2-yl)amino structure] | 100 |
| MSX-192 | [bis(4-chloro-5-fluoropyrimidin-2-yl)amino structure] | 1 |

-continued
| Compound | | IC$_{50}$ (nM) vs SDF-1 |
|---|---|---|
| 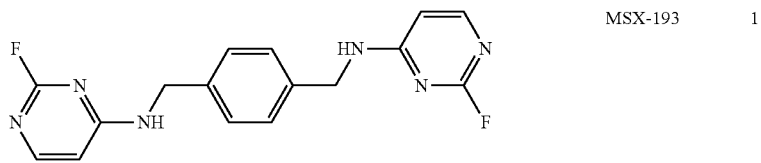 | MSX-193 | 1 |
| 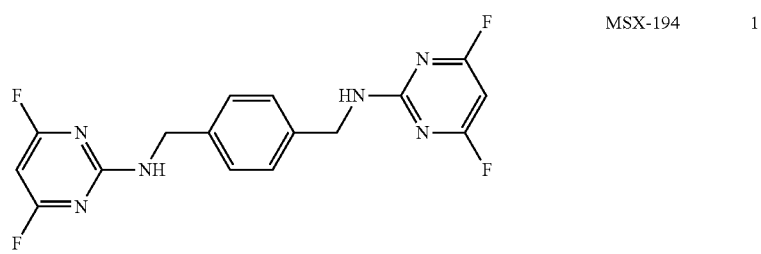 | MSX-194 | 1 |
| 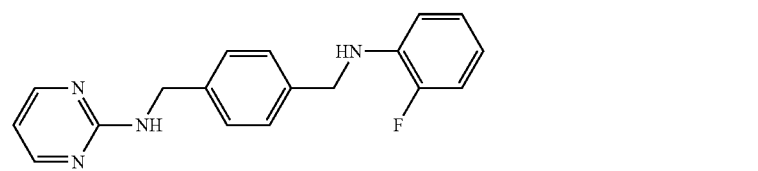 | MSX-196 | 100 |
| | MSX-130 | >1000 |
| 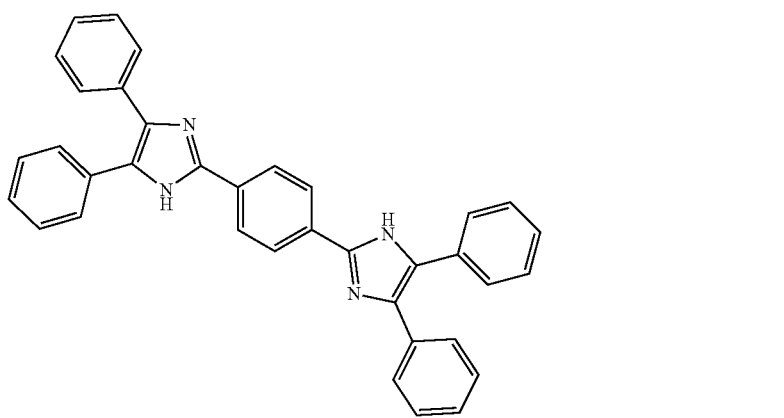 [SMILES: c1ccc(-c2nc(-c3ccc(-c4nc(-c5ccccc5)c(-c5ccccc5)[nH]4)cc3)[nH]c2-c2ccccc2)cc1] | | |
| 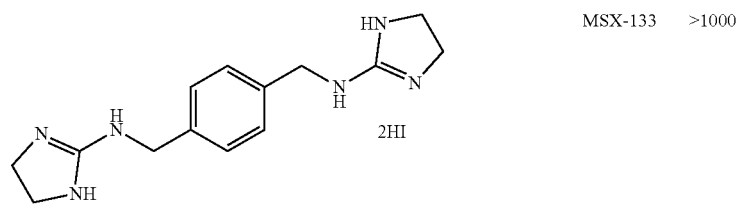 2HI | MSX-133 | >1000 |

| Compound | IC$_{50}$ (nM) vs SDF-1 |
|---|---|
| MSX-137 | >1000 |
| MSX-138 | >1000 |
| MSX-139 (2HCl) | 10 |
| MSX-140 (2HCl) | 10 |
| MSX-141 (2HBr) | >1000 |
| MSX-142 | >1000 |

-continued
| Compound | | IC$_{50}$ (nM) vs SDF-1 |
|---|---|---|
| 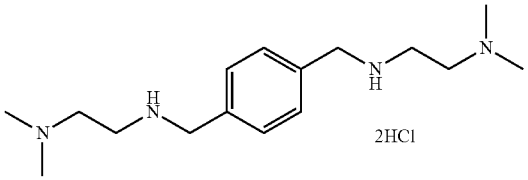 | MSX-156s | >1000 |
| 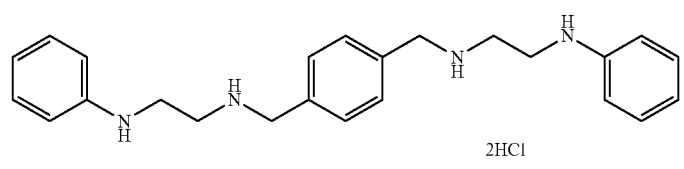 [SMILES: c1ccc(NCCNCc2ccc(CNCCNc3ccccc3)cc2)cc1] | MSX-158 | >1000 |
| 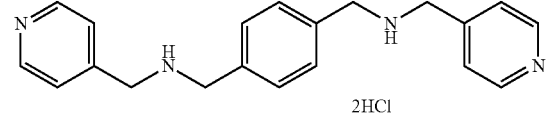 [SMILES: c1cc(CNCc2ccc(CNCc3ccncc3)cc2)ccn1] | MSX-159s | >1000 |
| 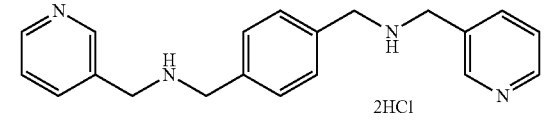 [SMILES: c1cncc(CNCc2ccc(CNCc3cccnc3)cc2)c1] | MSX-160 | >1000 |
| 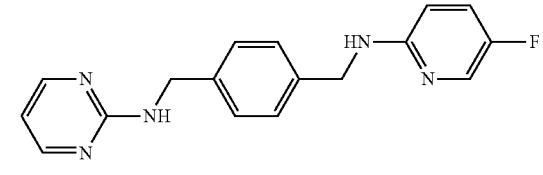 [SMILES: Fc1ccc(NCc2ccc(CNc3ncccn3)cc2)nc1] | MSX-197 | 1 |
| 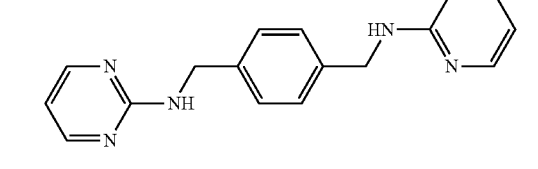 | MSX-198 | <100 |
| 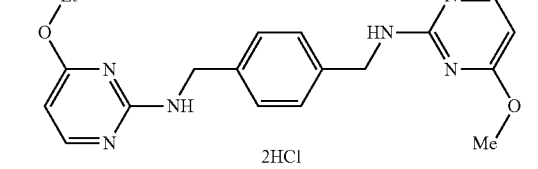 | MSX-199 | ND |
| 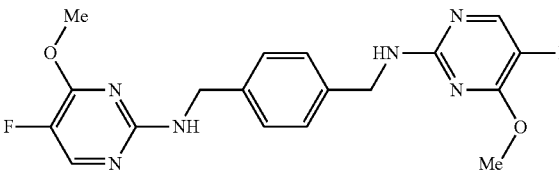 | MSX-201 | 1 |
| 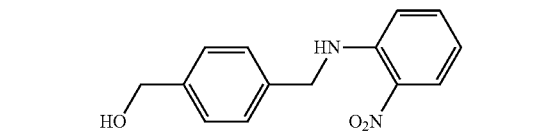 | MSX-202 | 1 |

-continued

| Compound | | IC$_{50}$ (nM) vs SDF-1 |
|---|---|---|
| (3-nitrophenyl-NH-CH2-C6H4-CH2-NH-3-nitrophenyl) | MSX-203 | 1 |
| (4-hydroxymethylphenyl-CH2-NH-3-methoxyphenyl) | MSX-204 | 1000 |
| (2-methoxyphenyl-NH-CH2-C6H4-CH2-NH-2-methoxyphenyl) | MSX-206 | 10 |
| (pyrimidin-2-yl-NH-CH2-C6H4-CH2F) | MSX-207 | 1 |
| (pyrimidin-2-yl-NH-CH2-C6H4-CH2-O-Me) | MSX-208 | 100 |
| (pyrimidin-2-yl-NH-CH2-C6H4-CH2-O-phenyl) | MSX-209 | 10 |
| (phenyl-O-CH2-C6H4-CH2-O-phenyl) | MSX-210 | 1000 |
| (pyridin-2-yl-CH2-NH-CH2-C6H4-CH2-NH-CH2-pyridin-2-yl) 2HCl | MSX-161s | >1000 |
| (pyridin-3-yl-NH-CH2-C6H4-CH2-NH-pyridin-3-yl) 4HCl | MSX-163 | 10 |

-continued

| Compound | | IC$_{50}$ (nM) vs SDF-1 |
|---|---|---|
| | MSX-164 | >100 |
| | MSX-166 | >1000 |
| | MSX-167 | >100 |
| | MSX-170 | <100 |
| | MSX-171 | >1000 |
| | MSX-172 | 10 |

-continued

| Compound | | IC$_{50}$ (nM) vs SDF-1 |
|---|---|---|
| MSX-174 | | >100 |
| MSX-175 | | >100 |
| MSX-211 | | 1000 |
| MSX-212 | | 100 |
| MSX-213 | | >1000 |
| MSX-214 | | 100 |
| MSX-219 | | 10 |
| MSX-221 | | 1 |

| Compound | IC$_{50}$ (nM) vs SDF-1 |
|---|---|
| MSX-222 | 1 |

Definitions

The term alkyl, as used herein, unless otherwise specified, includes but is not limited to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

Whenever the terms "$C_1$-$C_5$ alkyl", "$C_2$-$C_5$ alkenyl", "$C_1$-$C_5$ alkoxy", "$C_2$-$C_5$ alkenoxy", "$C_2$-$C_5$ alkynyl", and "$C_2$-$C_5$ alkynoxy" are used, these are considered to include, independently, each member of the group, such that, for example, $C_1$-$C_5$ alkyl includes straight, branched and where appropriate cyclic $C_1$, $C_2$, $C_3$, $C_4$ and $C_5$ alkyl functionalities; $C_2$-$C_5$ alkenyl includes straight, branched, and where appropriate cyclic $C_2$, $C_3$, $C_4$ and $C_5$ alkenyl functionalities; $C_1$-$C_5$ alkoxy includes straight, branched, and where appropriate cyclic $C_1$, $C_2$, $C_3$, $C_4$ and $C_5$ alkoxy functionalities; $C_2$-$C_5$ alkenoxy includes straight, branched, and where appropriate cyclic $C_2$, $C_3$, $C_4$ and $C_5$ alkenoxy functionalities; $C_2$-$C_5$ alkynyl includes straight, branched and where appropriate cyclic $C_1$, $C_2$, $C_3$, $C_4$ and $C_5$ alkynyl functionalities; and $C_2$-$C_5$ alkynoxy includes straight, branched, and where appropriate cyclic $C_2$, $C_3$, $C_4$ and $C_5$ alkynoxy functionalities.

The term lower alkyl, as used herein, and unless otherwise specified, includes a $C_1$ to $C_4$ saturated straight, branched, or if appropriate, a cyclic (for example, cyclopropyl) alkyl group, optionally including substituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The term includes both substituted and unsubstituted moieties. The aryl group can be substituted with any desired substituent that does not adversely affect the key biological properties, including but not limited to moieties selected from the group consisting of hydroxyl, thiol, amino, alkylamino, arylamino, alkoxy, aryloxy, nitro, cyano, sulfonic acid, halo (F, Cl, I, Br), carboxy, ester, acyl, alkyl, alkenyl, alkynyl, sulfate, phosphoric acid, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "pharmaceutically acceptable salt, ester or prodrug" is used throughout the specification to describe any pharmaceutically acceptable form (such as an ester, phosphate ester, salt of an ester or a related group) of a compound which, upon administration to a patient, provides the compound described in the specification. Pharmaceutically acceptable salts include those derived from pharmaceutically acceptable inorganic or organic bases and acids such as hydrochloric acid, hydrobromic acid, sulfuric acid, nitric acid, phosphoric acid, methanesulfonic acid, ethanesulfonic acid, p-toluensulfonic acid, salicylic acid, malic acid, maleic acid, succinic acid, tartaric acid, citric acid and the like. Suitable salts include those derived from alkali metals such as potassium and sodium, alkaline earth metals such as calcium and magnesium, among numerous other acids well known in the art. Pharmaceutically acceptable "prodrugs" can refer to a compound that is metabolized, for example hydrolyzed or oxidized, in the host to form the compound of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "heterocyclic" refers to a nonaromatic cyclic group that may be partially or fully saturated and wherein there is at least one heteroatom, such as oxygen, sulfur, nitrogen, or phosphorus in the ring. The term heteroaryl or heteroaromatic, as used herein, refers to an aromatic that includes at least one sulfur, oxygen, nitrogen or phosphorus in the aromatic ring. Nonlimiting examples of heterocylics and heteroaromatics are pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, tetrazolyl, benzofuranyl, quinolyl, isoquinolyl, benzothienyl, isobenzofuryl, indolyl, isoindolyl, benzimidazolyl, purine, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, 1,2,3-triazole, 1,2,4-triazole, 1,2,3-oxadiazole, thiazine, pyridazine, benzothiophenyl, isopyrrole, thiophene, pyrazine, or pteridinyl wherein said heteroaryl or heterocyclic group can be optionally substituted with one or more substituent selected from the group consisting of halogen, haloalkyl, alkyl, alkoxy, hydroxy, carboxyl derivatives, amido, hydroxyl, acyl, amino, alkylamino, dialkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference. Heterocycle and heteraromatic groups include purine and pyrimidines.

Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acycl groups such as acetyl and propionyl, methanesulfonyl, and p-toluenelsulfonyl.

The term purine or pyrimidine includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine.

Processes for the Preparation of Active Compounds
General Methods.
$^1$H NMR or $^{13}$C NMR spectra were recorded either on 400 MHz or 100 MHz INOVA Spectrometer or 600 MHz or 150 MHz INOVA Spectrometer. The spectra obtained were referenced to the residual solvent peak. They were recorded in deuterated chloroform, dimethyl sulfoxide-d6, deuterium oxide or acetone-d6. Melting points were taken on a Thomas Hoover capillary melting point apparatus and are uncorrected. Low-resolution EI mass spectra were recorded on a JEOL spectrometer. Element analyses were performed by Atlantic Mircolab (Norcross, Ga.). Flash column chromatography was performed using Scientific Absorbent Incorporated Silica Gel 60. Analytical thin layer chromatography (TLC) was performed on precoated glass backed plates from Scientific Adsorbents Incorporated (Silica Gel 60 F254). Plates were visualized using ultraviolet or iodine vapors or phosphomolybdic acid (PMA).

Six different methods were used to prepare the compounds of the disclosure and the characterization data were listed in Table 1.

Method A: Nucleophilic Addition Between Amines and Cyanamides.

This method is performed according to a modified literature procedure (Braun, et al. (1938) *J. Am. Chem. Soc.* 3: 146-149). 1.0 eq. of diamine dihydrohalide and 3.0 eq. of cyanamide in absolute ethanol were stirred together under refluxing for hours. The solvent was removed under reducing pressure to get the crude salt which was purified by recrystallization in methanol.

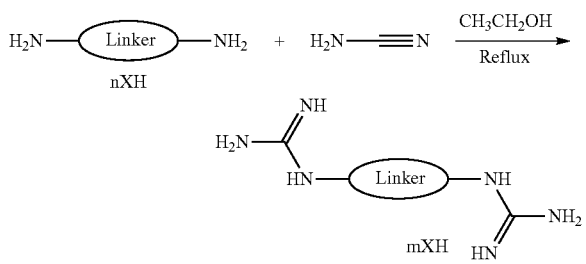

Method B: Addition-Elimination Between Amines and Methyl Mercapto Derivatives.

This method is almost similar to a literature procedure (Linton, et al. (2001) *J. Org. Chem.* 66(22): 7313-7319). 1.0 eq. of diamine and 2.0 eq. methyl mercapto hydrohalide derivatives were dissolved in methanol. A condenser equipped with a NaOH trap at the top was attached. After refluxing for hours, the solution was reduced to minimal volume under reduced pressure. Ethyl either was added to produce white precipitate. This was recrystallized in hot methanol to give pure product.

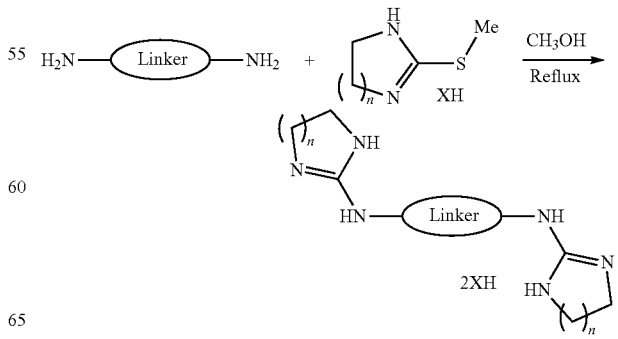

Method C: Condensation Between Aldehydes/Ketones and Amino Guanidines to Give Guanylhydrozone Derivatives.

This method is modified from the literature procedure (Murdock, et al. (1982) *J Med. Chem.* 25:505-518). A mixture of 1.0 eq. dialdehyde/ketone and 2.0 eq. amino guanidine hydrohalides in ethanol was heated under reflux for hours. The mixture was cooled to room temperature and filtered to give the guanylhydrozone hydrohalides.

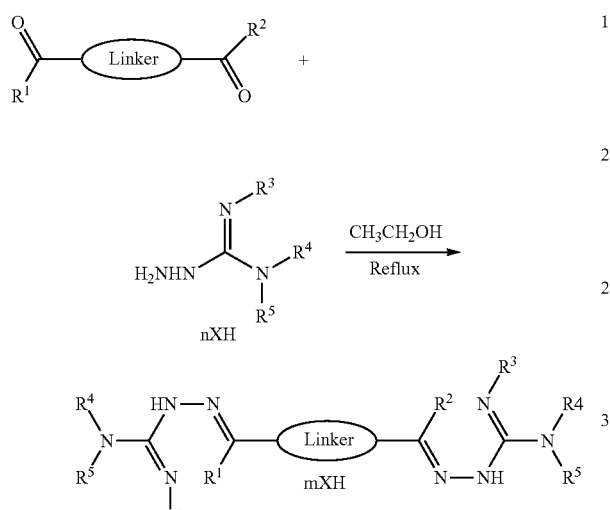

Method D: Reductive Amination Between Aldehydes/Ketones and Amines (Abdel-Magid, et al. (1996) *J Org. Chem.* 61:3849-3862). 1.0 eq. dialdehydes or ketones and 2.0 eq. amines were mixed in 1, 2-dichloroethane and then treated with 3.0 eq. sodium triacetoxyborohydride (1.0-2.0 mol eq. acetic acid may also be added in reactions of ketones). The mixture was stirred at room temperature under an argon or nitrogen atmosphere for hours until the disappearance of the reactants in TLC plates. The reaction mixture was quenched by adding 1 N NaOH, and the product was extracted by ethyl ether, washed by Brine and dried by anhydrous $MgSO_4$. The solvent was evaporated to give the crude free base which could be purified by chromatography. The free base dissolved in ethanolic hydrochloride or tartaric acid to give the salts which usually can recrystallize from $MeOH/Et_2O$.

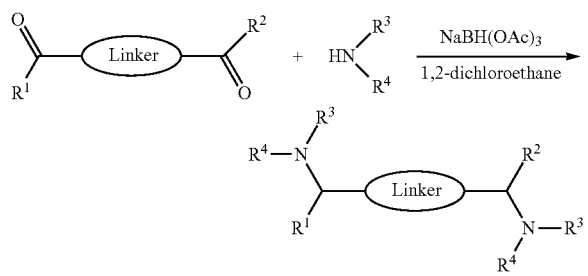

Method E: Reduction of amides (Micovic and Mihailovic (1953) *J Org. Chem.* 18:1190). The amides could be prepared from the corresponding carboxylic acid or carboxylic chlorides. A mixture of carboxylic acid and thionyl chloride was refluxed for hours in an anhydrous system with a condenser equipped with a NaOH trap at the top. The excess thionyl chloride was removed under reduced pressure to get the carboxylic chloride. The carboxylic chloride was dissolved in dichloromethane following the addition of 2.0 eq. amine and 3 eq. pyridine. The mixture was stirred at room temperature until the disappearance of the reactants in the TLC plates. The solvent was removed under reduced pressure to get the crude amides which can be purified by chromatography.

The mixture of 1 eq. amide and 1.9 eq. $LiAlH_4$ in THF was refluxed until the disappearance of the amide from TLC plates. Then the solution was quenched with the addition of water and 15% NaOH aqueous as described in lit.5 and extracted with ethyl ether, dried over $MgSO_4$. Removal of the solvent gave the free amine product which can be purified by the chromatography. The free base dissolved in ethanolic hydrochloride or tartaric acid to give the salts which usually can recrystallize from $MeOH/Et_2O$.

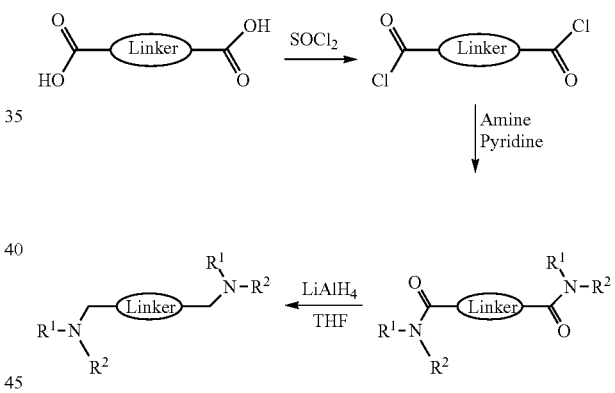

Method F: Nucleophilic substitution of halides with amines. A mixture of 1.0 eq. halides, 2.0 eq. amines and 3 eq. pyridine in ethanol was refluxed for hours until the disappearance of the reactants. The solution was condensed and extracted with ethyl ether, washed with brine, dried with $MgSO_4$. Removal of the solvent gave the free amine product which can be purified by the chromatography. The free base dissolved in ethanolic hydrochloride or tartaric acid to give the salts which usually can recrystallize from $MeOH/Et_2O$.

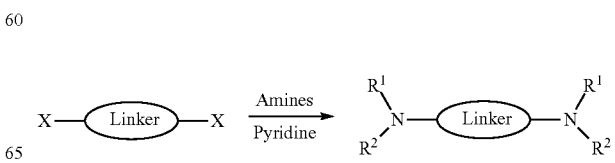

TABLE 1

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS(EI+): m/z (M$^+$) Found (Calcd.) |
|---|---|---|---|---|---|
| WZ1S | 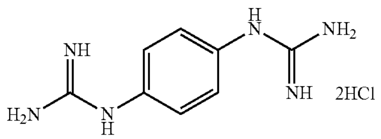 [SMILES: N=C(N)Nc1ccc(NC(=N)N)cc1] | D$_2$O: 600 Mz 1H: 7.40(4H, s); 13C: 159.019, 136.364, 129.981 | 302-304 (dec) | C$_8$H$_{14}$Cl$_2$N$_6$ C: 36.34 (36.24); H: 5.34 (5.32); N: 31.76 (31.70) Cl: 26.70 (26.74) | |
| WZ3S | 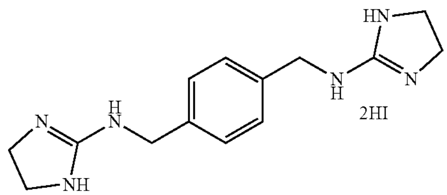 [SMILES: c1cc(CNC2=NCCN2)ccc1CNC1=NCCN1] | DMSO: 400 Mz 1H: 8.66(2H, s); 7.6-8.6(4H, br); 7.31 (4H, s); 4.36(4H, s); 3.60 (8H, s) 13C: 159.31, 136.50, 127.53, 45.06, 42.54 | 294-296 (dec) | C$_{14}$H$_{22}$I$_2$N$_6$ C: 32.06 (31.84) H: 4.35 (4.20) N: 15.77 (15.91) | |
| WZ4S | 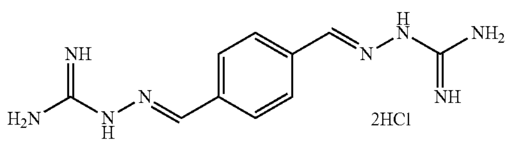 [SMILES: N=C(N)N/N=C/c1ccc(/C=N/NC(=N)N)cc1] | DMSO: 400 Mz 1H: 12.28(2H, s); 8.21 (2H, s); 7.94 (4H, s); 7.60-8.20 (8H, br) 13C: 155.52, 145.98, 135.18, 127.84 | 316-318 (dec) | C$_{10}$H$_{16}$Cl$_2$N$_8$·0.7H$_2$O C: 36.07 (36.20); H: 5.23 (5.29); N: 33.42 (33.77); Cl: 21.11 (21.37) | |
| WZ5S | 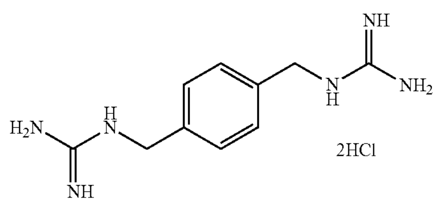 [SMILES: N=C(N)NCc1ccc(CNC(=N)N)cc1] | DMSO: 400 Mz 1H: 8.08 (2H, s); 7.32(4H, s); 6.85-7.71 (8H, br); 4.37(4H, s) 13C: 157.12, 136.61, 127.53, 43.65 | 278-281 (dec) | | |
| WZ6S | 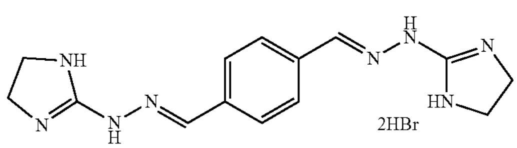 [SMILES: C(=N\NC1=NCCN1)/c1ccc(/C=N/NC2=NCCN2)cc1] | DMSO: 400 Mz 1H: 12.39(2H, s); 8.3-9.2 (4H, br); 8.22 (2H, s); 7.92 (4H, s); 3.75 (8H, s) 13C: 195.31, 136.50, 127.53, 45.06, 42.54 | 349-352 (dec.) | C$_{14}$H$_{20}$Br$_2$N$_8$ C: 41.19 (40.96) H: 6.35 (6.19) N: 28.32 (28.66) | |
| WZ7S | 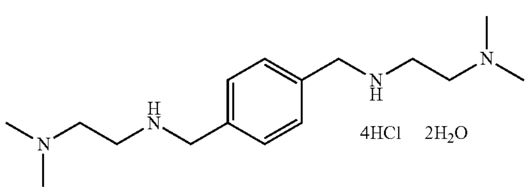 | D$_2$O: 1H (600 MHz): 7.58(4H, s); 4.37(4H, s), 3.58(8H, s); 2.98(12H, s) 13C (400 Mz): 131.95, 130.81, 52.45, 51.30, 43.45, 41.45 | 250-252 (dec.) | C$_{16}$H$_{38}$Cl$_4$N$_4$O$_2$ C: 41.75 (41.83) H: 8.32 (8.26) N: 12.17 (11.92) | |
| WZ8S | 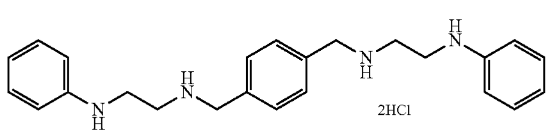 [SMILES: c1ccc(NCCNCc2ccc(CNCCNc3ccccc3)cc2)cc1] | D$_2$O: 400 Mz 1H: 7.45(4H, s); 7.24(4H, t, J = 7.2 Hz); 6.82(2H, t, J = 7.2 Hz); 6.73(4H, d, J = 7.2 Hz); 4.27(4H, s); 3.47(4H, t, J = 6.2 Hz); 3.24(4H, t, J = 6.2 Hz) | 320-322 (dec.) | C$_{24}$H$_{32}$Cl$_2$N$_4$ C: 64.42 (64.32) H: 7.21 (7.21) N: 12.52 (12.30) | |
| WZ8 | 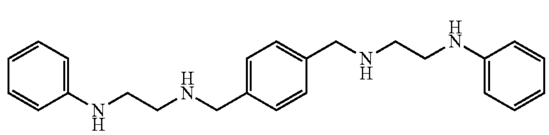 [SMILES: c1ccc(NCCNCc2ccc(CNCCNc3ccccc3)cc2)cc1] | CDCl3: 1H (600 MHz): 7.29(4H, s); 7.18(4H, t, J = 5.2 Hz); 6.71(2H, t, J = 4.8 Hz); 6.64(4H, d, J = 6 Hz); 3.81(4H, s); 3.23(4H, t, J = 3.6 Hz); 2.91(4H, t, J = 3.6 Hz); 4.12(2H, br) 13C (400 Mz): 148.64; 139.18; 129.38; | 42-43 | | |

TABLE 1-continued

CHARACTERIZATION DATA FOR THE PREPARED COMPOUNDS

| Entry | Structure | ¹HNMR/¹³CNMR | M.p. (° C.) | Element Analysis Found (Calcd.) | MS(EI+): m/z (M⁺) Found (Calcd.) |
|---|---|---|---|---|---|
| | | 128.36; 117.53; 113.13; 53.49; 48.17; 43.65 | | | |
| WZ9S | 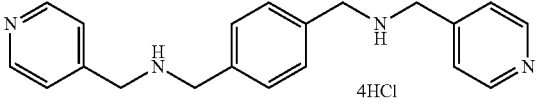 [SMILES: c1cc(CNCc2ccc(CNCc3ccncc3)cc2)ccn1] 4HCl | D₂O: 400 Mz 1H: 8.87(4H, d, J = 7.2 Hz); 8.12(4H, d, J = 7.2 Hz); 7.63(4H, ); 4.66(4H, ); 4.48(4H, s) 13C: 151.21; 142.45; 131.84; 131.18; 127.47; 51.35; 49.03 | 244-246 (dec.) | C₂₀H₂₆Cl₄N₄0.7H₂O C: 50.60 (50.37) H: 5.74 (5.79) N: 11.49 (11.75) | |
| WZ9 | 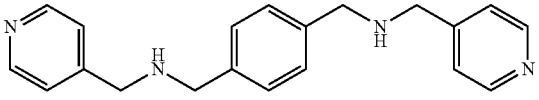 [SMILES: c1cc(CNCc2ccc(CNCc3ccncc3)cc2)ccn1] | CDCl3: 1H (600 Mz): 8.55(4H, d, J = 5.4 Hz); 7.32(4H, s); 7.30(4H, d, J = 5.4 Hz); 3.83(4H, ); 3.81(4H, s); 1.73(2H, s) 13C (400 Mz): 149.73; 149.38; 138.72; 128.21; 122.93; 52.84; 51.72 | | | |
| WZ29S | 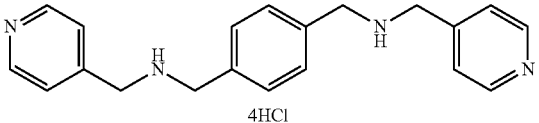 [SMILES: c1cc(CNCc2ccc(CNCc3ccncc3)cc2)ccn1] 4HCl | D2O: 600 Mz 1H: 8.87(4H, d J = 7.2 Hz); 8.12(4H, d, J = 7.2 Hz); 7.63(4H, s); 4.66(4H, s); 4.48(4H, s) | | C20H26Cl4N4.0.7H2O C: 50.57(50.37) H: 5.70(5.79) N: 11.55(11.75) | |
| WZ10S | 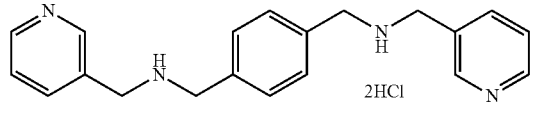 [SMILES: c1cncc(CNCc2ccc(CNCc3cccnc3)cc2)c1] 2HCl | D₂O: 1H: 600 mHz 8.61(2H, dd, J = 6 Hz, 1.2 Hz); 8.60(2H, d, J = 2.4 Hz); 7.99(2H, dt, J = 7.8 Hz, 1.8 Hz); 7.56(6H, m); 4.39 (4H, s); 4.37 (4H, s) 13C: 400 MHz 148.85; 149.82; 139.26; 132.13; 130.81; 127.48; 124.83; 50.48; 48.15 | 318-320 (dec.) | C₂₀H₂₄Cl₂N₄ C: 60.45 (61.38) H: 6.17 (6.18) N: 13.89 (14.32) | |
| WZ11S | 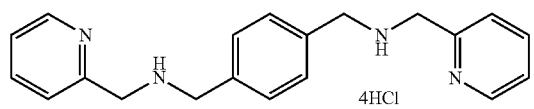 [SMILES: c1ccc(CNCc2ccc(CNCc3ccccn3)cc2)nc1] 4HCl | D₂O: 1H: 8.76(2H, d, J = 4.8 Hz); 8.35(2H, dt, J = 8 Hz, J = 1.2 Hz); 7.91(2H, d, J = 8 Hz); 7.86(2H, t, J = 6.4 Hz); 4.62(4H, s); 4.47(4H, s) 13C: 146.12; 145.53; 144.95; 131.84; 131.07; 127.47; 127.26; 51.18; 47.91 | 236-238 (dec.) | C₂₀H₂₆Cl₄N₄0.5H₂O 0.2CH₃COOCH₂CH₃ C: 50.59 (50.89) H 6.08 (5.87) N: 11.46 (11.41) | |
| WZ13S | 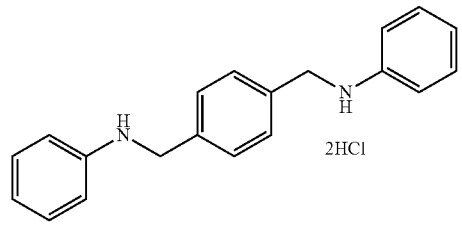 [SMILES: c1ccc(NCc2ccc(CNc3ccccc3)cc2)cc1] 2HCl | DMSO-D2O: 400 Mz 1H: 7.35 (4H, s), 7.30 (4H, m), 7.10 (6H, m), 4.41 (4H, s) 13C: 137.85, 133.27, 129.88, 129.46, 126.58, 121.70, 51.82 | | | |

TABLE 1-continued

CHARACTERIZATION DATA FOR THE PREPARED COMPOUNDS

| Entry | Structure | ¹HNMR/¹³CNMR | M.p. (° C.) | Element Analysis Found (Calcd.) | MS(EI+): m/z (M⁺) Found (Calcd.) |
|---|---|---|---|---|---|
| WZ13 | 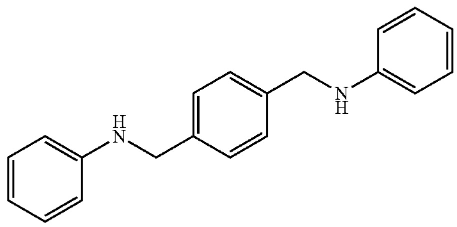 [SMILES: c1ccc(NCc2ccc(CNc3ccccc3)cc2)cc1] | CDCl3: 400 Mz 1H; 7.38 (4H, s); 7.22 (4H, t, J = 7.6 Hz); 6.76 (2H, t, J = 7.6 Hz); 7.67 (4H, d, J = 7.6 Hz); 4.35 (4H, s); 4.06 (2H, br) 13C: 148.28, 138.65, 129.46, 127.98, 117.78, 113.03, 48.20 | 126-127 | | |
| WZ14 | 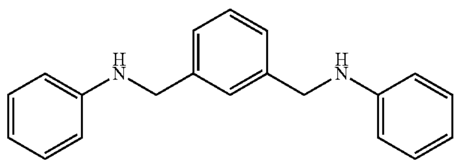 [SMILES: c1ccc(NCc2cccc(CNc3ccccc3)c2)cc1] | CDCl3: 400 Mz 1H: 7.43(1H, s); 7.36(3H, m); 7.23 (4H, m); 6.78 (2H, t, J = 7.7 Hz); 6.68 (4H, d, J = 7.7 Hz); 4.07(2H, s) 13C: 148.26, 140.09, 129.44, 129.03, 126.74, 126.54, 117.77, 113.05, 48.42 | | | 288.5 (288.4) |
| WZ14S | 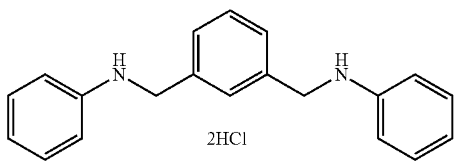 [SMILES: c1ccc(NCc2cccc(CNc3ccccc3)c2)cc1] | D2O: 400 Mz 1H: 7.49(6H, m); 7.37(3H, m); 7.21(4H, m); 7.15(1H, s); 4.59(4H, s) 13C: 133.95, 132.22, 131.68, 131.06, 130.32, 129.86, 122.93, 54.6 | | | |
| WZZL 811 | 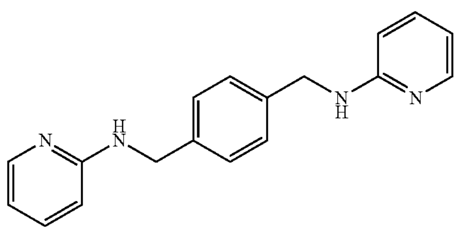 [SMILES: c1ccc(NCc2ccc(CNc3ccccn3)cc2)nc1] | DMSO: 400 Mz 1H: 7.93(2H, dd, J = 4.8 Hz, 1.2 Hz); 7.34(2H, td, J = 12.8 Hz, 2 Hz); 7.25(4H, s); 6.96(2H, t, J = 6 Hz), 6.45(4H, m); 4.41(4H, d, J = 6 Hz) 13C: 158.66, 147.53, 138.84, 136.60, 127.11, 111.67, 108.11, 43.93 | 192-194 | | 290.5 (290.4) |
| WZZL 811S | 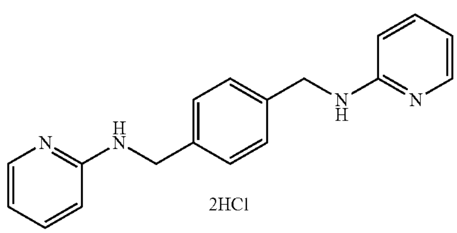 [SMILES: c1ccc(NCc2ccc(CNc3ccccn3)cc2)nc1] | D2O: 400 Mz 1H: 7.89(2H, td, J = 8.4 Hz, 1.6 Hz); 7.79(2H, d, J = 6.4 Hz); 7.43(4H, s); 7.02(2H, d, J = 8.4 Hz); 6.90(2H, t, J = 6.4 Hz); | | C₁₈H₁₈N₄.2HCl C: 59.28 (59.51) H: 5.44 (5.55) N: 15.19 (15.4) Cl: 19.73 (19.52) | |
| WZZL 811TS | 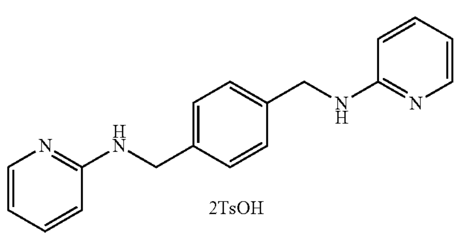 [SMILES: c1ccc(NCc2ccc(CNc3ccccn3)cc2)nc1] | DMSO: 1H (600 Mz): 9.07(2H, br), 7.95(4H, m); 7.49(4H, d, J = 8.4 Hz); 7.40(4H, s); 7.11(6H, m); 6.90(2H, t, J = 6 Hz); 4.58(4H, d, J = 5.4 Hz); 3.68(2H, br) 2.84(4H, S) 13C (400 Mz): 152.56, 145.40, 143.49, 137.82, 136.26, 135.88, 128.12, 127.93, 125.48, 112.42, 44.56, 20.78 | | | |

TABLE 1-continued

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS(EI+): m/z (M$^+$) Found (Calcd.) |
|---|---|---|---|---|---|
| WZZL 811LTR | (structure with two 2-pyridyl-aminomethyl groups on phenylene, with 1.75 tartaric acid) | D2O: 400 Mz 1H: 7.88(2H, t, J = 9.2 Hz); 7.78(2H, d, J = 6.4 Hz); 7.42(4H, s); 7.02(2H, d, J = 9.2 Hz); 6.89(2H, t, J = 6.4 Hz); 4.62(4H, s); 4.45(3H, s) 13C: 173.18, 158.52, 147.25, 138.78, 136.79, 127.14, 111.69, 108.23, 72.16, 43.94 | | $C_{18}H_{18}N_4 \cdot 1.75 C_4H_6O_6$ C: 53.51 (54.3) H: 5.35 (5.19) N: 10.11 (10.13) | |
| WZ17 | (structure with two 3-pyridyl-aminomethyl groups on phenylene) | DMSO 1H (600 Mz): 7.96(2H, D, J = 3 Hz); 7.73(2H, dd, J = 3 Hz, 1.2 Hz); 7.32(4H, s); 7.02(2H, dd, J = 6 Hz, 4.2 Hz); 6.86(2 Hz, dq, J = 6 Hz, 4.2 Hz, 1.8 Hz); 6.46(2H, t, 6 Hz); 6.25(4H, d, J = 6 Hz) 13C (400 Mz): 145.30, 138.79, 137.57, 136.17, 128.00, 124.21, 118.39, 46.42, | | | 290.4 (290.4) |
| WZ17S | (structure with two 3-pyridyl-aminomethyl groups on phenylene, XHCl) | D2O: 600 Mz 1H: 7.92(4H, m); 7.67 (4H, m); 7.42(4H, s); 4.49(4H, s) 13C: 147.21, 136.80, 128.30, 128.25, 127.85, 127.16, 124.26, 45.73 | | | |
| WZ18 | (structure with two N-methyl-N-phenyl-aminomethyl groups on phenylene) | CDCl3: 400 Mz 1H: 7.24(4H, m); 7.19(4H, s); 6.75(4H, m); 4.53(4H, s); 3.02(6H, s) 13C: 149.90, 137.83, 129.35, 127.16, 116.69, 112.52, 56.53, 38.69 | | | |
| WZ19 | (structure with two benzylaminomethyl groups on phenylene) | DMSO 1H (600 Mz): 7.32(8H, m); 7,28(4H, s); 7.22(2H, tt, J = 7.2 Hz, 1.2 Hz); 3.66(4H, s); 3.65(4H, s); 2.53(2H, s) 13C (400 Mz): 140.44, 139.12, 128.49, 128.33, 128.26, 127.04, 53.24, 53.00 | | | |
| WZ19S | (structure with two benzylaminomethyl groups on phenylene, 2HCl) | DMSO: 400 Mz 1H: 9.66(4H, s); 7.59(4H, s); 7.54(4H, m); 7.43(6H, m); 4.17(4H, s); 4.13(4H, s) | | | |

TABLE 1-continued

CHARACTERIZATION DATA FOR THE PREPARED COMPOUNDS

| Entry | Structure | ¹HNMR/¹³CNMR | M.p. (° C.) | Element Analysis Found (Calcd.) | MS(EI+): m/z (M⁺) Found (Calcd.) |
|---|---|---|---|---|---|
| WZ20 | 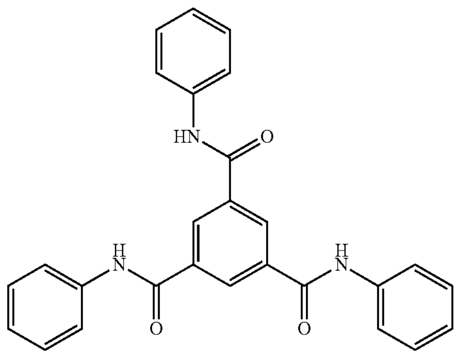 [SMILES: O=C(Nc1ccccc1)c1cc(C(=O)Nc2ccccc2)cc(C(=O)Nc2ccccc2)c1] | DMSO 1H (600 Mz): 10.60(3H, s); 8.71(3H, s); 7.83(6H, d, J = 7.8 Hz); 7.40(6H, t, J = 7.8 Hz); 7.15(3H, t, J = 7.2 Hz); 13C (400 Mz): 164.54, 138.94, 135.50, 129.79, 128.75, 124.00, 120.41 | 318-320 | | |
| WZ21 | 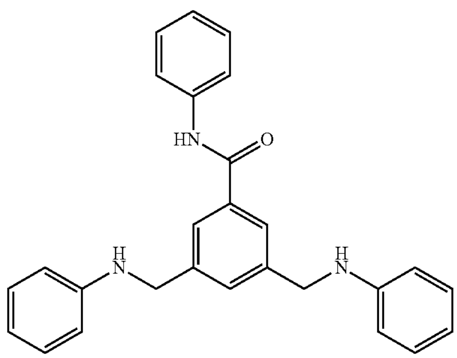 [SMILES: O=C(Nc1ccccc1)c1cc(CNc2ccccc2)cc(CNc2ccccc2)c1] | CDCl3: 400 Mz 1H: 7.79(3H, s); 7.62(2H, d, J = 7.8 Hz), 7.58(1H, s); 7.38(2H, t, J = 7.8 Hz); 7.18(5H, m); 6.75(2H, td, J = 7.8 Hz, 1.2 Hz); 6.64(4H, d, J = 6.6 Hz); 4.41(4H, s) 13C: 165.97, 147.92, 141.07, 138.00, 135.79, 129.80, 129.46, 129.18, 125.03, 124.78, 120.52, 118.02, 113.15, 48.04 | | | 407.6 (407.5) |
| WZ22 | 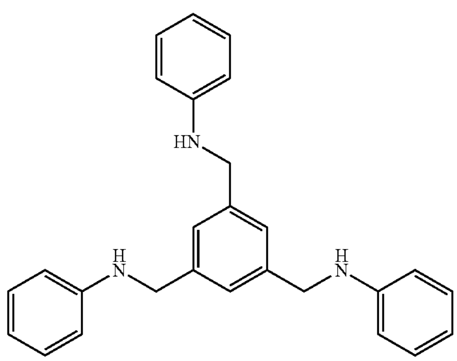 [SMILES: c1ccc(NCc2cc(CNc3ccccc3)cc(CNc3ccccc3)c2)cc1] | CDCl3: 400 Mz 1H: 7.31(3H, s); 7.18(6H, m); 6.74 (3H, tt, J = 7.2 Hz, 0.8 Hz); 6.63(6H, dm, J = 7.2 Hz); 4.32(6H, s); 4.03(3H, br) 13C: 148.24, 140.60, 129.44, 125.66, 117.84, 113.10, 48.42 | | | 393.5 (393.5) |
| WZ22S | 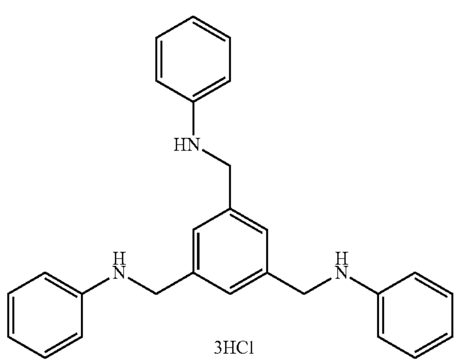 [SMILES: c1ccc(NCc2cc(CNc3ccccc3)cc(CNc3ccccc3)c2)cc1] | D2O: 400 Mz 1H: 7.41(9H, m); 7.16(3H, s); 6.98 (6H, m); 4.51(6H, S) | | | |

TABLE 1-continued

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS(EI+): m/z (M$^+$) Found (Calcd.) |
|---|---|---|---|---|---|
| WZ23 | 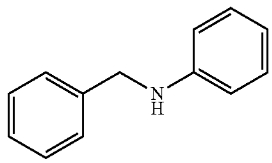 [SMILES: c1ccc(CNc2ccccc2)cc1] | CDCl3: 1H (600 Mz): 7.41(4H, m); 7.32(1H, t, J = 7.2 Hz); 7.22(2H, t, J = 7.2 Hz); 6.76(1H, td, J = 7.2 Hz, 1.2 Hz); 6.68(2H, d, J = 7.2 Hz); 4.37 (2H, s); 4.06(1H, br) 13C (400 Mz): 148.33, 139.62, 129.44, 128.81, 127.68, 127.39, 117.72, 113.01, 48.46 | 34-35 | | |
| WZ23S | 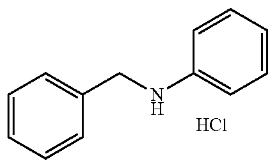 [SMILES: c1ccc(CNc2ccccc2)cc1 ; Cl] | CDCl3: 600 Mz 1H: 11.85(2H, br); 7.30(10H, m); 4.36(2H, s) 13C: 134.37, 131.26, 129.86, 129.60, 129.58, 129.44, 128.87, 124.17, 56.18 | 211-212 | | |
| WZ24 | 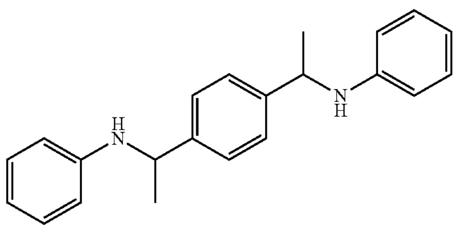 [SMILES: CC(Nc1ccccc1)c1ccc(C(C)Nc2ccccc2)cc1] | CDCl3: 400 Mz 1H: 7.32(4H, s); 7.11(4H, t, J = 7.8 Hz); 6.66(2H, tm, J = 7.2 Hz); 6.52(4H, dm, J = 7.6 HZ); 4.48(2H, m); 1.52(3H, s); 1.50(3H, s) 13C: 147.51, 143.93, 143.96, 129.30, 126.35, 117.35, 117.36, 113.43, 53,31, 53.29, 25.01, 24.91 | | | |
| WZ25 | 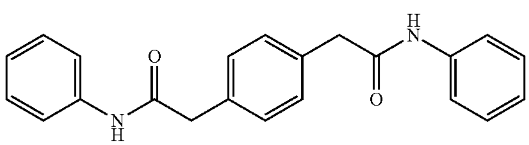 [SMILES: O=C(Cc1ccc(CC(=O)Nc2ccccc2)cc1)Nc1ccccc1] | DMSO 1H (600 Mz): 10.13(2H, s); 7.58(4H, d, J = 7.2 Hz); 7.28(8H, t, J = 8.1 Hz); 7.02(2H, t, J = 7.2 Hz); 3.61 (4H, s) 13C (400 Mz): 169.13, 139.23, 134.24, 129.05, 128.69, 123.18, 119.10 42.95 | | | |
| WZ26 | 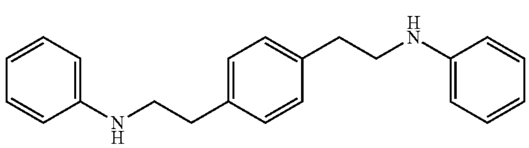 [SMILES: c1ccc(NCCc2ccc(CCNc3ccccc3)cc2)cc1] | CDCl3 1H (600 Mz): 7.20(8H, m); 6.73(2H, t, J = 7.2 Hz); 6.64(4H, d, J = 7.2 Hz); 3.69(2H, br); 3.42(4H, t, J = 7.2 Hz); 2.92(4H, t, J = 7.2 Hz) 13C (400 Mz): 148.21, 137.60, 129.49, 129.22 117.87, 113.18, 45.24, 35.32 | | | 316.5 (316.4) |
| WZ27 | 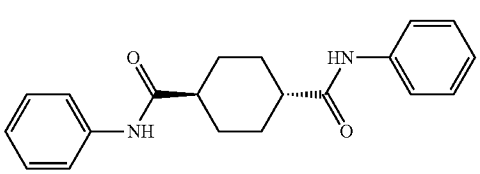 [SMILES: O=C(Nc1ccccc1)[C@H]1CC[C@H](C(=O)Nc2ccccc2)CC1] | DMSO 1H (600 Mz): 9.86(2H, s); 7.60(4H, d, J = 1.8 Hz); 7.28(4H, t, J = 7.8 Hz); 7.02(2H, t, J = 7.2 Hz); 2.35(2H, br); 1.92(4H, d, J = 6.6 Hz); 1.49(4H, m) 13C (400 Mz): 173.95, 139.43, 128.64, 122.93, 119.04, 44.10, 28.29 | | | |

TABLE 1-continued

CHARACTERIZATION DATA FOR THE PREPARED COMPOUNDS

| Entry | Structure | $^1$HNMR/$^{13}$CNMR | M.p. (° C.) | Element Analysis Found (Calcd.) | MS(EI+): m/z (M$^+$) Found (Calcd.) |
|---|---|---|---|---|---|
| WZ28 | 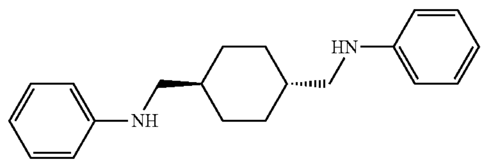 [SMILES: c1ccc(NC[C@H]2CC[C@H](CNc3ccccc3)CC2)cc1] | CDCl3 1H (600 Mz): 7.18(4H, m); 6.69(2H, tt, 7.8 Hz, 0.6 Hz); 6.60(4H, dd, J = 9.0 Hz, 0.6 Hz); 3.72(2H, s); 2.99(4H, d, J = 6.6 Hz); 1.92(4H, d, J = 6.6 Hz); 1.59(2H, m); 1.03(4H, m) 13C (400 Mz): 148.71, 129.45, 117.19, 112.82, 50.65, 37.94, 30.96 | | | 294.5 (294.4) |
| WZ30 | 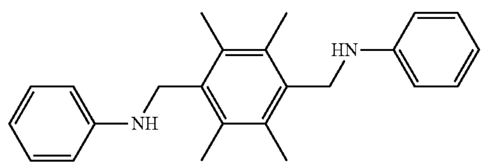 [SMILES: Cc1c(C)c(CNc2ccccc2)c(C)c(C)c1CNc1ccccc1] | CDCl3 1H(600 Mz): 7.26(4H, m); 6.78(2H, t, J = 7.8 Hz); 7.71(4H, d, J = 7.8 Hz); 4.28(4H, s); 3.48(2H, br); 2.32(12H, s) 13C(400 Mz): 148.44, 134.94; 134.31; 129.53; 117.67; 112.73; 43.70, 16.52 | | | 344.7 (344.5) |
| WZ31 | 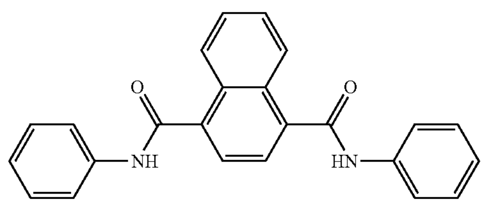 [SMILES: O=C(Nc1ccccc1)c1ccc(C(=O)Nc2ccccc2)c2ccccc12] | DMSO: 400 Mz 1H: 10.66(2H, q, J = 3.2 Hz); 8.24(2H, m); 7.83(6H, m); 6.67(2H, q, J = 3.2 Hz); 7.40(4H, t, J = 7.2 Hz); 7.15(2H, t, J = 7.2 Hz) 13C: 166.84, 139.15, 136.65, 129.79, 128.78 127.30, 125.57, 124.36, 123.88, 119.91, | | | |
| WZ32 | 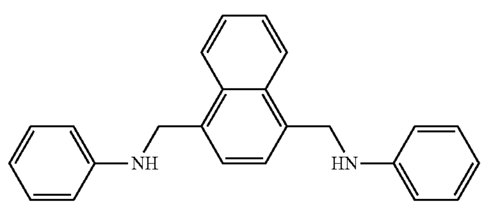 [SMILES: c1ccc(NCc2ccc(CNc3ccccc3)c3ccccc23)cc1] | CDCl3 1H (600 Mz): 8.15(2H, q, J = 3.6 Hz); 7.58(2H, q, J = 3.6 Hz); 7.51(2H, s); 7.23(4H, t, J = 7.2 Hz); 6.77(2H, t, J = 7.2 Hz); 6.71(4H, d, J = 7.2 Hz); 4.76(4H, s); 4.11(2H, br); 13C (400 Mz): 148.24, 134.54, 132.15, 129.56, 126.51, 126.02, 124.58 117.97, 113.06, 46.75 | | | 338.5 (338.4) |
| WZ33 | 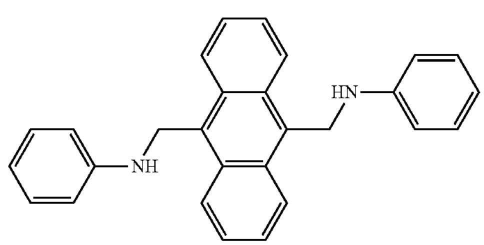 [SMILES: c1ccc(NCc2c3ccccc3c(CNc3ccccc3)c3ccccc23)cc1] | CDCl3: 400 Mz 1H: 8.36(4H, dd, J = 7.2 Hz, 3.2 Hz); 7.55(4H, dd, J = 7.2 Hz, 3.2 Hz); 7.32(4H, t, J = 8.0 Hz); 6.85(6H, m); 5.20(4H, s); 3.98(2H, br) 13C: 148.51, 130.86, 130.53, 129.68, 126.50, 125.13, 118.15, 112.94, 41.34 | | | |
| WZ34 | 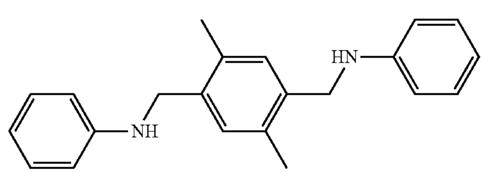 [SMILES: Cc1cc(CNc2ccccc2)c(C)cc1CNc1ccccc1] | CDCl3: 400 Mz 1H: 7.21(6H, m); 6.76(2H, t, J = 7.2 Hz); 6.67(4H, d, J = 8.0 Hz); 4.24(4H, s); 3.90(2H, br); 2.32(6H, s) 13C: 148.42, 136.25, 134.21, 130.85, 129.50, 117.82, 113.04, 46.44, 18.68 | | | 316.5 (316.4) |

TABLE 1-continued

CHARACTERIZATION DATA FOR THE PREPARED COMPOUNDS

| Entry | Structure | ¹HNMR/¹³CNMR | M.p. (° C.) | Element Analysis Found (Calcd.) | MS(EI+): m/z (M⁺) Found (Calcd.) |
|---|---|---|---|---|---|
| WZ35 | 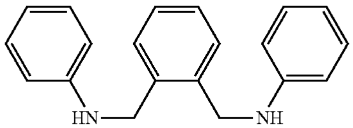 [SMILES: c1ccc(NCc2ccccc2CNc2ccccc2)cc1] | CDCl3 1H (600 Mz): 7.44(2H, m); 7.30(2H, m); 7.19(4H, tt, J = 6.6 Hz, 1.8 Hz); 6.77(2H, t, J = 7.8 Hz); 6.68(4H, d, J = 7.8 Hz); 4.60(2H, br); 4.40(4H, s) 13C (400 Mz): 148.13, 137.44, 129.56, 129.51, 128.17, 118.21, 113.41, 46.55 | | | |
| WZ35S | (2HCl) | DMSO: 400 Mz 1H: 8.25(4H, br); 7.43(2H, m); 7.27(2H, m); 7.16(4H, t, J = 7.8 Hz); 6.79(6H, m); 4.39(4H, s) | | | |
| WZ36 | 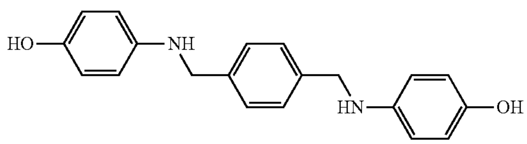 [SMILES: Oc1ccc(NCc2ccc(CNc3ccc(O)cc3)cc2)cc1] | Acetone-d6: 400 Mz 1H: 7.39(2H, s); 7.33(4H, s); 6.61(4H, m); 6.54(4H, m); 4.86(2H, s); 4.23(4H, s) 13C: 149.83, 143.17, 140.13, 128.30, 116.61, 114.88, 49.11 | | | |
| WZ37 | 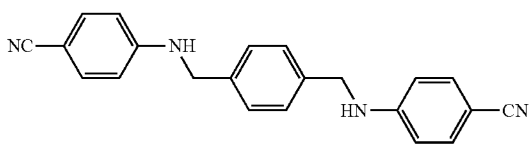 [SMILES: N#Cc1ccc(NCc2ccc(CNc3ccc(C#N)cc3)cc2)cc1] | DMSO: 400 Mz 1H: 7.42(4H, d, J = 9.2 Hz); 7.29(4H, s); 7.26(2H, t, J = 6.0 Hz); 6.63(4H, d, J = 9.2 Hz); 4.30(4H, d, J = 6.0 Hz) 13C: 152.04, 137.68, 133.31, 127.31, 120.54, 112.22, 95.88, 45.41 | | | 338.5 (338.4) |
| WZ38 | 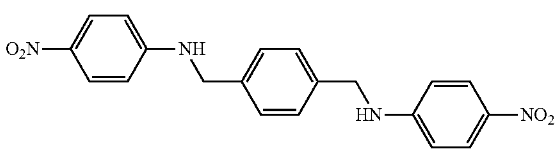 [SMILES: O=[N+]([O-])c1ccc(NCc2ccc(CNc3ccc([N+](=O)[O-])cc3)cc2)cc1] | DMSO: 400 Mz 1H: 7.97(4H, d, J = 9.2 Hz); 7.88(2H, t, J = 5.6 Hz); 6.66(4H, d, J = 9.2 Hz); 4.39(4H, d, J = 5.6 Hz) 13C: 154.40, 137.42, 135.86, 127.42, 126.14, 45.50 | | | |
| WZ40 | 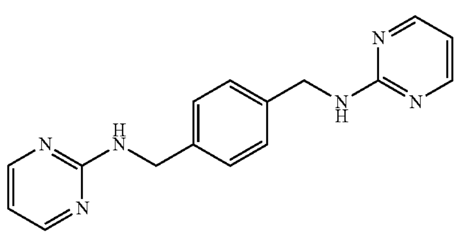 [SMILES: c1cnc(NCc2ccc(CNc3ncccn3)cc2)nc1] | DMSO 1H (600 Mz): 8.24(4H, d, J = 3.2 Hz); 7.63(2H, t, J = 4.0 Hz); 7.21(4H, s); 6.54(2H, t, J = 3.2 Hz); 4.43(4H, d, J = 4.0 Hz) 13C (400 Mz): 162.26, 157.95, 138.59, 126.86, 110.15, 43.62 | | | 292.4 (292.3) |
| WZ41 | 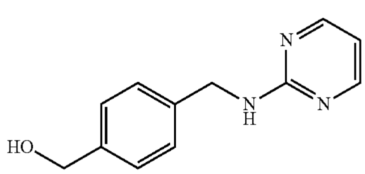 [SMILES: OCc1ccc(CNc2ncccn2)cc1] | CDCl3: 400 Mz 1H: 8.28(2H, d, J = 4.8 Hz); 7.34(4H, s); 6.56(1H, t, J = 4.8 Hz); 5.46(1H, br); 4.69(2H, s); 4.62(2H, d, J = 6.0 Hz); 2.08(1H, s) 13C: 162.27, 157.93 140.71, 138.74, 126.74, | | | 215.2 (215.3) |

TABLE 1-continued

CHARACTERIZATION DATA FOR THE PREPARED COMPOUNDS

| Entry | Structure | ¹HNMR/¹³CNMR | M.p. (° C.) | Element Analysis Found (Calcd.) | MS(EI+): m/z (M⁺) Found (Calcd.) |
|---|---|---|---|---|---|
| | | 126.36, 110.14, 62.73, 43.65 | | | |
| WZ42 | 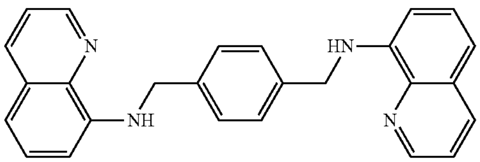 [SMILES: c1cnc2c(NCc3ccc(CNc4cccc5cccnc45)cc3)cccc2c1] | CDCl3 1H (600 Mz): 8.73(2H, dd, J = 3.6 Hz, 1.2 Hz); 8.08(2H, dd, J = 7.8 Hz, 1.2 Hz), 7.43(4H, s); 7.37(4H, m); 7.07(2H, d, J = 7.8 Hz); 6.67(2H, d, J = 7.8 Hz); 6.6(2H, t, J = 5.4 Hz); 4.57(4H, d, J = 5.4 Hz) 13C (400 Mz): 147.14, 144.77, 138.43, 138.36, 136.23, 128.84, 127.98, 127.94, 121.63, 114.36, 105.32, 47.67 | | | |
| WZ43 | 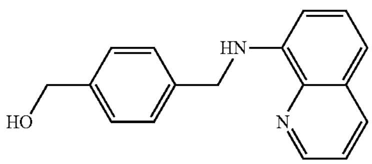 [SMILES: OCc1ccc(CNc2cccc3cccnc23)cc1] | CDCl3: 400 Mz 1H: 8.73(1H, dd, J = 4.0 Hz, 1.6 Hz); 8.08(1H, dd, J = 8.4 Hz, 2.0 Hz); 7.45(2H, d, J = 7.6 Hz); 7.37(4H, m); 7.07(1H, dd, J = 8.4 Hz, 1.6 Hz); 6.63(2H, d, J = 8.4 Hz); 4.70(2H, d, J = 6.0 Hz); 4.58(2H, d, J = 6.0 Hz); 1.66(1H, 6.0 HZ) 13C: 147.14, 144.65, 139.97, 138.90, 138.37, 136.26, 128.82, 127.93, 127.76, 127.55, 121.61, 114.41, 105.39, 65.32, 47.60 | | | |
| WZ48 | 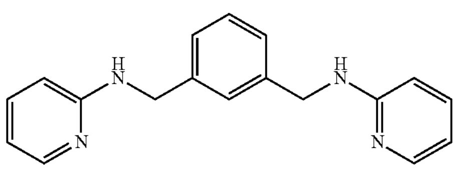 [SMILES: c1ccc(NCc2cccc(CNc3ccccn3)c2)nc1] | CDCl3 1H (600 Mz): 8.10(2H, d, J = 4.8 Hz); 7.40(2H, tt, J = 6.0 Hz, 1.8 Hz); 7.37(1H, s); 7.31(2H, m); 7.28(1H, s); 6.60(2H, t, J = 6.0 Hz); 6.36(2H, d, J = 8.4 Hz); 4.89(2H, t, J = 6.0 Hz); 4.50(4H, d, J = 6.0Hz) 13C (400 Mz): 158.77, 148.44, 139.91, 137.67, 129.16, 126.64, 126.52, 113.42, 107.08, 46.42 | | | |
| WZ48S | 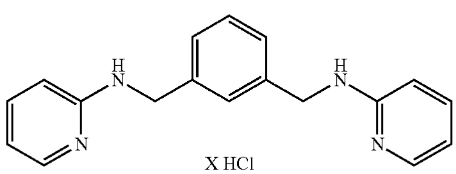 | D2O: 600 Mz 1H: 7.83(2H, td, J = 9 HzHz, 1.2 Hz); 7.72(2H, d, J = 6.6 Hz); 7.45(1H, t, J = 7.8 Hz); 7.36(2H, d, J = 7.8 Hz); 7.27(1H, s); 6.94(2H, d, J = 9.0 Hz); 6.87(2H, t, J = 6.6 Hz); 4.63(4H, s) | | | |
| WZ49 | 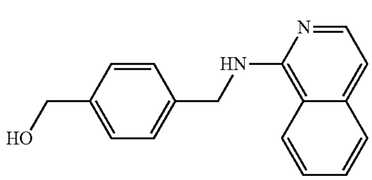 [SMILES: OCc1ccc(CNc2nccc3ccccc23)cc1] | CDCl3: 400 Mz 1H: 8.03(1H, d, J = 6.0 Hz); 7.30(2H, m), 7.61(1H, td, J = 7.6 Hz, 1.2 Hz); 7.46(3H, m); 7.37(2H, m); 6.99(1H, d, J = 5.6 Hz); 5.44(1H, t, J = 6.0 Hz); 4.82(2H, d, J = 6.0 Hz), 4,72(2H, s), 1.79(1H, s) | | | |

TABLE 1-continued
CHARACTERIZATION DATA FOR THE PREPARED COMPOUNDS
| Entry | Structure | ¹HNMR/¹³CNMR | M.p. (° C.) | Element Analysis Found (Calcd.) | MS(EI+): m/z (M⁺) Found (Calcd.) |
|---|---|---|---|---|---|
| | | 13C: 155.01, 141.51, 140.31, 139.06, 137.28, 129.96, 128.49, 127.60, 127.43, 126.17, 121.54, 118.25, 111.52, 65.30, 45.94 | | | |
| WZ50 | 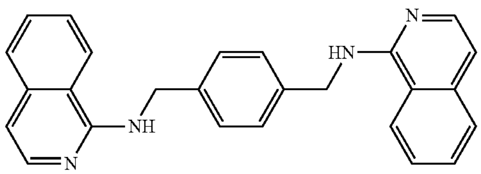 [SMILES: c1ccc2c(NCc3ccc(CNc4nccc5ccccc45)cc3)nccc2c1] | CDCl3: 400 Mz 1H: 8.03(2H, d, J = 6.0 Hz); 7.78(2H, d, J = 8.0 Hz); 7.70(2H, d, J = 8.0 Hz); 7.60(2H, td, J = 7.6 Hz, 1.6 Hz); 7.45(2H, td, J = 7.6 Hz, 1.6 Hz); 7.424(4H, s); 6.98(2H, d, J = 5.2 Hz); 5.57(2H, br); 4.81(4H, d, J = 5.2 Hz) 13C: 154.96, 141.33, 138.71, 137.26, 130.03, 128.59, 127.42, 126.22, 121.69, 118.28, 111.49, 45.90 | | | |
Additional compounds prepared and tested in cell assays to determine viral inhibition:
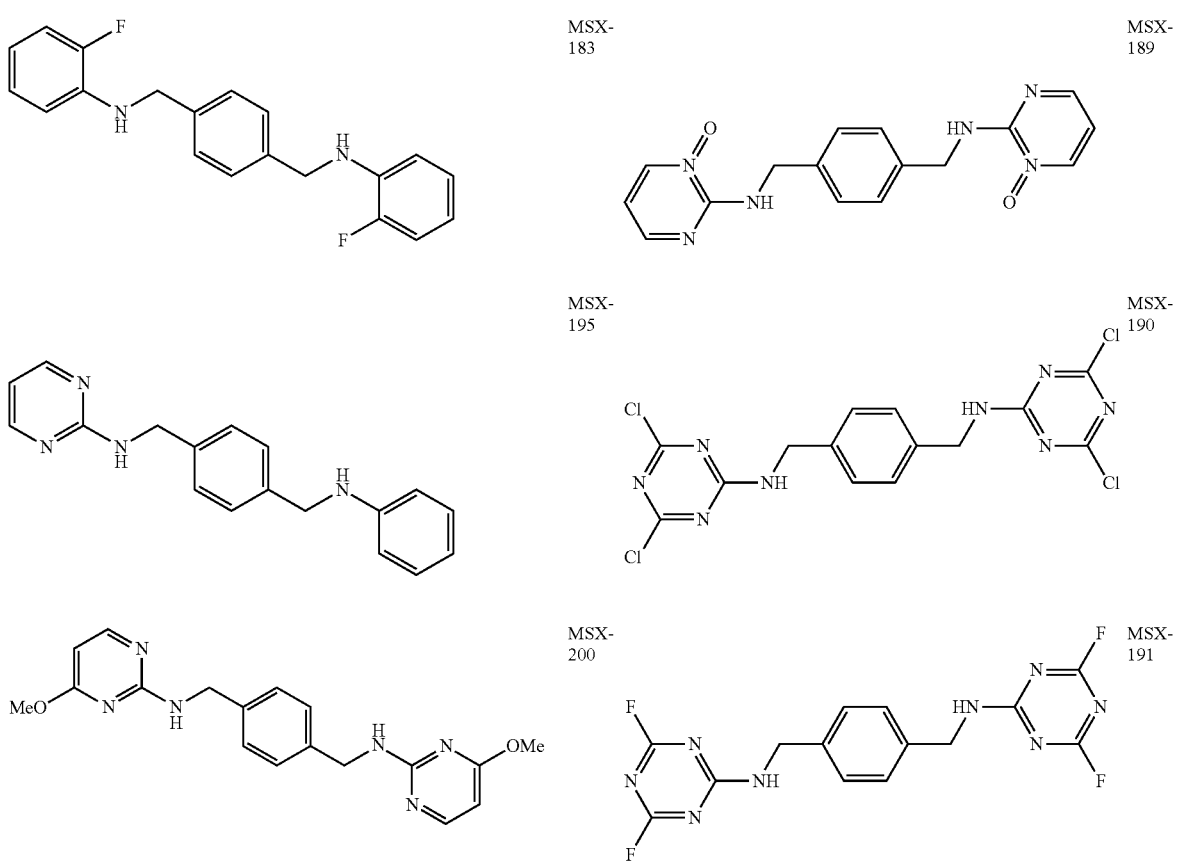

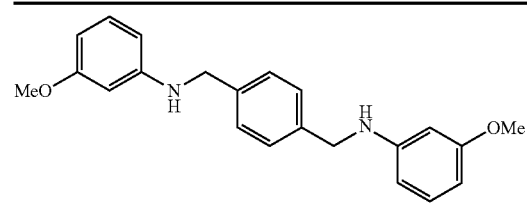
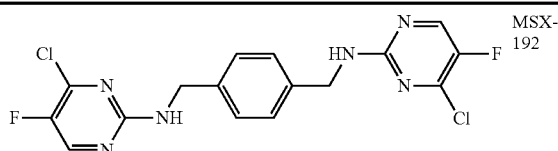 MSX-205 / MSX-192
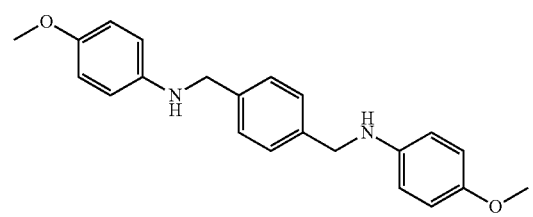
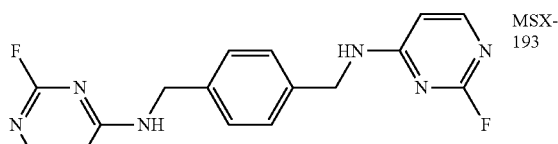 MSX-125 / MSX-193
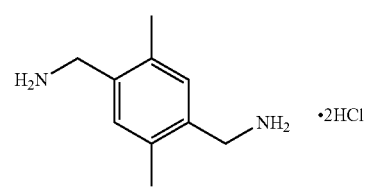
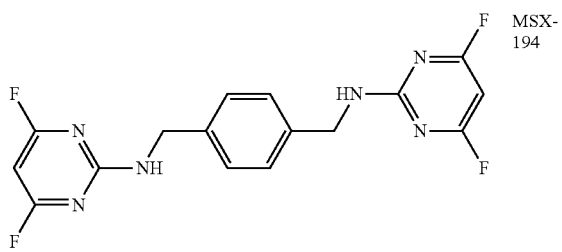 MSX-126 / MSX-194
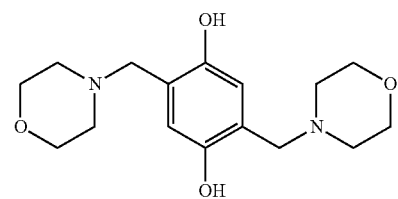 [SMILES: Oc1cc(CN2CCOCC2)c(O)cc1CN1CCOCC1]
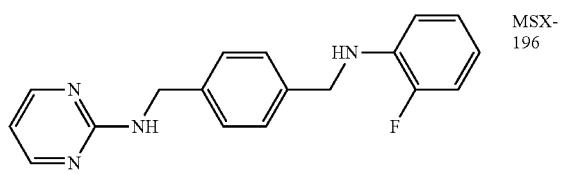 MSX-127 / MSX-196
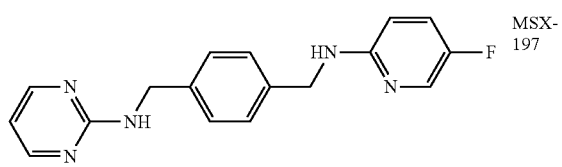 MSX-130 / MSX-197
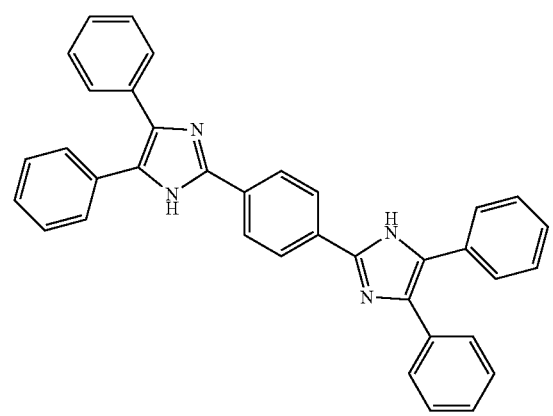 [SMILES: c1ccc(-c2nc(-c3ccc(-c4nc(-c5ccccc5)c(-c5ccccc5)[nH]4)cc3)[nH]c2-c2ccccc2)cc1]
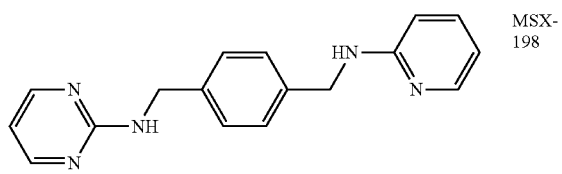 MSX-137 / MSX-198
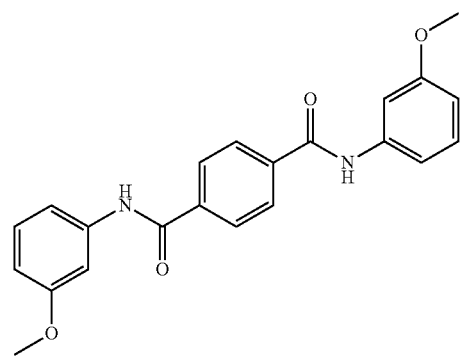 [SMILES: COc1cccc(NC(=O)c2ccc(C(=O)Nc3cccc(OC)c3)cc2)c1]

-continued
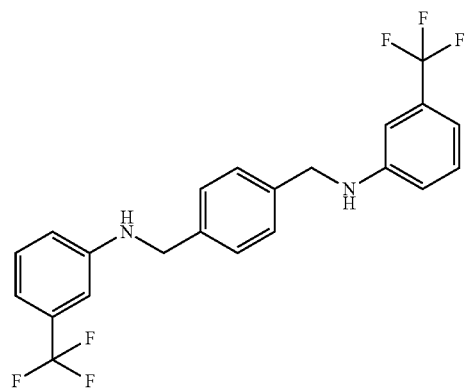 [SMILES: FC(F)(F)c1cccc(NCc2ccc(CNc3cccc(C(F)(F)F)c3)cc2)c1]
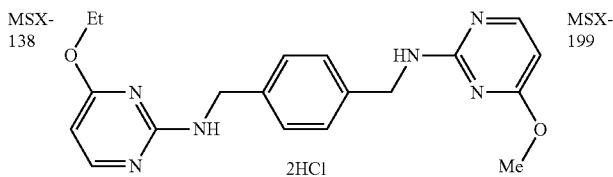
MSX-138
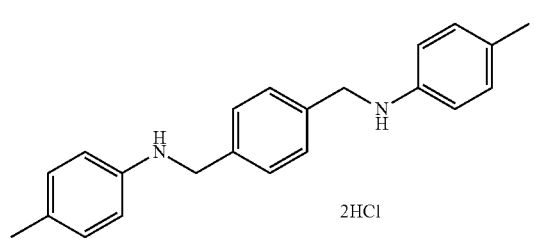
MSX-139
2HCl
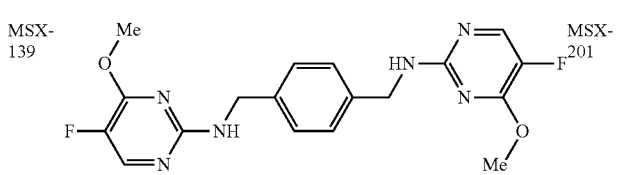
MSX-199
2HCl
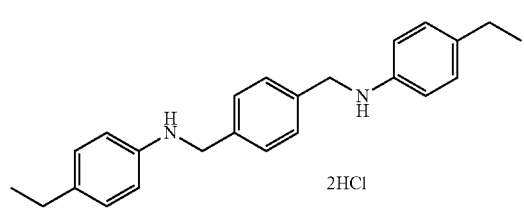 [SMILES: CCc1ccc(NCc2ccc(CNc3ccc(CC)cc3)cc2)cc1]
MSX-140
2HCl
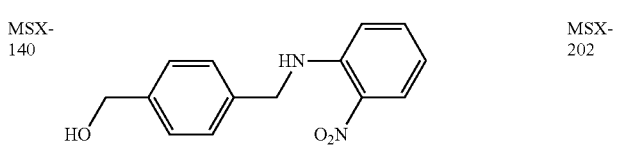
MSX-201
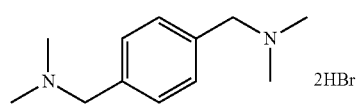
MSX-141
2HBr
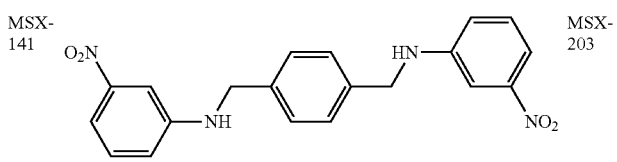
MSX-202
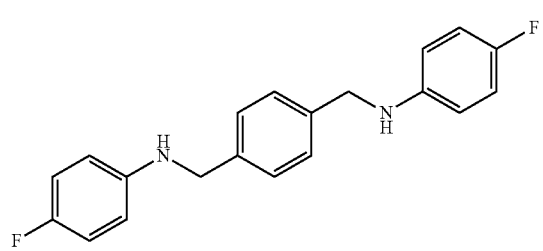 [SMILES: Fc1ccc(NCc2ccc(CNc3ccc(F)cc3)cc2)cc1]
MSX-142
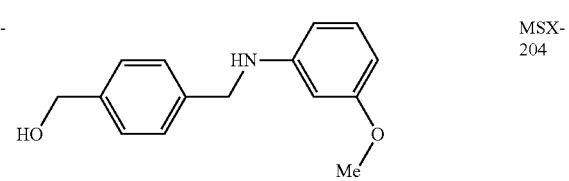
MSX-203
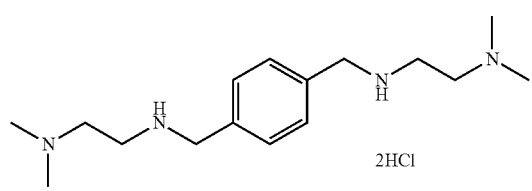
MSX-156s
2HCl
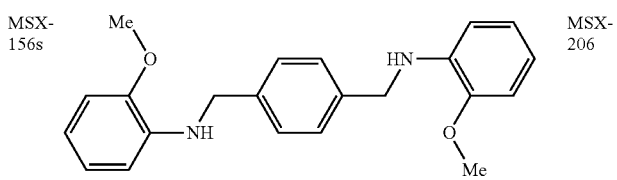
MSX-204
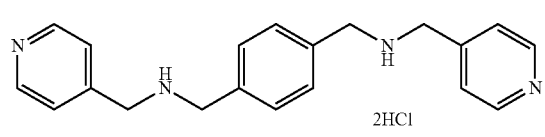 [SMILES: c1cc(CNCc2ccc(CNCc3ccncc3)cc2)ccn1]
MSX-159s
2HCl
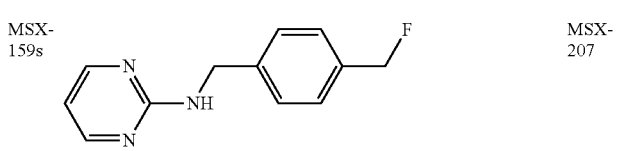
MSX-206
MSX-207

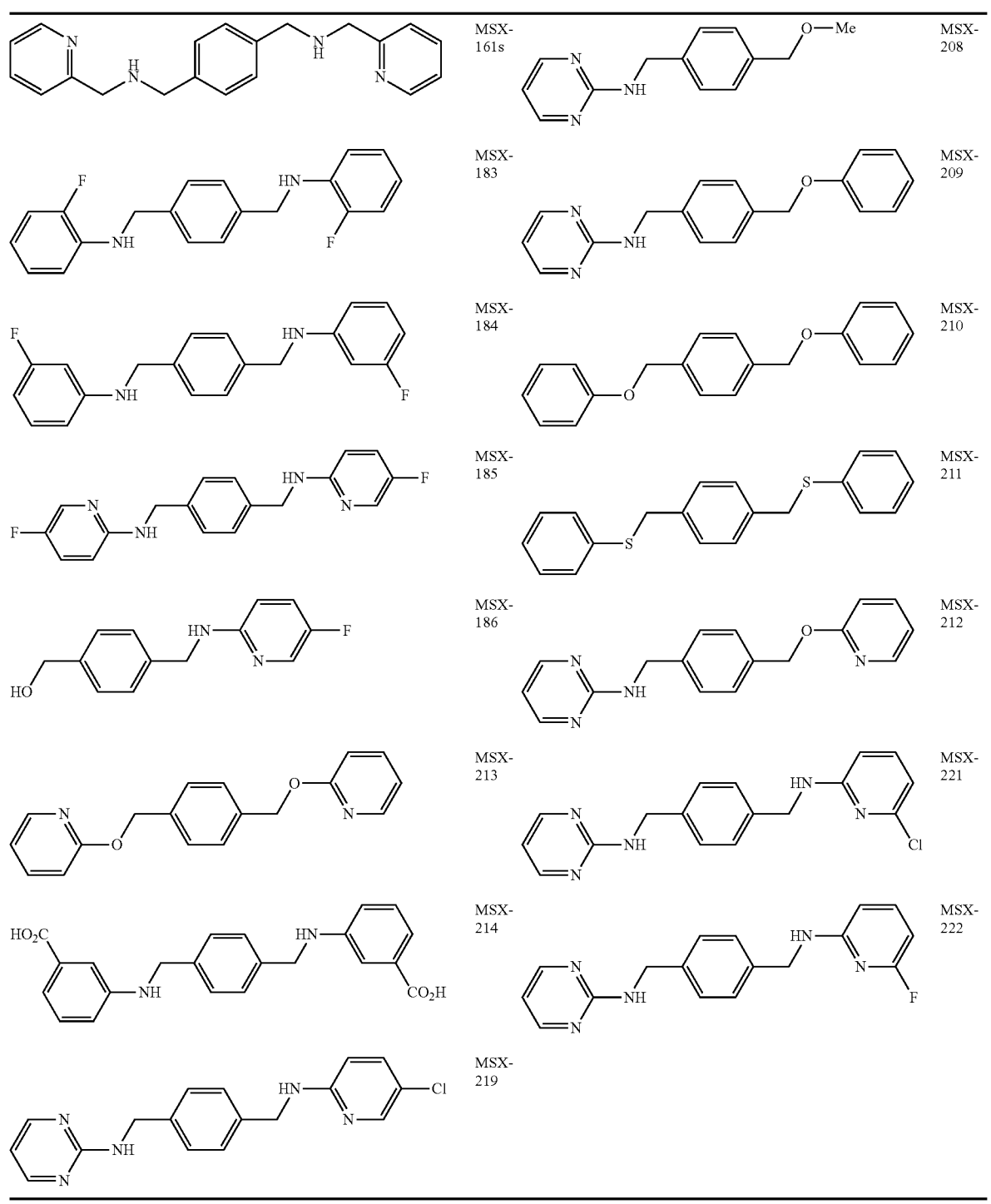

Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The active compound can also be provided as a prodrug, which is converted into a biologically active form in vivo. A prodrug may be converted into the parent drug by various mechanisms, including enzymatic processes and metabolic hydrolysis. Harper, N. J. (1962) in Jucker, ed. *Progress in Drug Research,* 4:221-294; Morozowich et al. (1977) in E. B. Roche ed. *Design of Biopharmaceutical Properties through Prodrugs and Analogs,* APhA (Acad. Pharm. Sci.); E. B. Roche, ed. (1977) *Bioreversible Carriers in Drug in Drug Design, Theory and Application,* APhA; H. Bundgaard, ed. (1985) *Design of Prodrugs,* Elsevier; Wang et al. (1999) *Curr. Pharm. Design.* 5(4):265-287; Pauletti et al. (1997) *Adv. Drug. Delivery Rev.* 27:235-256; Mizen et al. (1998) *Pharm. Biotech.* 11:345-365; Gaignault et al. (1996) *Pract. Med. Chem.* 671-696; M. Asghamej ad (2000) in G. L. Amidon, P. I. Lee and E. M. Topp, *Eds., Transport Proc. Pharm. Sys., Marcell Dekker,* p. 185-218; Balant et al. (1990) *Eur. J. Drug Metab. Pharmacokinet.,* 15(2): 143-53; Balimane and Sinko (1999) *Adv. Drug Deliv.Rev.,* 39(1-3): 183-209; Browne (1997). *Clin. Neuropharm.* 20(1): 1-12; Bundgaard (1979) *Arch. Pharm. Chemi.* 86(1): 1-39; H. Bundgaard, ed. (1985) *Design of Prodrugs,* New York: Elsevier; Fleisher et al. (1996) *Adv. Drug Delivery Rev,* 19(2): 115-130; Fleisher et al. (1985) *Methods Enzymol.* 112: 360-81; Farquhar D, et al. (1983) *J. Pharm. Sci.,* 72(3): 324-325; Han, H. K. et al. (2000) *AAPS Pharm Sci.,* 2(1): E6; Sadzuka Y. (2000) *Curr. Drug Metab.,* 1:31-48; D. M. Lambert (2000) *Eur. J. Pharm. Sci.,* 11 Suppl 2:S1 5-27; Wang, W. et al. (1999) *Curr. Pharm. Des.,* 5(4):265.

The active compound can also be provided as a lipid prodrug. Nonlimiting examples of U.S. patents that disclose suitable lipophilic substituents that can be covalently incorporated into the compound or in lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.).

Method of Treatment

The compounds described herein, are particularly useful for the treatment or prevention of symptoms associated with endocrine disturbances. The host to be treated is any mammal, preferably a human patient and can be either a female or a male, although the ultimate cause of hot flashes can be markedly different for both groups. For example, in female patients the hot flash is typically a primary symptom resulting from menopausal hormonal variation. However, the hot flash can also be drug-induced by anti-estrogen compounds (e.g., tamoxifen, leuprolide acetate, etc.) or surgically-induced by removal of estrogen-producing tissues (e.g., total abdominal hysterectomy, bilateral salpingo-oophorectomy, etc.). In male patients, the hot flashes typically occur as a side-effect of androgen-dependent therapy for metastatic prostate cancer. They can be either surgically-induced (e.g., bilateral orchiectomy) or drug-induced (e.g., treatment with a gonadotrophin-releasing-hormone agonist, leuprolide acetate, etc.).

In certain embodiments, the host is menopause or a premenopausal (also known as perimenopause) female. Menopause is the point in a woman's life when she has not had a menstrual period for 1 year. For most women, menopause happens around age 50, but every woman's body has its own timeline. Some women stop having periods in their mid-40s. Others continue well into their 50s. Pre- or premenopause is the process of change that leads up to menopause. It can start as early as the late 30s or as late as the early 50s. How long premenopause lasts varies, but it usually lasts from 2 to 8 years. Symptoms associated with premenopause include changes in menstrual cycle, hot flashes, night sweats, vaginal dryness, sleep problems, mood changes (mood swings, sadness, or irritability), pain during sex, more urinary infections, urinary incontinence, less interest in sex, increase in body fat around the waist and problems with concentration and memory.

The most well-known effect of menopause is the "hot flash" or "hot flush", a sudden temporary increase in body temperature: the "flash" sensation in a "hot flash" occurs as the body temperature peaks almost instantaneously and begins a much slower return to normal. Hot flashes can become so strong that they can raise the body temperature multiple degrees in a very short period of time, and cause the sufferer to feel weak and break out in heavy sweating. Despite the discomfort to the person, hot flashes are not considered harmful by physicians.

A host can be diagnosed as being in need of treatment by suffering from at least one symptom associated with an endocrine disturbance such as menopause. In particular, a host is in need of treatment if the host has suffered from at least one hot flash, in particular at least one hot flash within the six months prior to treatment. More particularly, the host has suffered from at least one hot flash within three months, or within two months, or within one month prior to treatment.

In some embodiments, the host is suffering from or at risk of suffering from an endocrine disoder. Endocrine disorders include, without limitation, adrenal disorders, including adrenal insufficiencies such as addison's disease, congenital adrenal hyperplasia (adrenogenital syndrome) and mineralocorticoid deficiency, conn's syndrome and cushing's syndrome, adrenogenital syndrome including pheochromocytoma, adrenocortical carcinoma and gra/glucocorticoid remediable aldosteronism; glucose homeostasis disorders such as diabetes mellitus, hypoglycemia (idiopathic hypoglycemia and insulinoma); metabolic bone disease including osteoporosis, osteitis deformans (paget's disease of bone), rickets and osteomalacia; pituitary gland disorders including diabetes insipidus, hypopituitarism (or panhypopituitarism), pituitary tumors (pituitary adenomas, prolactinoma (or hyperprolactinemia), acromegaly, gigantism and cushing's disease); parathyroid gland disorders including primary hyperparathyroidism, secondary hyperparathyroidism, tertiary hyperparathyroidism and hypoparathyroidism (including pseudohypoparathyroidism); sex hormone disorders including disorders of sex development or intersex disorders, hermaphroditism, gonadal dysgenesis and androgen insensitivity syndromes; hypogonadism including gonadotropin deficiency, kallmann syndrome, klinefelter syndrome, ovarian failure, testicular failure and turner syndrome; gender identity disorder; delayed or precocious puberty; menstrual function or fertility disorders including amenorrhea and polycystic ovary syndrome; thyroid disorders including goiter, hyperthyroidism and Graves-basedow disease, hypothyroidism, thyroiditis and thyroid cancer; tumours of the endocrine glands such as multiple endocrine neoplasia types 1, 2a and 2b; and autoimmune polyendocrine syndromes. Certain underlying disorders, such as HIV or certain cancers as described below, can cause endocrine disturbances that lead to symptoms, including hot flashes, in the host suffering from the disorder. In certain embodiments, a method of treatment of a patients suffering from a disorder, such as HIV or certain cancers as described below, that leads to symptoms of endocrine disorders is provided comprising administering the compounds described herein.

In one embodiment, a method of treating or preventing the symptoms associated with endocrine disturbances is provided that includes administering an effective amount of a compound of at least one of Formula (I)-(XVII) to a host in need thereof. In certain embodiments, the host is suffering from premenopausal or menopausal symptoms. In other embodiments, the host is suffering from an endocrine disorder.

In other embodiments, the host is being treated with a drug, and in particular is being treated with a chemotherapeutic agent. In certain embodiments, the symptoms include hot flashes. Women and men who have cancers, in particular those stimulated by sex hormones estrogen and androgen such as breast, uterine and testicular cancers, can get hot flashes as the chemotherapy lowers these body levels. In particular embodiments, the compound is administered to a host at risk of or receiving a chemotherapeutic treatment. In particular embodiments, the host is at risk of or receiving a chemotherapeutic treatment within 10 days or within 9 days, or within 8 days or within 7 days, or within 6 days, or within 5 days or within 4 days, or within 3 days, or within 2 days or within one day or less of receiving the compound or composition.

In some embodiments, the compound is administered after a chemotherapeutic treatment. In particular embodiments, the compound is administered at least one hour after to, or at least two hours after, or at least three hours after, or at least four hours after, or at least five hours after, or at least six hours after, or at least seven hours after, or at least eight hours after, or at least twelve hours after, or at least one day after, the chemotherapeutic treatment.

In some embodiments, the compound is administered prior to or concomitant with a chemotherapeutic treatment. In particular embodiments, the compound is administered at least one hour prior to, or at least two hours prior to, or at least three hours prior to, or at least four hours prior to, or at least five hours prior to, or at least six hours prior to, or at least seven hours prior to, or at least eight hours prior to, or at least twelve hours prior to, or at least one day prior to, the chemotherapeutic treatment.

The active materials can be administered by any appropriate route, for example, orally, parenterally, intravenously, intradermally, subcutaneously, or topically, in liquid or solid form. However, the compounds are particularly suited to oral delivery.

A nonlimiting example of a dose of the compound will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent compound to be delivered. If the salt, ester or prodrug exhibits activity in itself, the effective dosage can be estimated as above using the weight of the salt, ester or prodrug, or by other means known to those skilled in the art.

In one particular embodiment, a method of treating or preventing a symptom of an endocrine disorder, is provided that includes administering a compound of Formula XVI, or a pharmaceutically acceptable salt, ester or prodrug thereof to a host in need thereof:

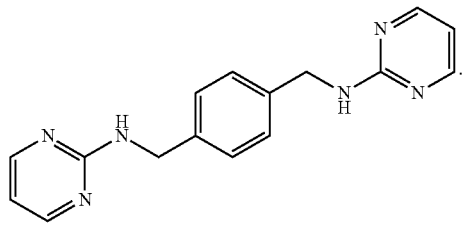

Formula XVI

In a particular subembodiment, the compound is a salt of a compound of Formula XVI, particularly a chloride salt. In typical embodiments, the symptom is a hot flash. In most particular embodiments, the host is suffering from or at risk of suffering from recurrent hot flashes.

Pharmaceutical Compositions

In one embodiment, pharmaceutical compositions for use in preventing or treating a symptom of an endocrine disorder are provided, including at least one compound of any one of Formulas (I)-(XVII) and a pharmaceutically acceptable carrier. In certain embodiments, at least a second active compound is included in the composition. The second active compound can be a chemotherapeutic, particularly an agent active against a primary tumor.

The compound is conveniently administered in unit any suitable dosage form, including but not limited to one containing 7 to 3000 mg, preferably 70 to 1400 mg of active ingredient per unit dosage form. A oral dosage of 50-1000 mg is usually convenient. Ideally the active ingredient should be administered to achieve peak plasma concentrations of the active compound of from about 1 uM to 100 mM or from 0.2 to 700 uM, or about 1.0 to 10 uM.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or antiviral compounds, or with additional chemotherapeutic agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

In a typical embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation. If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Combination and Alternation Therapy

In one embodiment, the compounds described herein are administered in combination or alternation with another active compound.

In one embodiment, the compound is administered in combination or alternation with a hormone replacement therapy. In certain embodiments, the compound is administered in combination or alternation with an estrogen and/or a progesterone or progestin.

In one embodiment, the active compound is a compound that is used as a chemotherapeutic. The compound provided in combination or alternation can, for example, be selected from the following list:

| | | | |
|---|---|---|---|
| 13-cis-Retinoic Acid | 2-Amino-6-Mercaptopurine | 2-CdA | 2-Chlorodeoxyadenosine |
| 5-fluorouracil | 5-FU | 6-TG | 6-Thioguanine |
| 6-Mercaptopurine | 6-MP | Accutane | Actinomycin-D |
| Adriamycin | Adrucil | Agrylin | Ala-Cort |
| Aldesleukin | Alemtuzumab | Alitretinoin | Alkaban-AQ |
| Alkeran | All-transretinoic acid | Alpha interferon | Altretamine |
| Amethopterin | Amifostine | Aminoglutethimide | Anagrelide |
| Anandron | Anastrozole | Arabinosylcytosine | Ara-C |
| Aranesp | Aredia | Arimidex | Aromasin |
| Arsenic trioxide | Asparaginase | ATRA | Avastin |
| BCG | BCNU | Bevacizumab | Bexarotene |
| Bicalutamide | BiCNU | Blenoxane | Bleomycin |
| Bortezomib | Busulfan | Busulfex | C225 |
| Calcium Leucovorin | Campath | Camptosar | Camptothecin-11 |
| Capecitabine | Carac | Carboplatin | Carmustine |
| Carmustine wafer | Casodex | CCNU | CDDP |
| CeeNU | Cerubidine | cetuximab | Chlorambucil |
| Cisplatin | Citrovorum Factor | Cladribine | Cortisone |
| Cosmegen | CPT-11 | Cyclophosphamide | Cytadren |
| Cytarabine | Cytarabine liposomal | Cytosar-U | Cytoxan |
| Dacarbazine | Dactinomycin | Darbepoetin alfa | Daunomycin |
| Daunorubicin | Daunorubicin hydrochloride | Daunorubicin liposomal | DaunoXome |
| Decadron | Delta-Cortef | Deltasone | Denileukin diftitox |
| DepoCyt | Dexamethasone | Dexamethasone acetate | dexamethasone sodium phosphate |
| Dexasone | Dexrazoxane | DHAD | DIC |
| Diodex | Docetaxel | Doxil | Doxorubicin |

| | | | |
|---|---|---|---|
| Doxorubicin liposomal | Droxia | DTIC | DTIC-Dome |
| Duralone | Efudex | Eligard | Ellence |
| Eloxatin | Elspar | Emcyt | Epirubicin |
| Epoetin alfa | Erbitux | Erwinia L-asparaginase | Estramustine |
| Ethyol | Etopophos | Etoposide | Etoposide phosphate |
| Eulexin | Evista | Exemestane | Fareston |
| Faslodex | Femara | Filgrastim | Floxuridine |
| Fludara | Fludarabine | Fluoroplex | Fluorouracil |
| Fluorouracil (cream) | Fluoxymesterone | Flutamide | Folinic Acid |
| FUDR | Fulvestrant | G-CSF | Gefitinib |
| Gemcitabine | Gemtuzumab ozogamicin | Gemzar | Gleevec |
| Gliadel wafer | Glivec | GM-CSF | Goserelin |
| granulocyte colony stimulating factor | Granulocyte macrophage colony stimulating factor | Halotestin | Herceptin |
| Hexadrol | Hexalen | Hexamethylmelamine | HMM |
| Hycamtin | Hydrea | Hydrocort Acetate | Hydrocortisone |
| Hydrocortisone sodium phosphate | Hydrocortisone sodium succinate | Hydrocortone phosphate | Hydroxyurea |
| Ibritumomab | Ibritumomab Tiuxetan | Idamycin | Idarubicin |
| Ifex | IFN-alpha | Ifosfamide | IL - 2 |
| IL-11 | Imatinib mesylate | Imidazole Carboxamide | Interferon alfa |
| Interferon Alfa-2b (PEG conjugate) | Interleukin-2 | Interleukin-11 | Intron A (interferon alfa-2b) |
| Iressa | Irinotecan | Isotretinoin | Kidrolase |
| Lanacort | L-asparaginase | LCR | Letrozole |
| Leucovorin | Leukeran | Leukine | Leuprolide |
| Leurocristine | Leustatin | Liposomal Ara-C | Liquid Pred |
| Lomustine | L-PAM | L-Sarcolysin | Lupron |
| Lupron Depot | Matulane | Maxidex | Mechlorethamine |
| Mechlorethamine Hydrochlorine | Medralone | Medrol | Megace |
| Megestrol | Megestrol Acetate | Melphalan | Mercaptopurine |
| Mesna | Mesnex | Methotrexate | Methotrexate Sodium |
| Methylprednisolone | Meticorten | Mitomycin | Mitomycin-C |
| Mitoxantrone | M-Prednisol | MTC | MTX |
| Mustargen | Mustine | Mutamycin | Myleran |
| Mylocel | Mylotarg | | Navelbine |
| Neosar | Neulasta | Neumega | Neupogen |
| Nilandron | | | |
| Nilutamide | Nitrogen Mustard | Novaldex | Novantrone |
| Octreotide | Octreotide acetate | Oncospar | Oncovin |
| Ontak | Onxal | Oprevelkin | Orapred |
| Orasone | Oxaliplatin | Paclitaxel | Pamidronate |
| Panretin | Paraplatin | Pediapred | PEG Interferon |
| Pegaspargase | Pegfilgrastim | PEG-INTRON | PEG-L-asparaginase |
| Phenylalanine Mustard | Platinol | Platinol-AQ | Prednisolone |
| Prednisone | Prelone | Procarbazine | PROCRIT |
| Proleukin | Prolifeprospan 20 with Carmustine implant | Purinethol | Raloxifene |
| Rheumatrex | Rituxan | Rituximab | Roveron-A (interferon α-2a) |
| Rubex | Rubidomycin hydrochloride | Sandostatin | Sandostatin LAR |
| Sargramostim | Solu-Cortef | Solu-Medrol | STI-571 |
| Streptozocin | Tamoxifen | Targretin | Taxol |
| Taxotere | Temodar | Temozolomide | Teniposide |
| TESPA | Thalidomide | Thalomid | TheraCys |
| Thioguanine | Thioguanine Tabloid | Thiophoamide | Thioplex |
| Thiotepa | TICE | Toposar | Topotecan |
| Toremifene | Trastuzumab | Tretinoin | Trexall |
| Trisenox | TSPA | VCR | Velban |
| Velcade | VePesid | Vesanoid | Viadur |

| | | | |
|---|---|---|---|
| Vinblastine | Vinblastine Sulfate | Vincasar Pfs | Vincristine |
| Vinorelbine | Vinorelbine tartrate | VLB | VM-26 |
| VP-16 | Vumon | Xeloda | Zanosar |
| Zevalin | Zinecard | Zoladex | Zoledronic acid |
| Zometa | | | |

In one embodiment, the compounds of the disclosure are administered in combination with another active agent. The compounds can also be administered concurrently with the other active agent. In this case, the compounds can be administered in the same formulation or in a separate formulation. There is no requirement that the compounds be administered in the same manner. For example, the second active agent can be administered via intravenous injection while the compounds of the disclosure may be administered orally. In another embodiment, the compounds of the disclosure are administered in alternation with at least one other active compound. In a separate embodiment, the compounds of the disclosure are administered during treatment with a chemotherapeutic, such as, for example, an agent listed above, and administration of the compounds of the disclosure is continued after cessation of administration of the other active compound. The compound may be administered for at least a month, at least two months, at least four, six, seven, eight, nine, ten, eleven, twelve months or more to reduce incidence of metastasis.

The compounds of the disclosure can be administered prior to or after cessation of administration of another active compound. In certain cases, the compounds may be administered before beginning a course of treatment for primary tumors, for example, to prevent symptoms associated with endocrine disturbances such as hot flashes. In a separate embodiment, the compounds can be administered after a course of chemotherapy to reduce symptoms of endocrine disturbances.

EXAMPLES

Example 1: Screening of Small Molecule Compounds with a Competitive Binding Assay Against Biotinlabeled TN14003

A synthetic 14-mer peptide, TN14003, was previously reported to block both SDF-1/CXCR4 mediated invasion in vitro and metastasis in vivo with a high specificity by binding competitively with its ligand SDF-1. A competitive binding assay using biotin-labeled TN14003 and streptavidin-conjugated rhodamine was developed to determine the binding efficiency of new chemical entities to the SDF-1 binding domain of CXCR4. Cells incubated with high affinity compounds show only blue nuclear staining, whereas compounds with low affinity result in staining CXCR4 (red; rhodamine) as well as the nuclei (blue; cytox blue). Effective concentrations (EC50) for certain compounds were identified and EC50 for MSX-122 and AMD3100 were 0.6 and 26 nM, respectively.

Example 2: cAMP Assay

Because the major signaling pathway of CXCR4/SDF-1 involves the pertussis toxin-sensitive G protein Gi, compounds described herein were tested as to whether they inhibited SDF-1/CXCR4-mediated cAMP reduction. The absorption increase at 665 nm was determined by varying the concentration of SDF-1 (0-200 ng/ml) to determine EC80 to be 150 ng/ml. With pre-treatment of MSX-122 or AMD3100, the effect of SDF-1 on cAMP reduction was blocked significantly in a dose-dependent manner. While MSX-122 was effective in counteracting SDF-1 function at concentrations as low as 10 nM, AMD3100 required almost 1000 nM to significantly block SDF-1 function.

Example 3: Pharmacokinetics of MSX-122

Oral bioavailability and sustained plasma exposure was consistently observed in multiple species for certain compounds. In an initial pharmacokinetic study in mice, MSX-122 generated sustained blood levels when administered both intraperitoneally (IP) and orally. In a pharmacokinetic study in rats, the oral absorption seemed to occur very quickly with an initial Tmax of ~30 min. and plasma levels remained above 100 ng/ml (342 nM) for 10 hours when it was administered at 10 mg/kg. In a pharmacokinetic/pharmacodynamic study conducted in non-naïve, female cynomolgus monkeys, MSX-122 was administered orally at 1, 5 and 10 mg/kg and resulted in sustained pharmacokinetics with plasma levels that were relatively dose proportional. The 5 and 10 mg/kg doses both generated micromolar plasma concentrations with half lives that support once per day dosing.

Example 4: In Vitro Genotoxicity and Safety

MSX-122 was tested for genotoxicity in an in vitro Ames test (BioReliance Corp., Rockville, Md.) that demonstrated no evidence of mutagenicity and an in vitro chromosome aberration screening test (BioReliance Corp., Rockville, Md.) using CHO cells treated with MSX-122 which showed no statistically significant increase in structural or numerical chromosome aberrations at any dose level up to the highest dose of 2 mM. Sufficiently scorable cells in the presence of S9 were available for 4 hour treatment and in the absence of S9 for a 20 hour treatment. Finally, MSX-122 was tested for its potential to interfere with the rapid delayed rectifier current (IKr) in human ventricles through the cardiac potassium channel, hERG since inhibition of IKr has been reported to be the most common cause of cardiac action potential prolongation by non-cardiac drugs. The resulting data indicate that MSX-122 and analogs do not exert a significant inhibitory effect on hERG channel currents (1 µM MSX-122 (WZ40-MS) 0.2% inhibition).

Example 5: Toxicology Studies in Rats and Monkeys

In initial studies, three groups of rats (5 males and 5 females per group) were dosed with 0, 250 and 600 mg/kg of MSX-122 orally once per day for 28 days. The pharmacokinetic data show that micromolar concentrations of MSX-122 were maintained throughout the term of the study after day 1, and Cmax values were in the range of 2-4 µg/ml (6.8-13.6 µM). No signs or symptoms of toxicity were observed in any of the animals during the study, and no toxicity was observed upon termination from blood serum chemistry or gross necropsy. A 5-day repeat dose study was carried out in two non-naïve cynomolgus monkeys (1 male and 1 female) and two naïve cynomolgus monkeys (1 male and 1 female) dosed with 1,000 and 2,000 mg/kg, respectively, orally once per day for 5 days. No drug-related signs or symptoms of toxicity were observed, and there were no abnormalities in the resulting blood serum chemistry. Gross necropsy of the animals dosed at 2000 mg/kg also revealed no abnormalities or signs of toxicity. The only observations were loose and watery stool in a subset of the animals which may have been caused by the excipients in the formulation. The data showed that micromolar concentrations of MSX-122 were maintained throughout the term of the study with Cmax in the range of 5.1 µM (1.5 µg/ml) to 12 µM (3.5 µg/ml).

Example 6: Treatment of Hot Flashes

An approximately 70 kg 56-year old female with a history of aggressive high grade serous carcinomy in her right fallopian tube, a complete hysterectomy and bilateral oophorectomy after previous treatments with VEGF-Trap and docetaxel, Carboplatin and taxol and doxil was treated with MSX-122, 50 mg/day oral. The woman was suffering from Graves disease and had a history of hot flashes. After her third treatment of MSX-122, she noted that her past history of hot flashes had resolved greatly since starting the trial.

What is claimed:

1. A method of treating hot flashes comprising administering a pharmaceutical composition comprising a compound of Formula I:

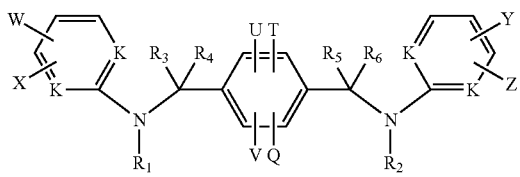

Formula I or a pharmaceutically acceptable salt, ester or prodrug thereof to a subject in need thereof wherein each K is independently N or CH, wherein at least two K's are N;

Q, T, U, and V are independently selected from H or R;

W, X, Y and Z are independently selected from H, R, F, Cl, Br, I, OH, OR or $CO_2H$;

each R is independently selected from straight chain or branched alkyl groups;

$R_1$ and $R_2$ are independently H or R; and $R_3$, $R_4$, $R_5$ and $R_6$ are independently selected from H or R.

2. The method of claim 1, wherein the subject is a menopausal or perimenopausal woman.

3. The method of claim 1, wherein the subject is menstruating or expecting to menstruate within a week.

4. The method of claim 1, wherein the subject is a woman diagnosed with vulvodynia.

5. The method of claim 1, wherein the pharmaceutical composition is administered in combination with another active agent.

6. The method of claim 1, wherein the pharmaceutical composition is administered in combination with an agonist or antagonist of an estrogen receptor.

7. The method of claim 1, wherein the pharmaceutical composition is administered in combination with tamoxifen.

8. The method of claim 1, further comprising the step of administering the pharmaceutical composition to the subject after, before, or during a surgery selected from a hysterectomy, oophorectomy, partial oophorectomy, unilateral salpingo-oophorectomy, bilaterial salpingo-oophorectomy or combination thereof.

* * * * *

UNITED STATES PATENT AND TRADEMARK OFFICE
CERTIFICATE OF CORRECTION

PATENT NO. : 10,632,120 B2
APPLICATION NO. : 16/550414
DATED : April 28, 2020
INVENTOR(S) : Michael G. Natchus et al.

Page 1 of 1

It is certified that error appears in the above-identified patent and that said Letters Patent is hereby corrected as shown below:

On the Title Page

Page 2, item (60), please delete "Provisional application No. 61/556,347, filed on Nov. 7, 2011." and insert --Provisional application No. 61/556,346, filed on Nov. 7, 2011.--

In the Specification

Column 1, Line 17, please delete "Application No. 61/556,347 filed Nov. 7, 2011, the entire" and insert --Application No. 61/556,346 filed Nov. 7, 2011, the entire--

Signed and Sealed this
Ninth Day of November, 2021

Drew Hirshfeld
*Performing the Functions and Duties of the
Under Secretary of Commerce for Intellectual Property and
Director of the United States Patent and Trademark Office*